US 11,708,377 B2

(12) United States Patent
Beaudry et al.

(10) Patent No.: US 11,708,377 B2
(45) Date of Patent: Jul. 25, 2023

(54) ANALOGUES AND DERIVATIVES OF CEPHALOTAXINE AND METHODS FOR MAKING AND USING THE COMPOUNDS

(71) Applicant: Oregon State University, Corvallis, OR (US)

(72) Inventors: Christopher M. Beaudry, Corvallis, OR (US); Xuan Ju, Danbury, CT (US)

(73) Assignee: Oregon State University, Corvallis, OR (US)

( * ) Notice: Subject to any disclaimer, the term of this patent is extended or adjusted under 35 U.S.C. 154(b) by 204 days.

(21) Appl. No.: 17/470,608

(22) Filed: Sep. 9, 2021

(65) Prior Publication Data

US 2022/0009944 A1 Jan. 13, 2022

Related U.S. Application Data

(63) Continuation of application No. PCT/US2020/021734, filed on Mar. 9, 2020.

(60) Provisional application No. 62/816,655, filed on Mar. 11, 2019.

(51) Int. Cl.
*C07D 498/06* (2006.01)
*C07D 491/153* (2006.01)

(52) U.S. Cl.
CPC ....... *C07D 498/06* (2013.01); *C07D 491/153* (2013.01)

(58) Field of Classification Search
CPC .......................... C07D 491/153; C07D 498/18
See application file for complete search history.

(56) References Cited

U.S. PATENT DOCUMENTS

| | | |
|---|---|---|
| 2004/0186095 A1 | 9/2004 | Robin et al. |
| 2011/0071097 A1 | 3/2011 | Gin et al. |
| 2018/0134724 A1 | 5/2018 | Herr et al. |

FOREIGN PATENT DOCUMENTS

| | | |
|---|---|---|
| WO | WO 2009/148654 A2 | 12/2009 |
| WO | WO 2009/148654 A3 | 12/2009 |
| WO | WO 2016/182850 | 11/2016 |

OTHER PUBLICATIONS

Eckelbarger et al., "Synthesis of Antiproliferative *Cephalotaxus* Esters and Their Evaluation against Several Human Hematopoietic and Solid Tumor Cell Lines: Uncovering Differential Susceptibilities to Multidrug Resistance," *Chemistry—A European Journal* 14(14):4293-4306, 2008, published online Mar. 25, 2008.

Ju et al., "Total Synthesis of (−)-Cephalotaxine and (−)-Homoharringtonine Furan Oxidation-Transannular Mannich Cyclization," *Angewandte Chemie* 131:6824-6827, 2019, published online Mar. 13, 2019.

International Search Report and Written Opinion dated May 7, 2020 from International Application No. PCT/US2020/021734 (10 pages).

*Primary Examiner* — Susanna Moore
(74) *Attorney, Agent, or Firm* — Klarquist Sparkman, LLP

(57) ABSTRACT

Disclosed herein are embodiments of a compound having a Formula I

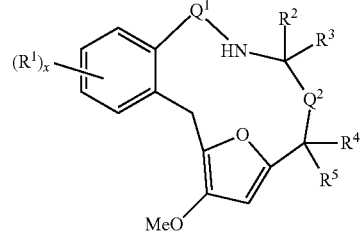

Formula I or a salt, solvate, N-oxide, prodrug, diastereomer or enantiomer thereof. Also disclosed are derivative compounds made from the compound of Formula I. Certain derivative compounds have a Formula V-2, or a salt, solvate, N-oxide, prodrug, diastereomer or enantiomer thereof.

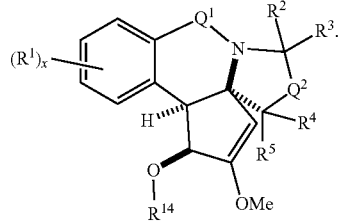

Formula V-2

Also disclosed are method for making and using the disclosed compounds. Certain disclosed embodiments are useful for treating and/or preventing certain diseases and/or disorders, including proliferation diseases, such as leukemia.

26 Claims, No Drawings

ANALOGUES AND DERIVATIVES OF CEPHALOTAXINE AND METHODS FOR MAKING AND USING THE COMPOUNDS

CROSS REFERENCE TO RELATED APPLICATION

This application is a continuation of International Application No. PCT/US2020/021734, filed on Mar. 9, 2020, which was published in English under PCT Article 21(2), which in turn claims the benefit of the earlier filing date of U.S. provisional patent application No. 62/816,655, filed Mar. 11, 2019, both of which are incorporated herein by reference in their entireties.

ACKNOWLEDGMENT OF GOVERNMENT SUPPORT

This invention was made with government support under Grant No. CHE-1465287 awarded by the National Science Foundation. The government has certain rights in the invention.

FIELD

The present disclosure concerns analogues of cephalotaxine, derivative compounds made from cephalotaxine and its analogues, and method of making and using the compounds.

BACKGROUND (−)-Homoharringtonine (HHT) is a polycyclic alkaloid isolated from the plum yew *Cephalotaxus harringtonii*. HHT binds to the peptidyl transferase center of the human ribosome and inhibits protein translation, showing nanomolar cytotoxicity against leukemia cells. HHT was approved for treating chronic myeloid leukemia in the United States in 2012.

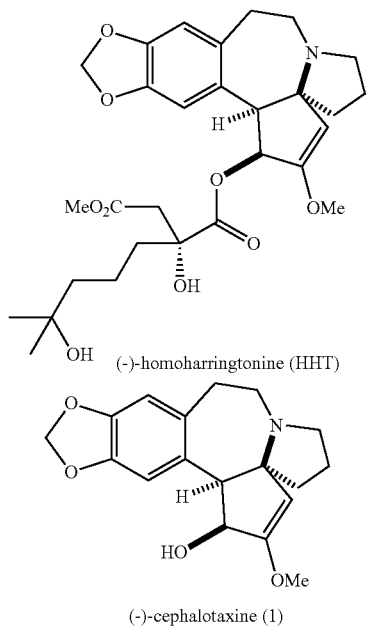

Total syntheses of HHT have been reported; however, HHT is prepared commercially by esterification of (−)-cephalotaxine (1), a related alkaloid also found in *C. harringtonii*. Cephalotaxine is more abundant in the plant than HHT (ca. 50% of the alkaloid content), but it lacks the ester sidechain of HHT and is biologically inactive. Cephalotaxine was first synthetically prepared by Weinreb in 1972, and has been prepared by several groups since. However, despite such efforts, a commercially viable synthetic route to cephalotaxine has not been developed and therefore commercial HHT is still prepared from plant-derived cephalotaxine.

SUMMARY

Disclosed herein are analogues of cephalotaxine. In some embodiments, the compounds have a Formula I, or a salt, hydrate, N-oxide, prodrug, diastereomer or enantiomer thereof.

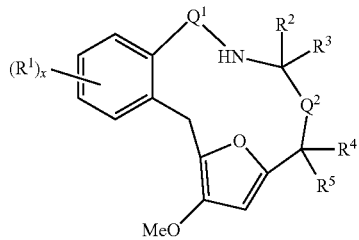

Formula I

With respect to Formula I, x is from 0 to 4, and if present, each $R^1$ independently is hydroxyl, halogen, aliphatic, such as alkyl, alkoxy, haloalkyl, amino, protected amino, carboxylic ester, or two $R^1$s, together with the atoms to which they are attached, form an aryl or heterocyclyl. Each of $R^2$, $R^3$, $R^4$ and $R^5$ independently may be H, halogen, aliphatic, such as alkyl, hydroxyalkyl, protected hydroxyalkyl, aryl, heteroaryl, hydroxyl, protected hydroxyl, haloalkyl, amino, protected amino, carboxylic ester, or two of $R^2$, $R^3$, $R^4$ and $R^5$ that are attached to the same carbon together form =O or =S. And in some embodiments, each of $R^2$, $R^3$, $R^4$ and $R^5$ independently is halogen, alkyl, hydroxyalkyl, protected hydroxyalkyl, phenyl, heteroaryl, hydroxyl, protected hydroxyl, or two of $R^2$, $R^3$, $R^4$ and $R^5$ that are attached to the same carbon together form =O or =S. And in any embodiments, each of $Q^1$ and $Q^2$ independently is aliphatic, such as alkyl, typically $C_{1-2}$alkyl.

Also disclosed are compounds made from a compound of Formula I. Such compounds may have a formula selected from

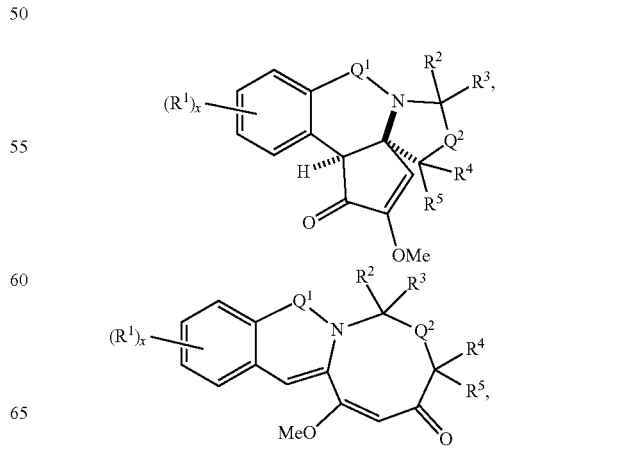

3
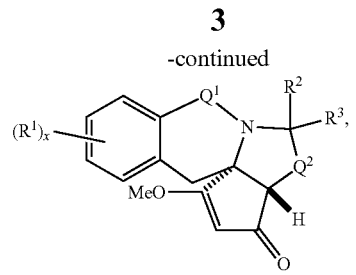
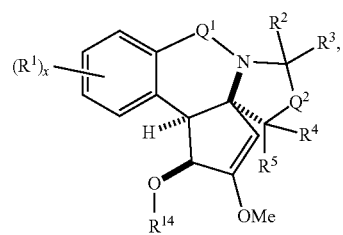
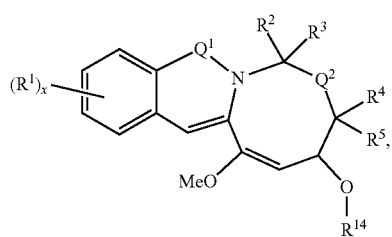
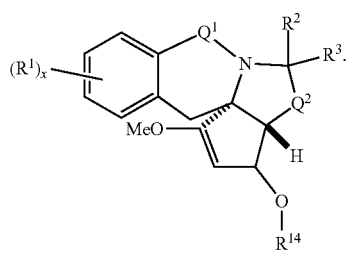
With respect to these formulas, x, R¹-R⁵, Q¹ and Q² are as defined above for Formula I, and R¹⁴ is H, aliphatic, acyl, aryl, or heterocyclyl. In some embodiments, the compound is not
4
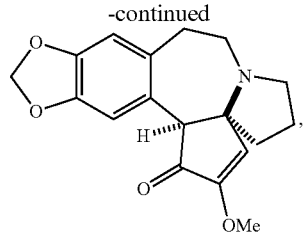
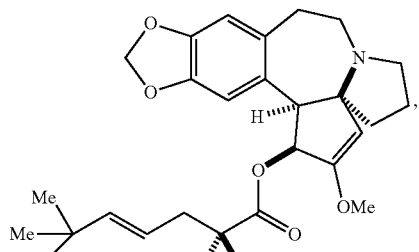
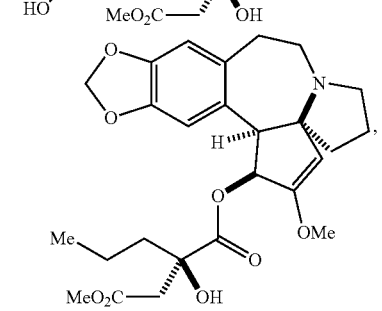
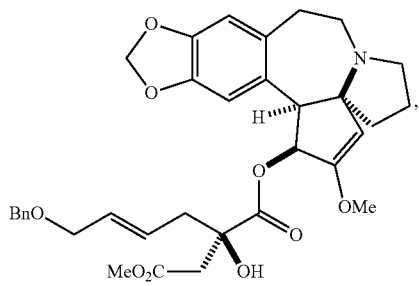
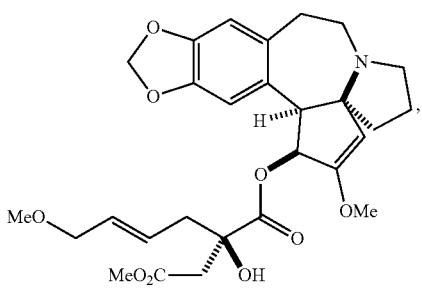
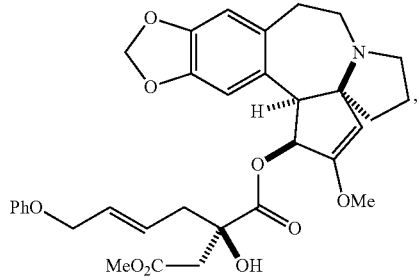

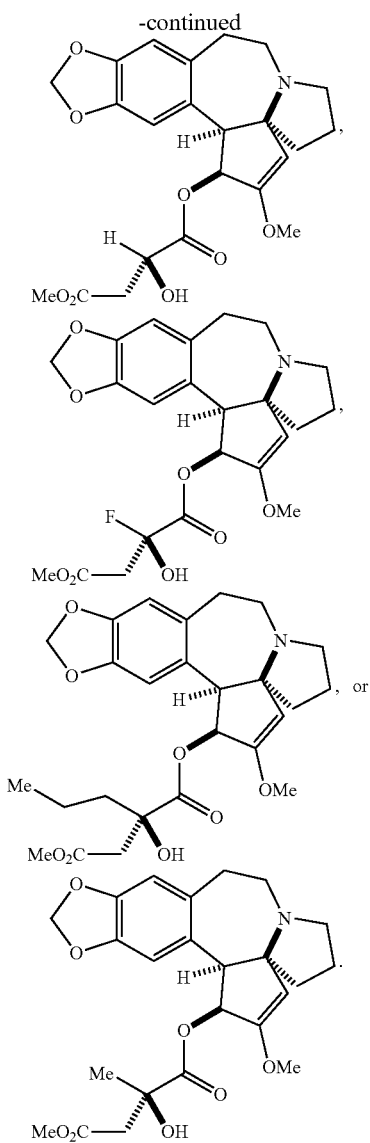

With respect to any of the formulas disclosed herein, x may be 2, 3, or 4, and/or two $R^1$s together with the atoms to which they are attached, form an aryl or heterocyclyl ring. The heterocyclyl ring may be a 5- or 6-membered heteroaryl, such as a pyridinyl, imidazolyl, pyrazolyl, pyrrolyl, oxazolyl, thiazolyl, furanyl, or thiophenyl. Alternatively, the heterocyclyl may be a 5- or 6-membered non-aromatic heterocyclyl, such as 1,3-dioxole, 1,4-dioxine, 2,3-dihydro-1,4-dioxine, 1,4-oxazine, or 3,4-dihydro-1,4-oxazine.

In any embodiments, $Q^1$ may be $C_{1-2}$alkyl, and may be unsubstituted, such as —$CH_2$— or —$CH_2CH_2$—, or substituted, such as with 1, 2, 3, or 4 substituents. And/or $Q^2$ may be $C_{1-2}$alkyl, and may be unsubstituted, such as —$CH_2$— or —$CH_2CH_2$—, or substituted, such as with 1, 2, 3, or 4 substituents. $Q^1$ and/or $Q^2$ may be substituted with halogen, alkyl, hydroxyalkyl, protected hydroxyalkyl, =O, =S, aryl, hydroxyl, protected hydroxyl, haloalkyl, amino, protected amino, carboxylic ester, or a combination thereof, such as halogen, alkyl, hydroxyalkyl, protected hydroxyalkyl, =O, =S, aryl, hydroxyl, protected hydroxyl, or a combination thereof.

In certain embodiments, $Q^1$ is $C_1$alkyl, and may be substituted with methyl, ethyl, hydroxyl, phenyl, hydroxyethyl, hydroxypropyl, or a protected derivative thereof. In other embodiments, $Q^1$ is $C_2$alkyl, and may be substituted with methyl, ethyl, =O, =S, hydroxyl, phenyl, hydroxyethyl, hydroxypropyl, or a protected derivative thereof.

In some embodiments, $Q^2$ is $C_1$alkyl, while in other embodiments, $Q^2$ is $C_2$alkyl. In any embodiments, $Q^2$ may be substituted with Cl, methyl, ethyl, =O, =S, hydroxyl, protected hydroxyl, hydroxyethyl, hydroxypropyl, or a protected derivative thereof, or a combination thereof.

In embodiments where the compound comprises a protected hydroxyl, protected hydroxyalkyl, and/or protected amino, each protecting group independently may be any suitable protecting group known to a person of ordinary skill in the art, such as the protecting groups disclosed herein. In certain embodiments, each protecting group independently is methoxymethyl (MOM), tert-butyl, iso-propyl, tert-butyldimethylsilyl (TBS or TBDMS), trimethylsilyl (TMS), triethylsilyl (TES), tert-butyldiphenylsilyl (TBDPS), or tri-isopropylsilyl (TIPS).

Also disclosed are embodiments of a composition comprising the compound of any of the formulas disclosed herein, and a pharmaceutically acceptable excipient. And further disclosed is a method for administering one or more of the disclosed compounds, or a composition comprising the compound(s). The compound, or a composition thereof, may be administered to a subject, such as a human or animal subject. The method may be a method for treating and/or preventing a disease, such as a proliferation disease, such as a non-solid tumor cancer. In some embodiments, the proliferation disease is leukemia.

Embodiments of a composition comprising a compound of Formula I and an oxidizing agent also are disclosed. In some embodiments, the oxidizing agent is DDQ.

Other embodiments concern a method for making the disclosed compounds. The method may comprise:

i) treating a protected hydroxyl ketone of formula A-1 with a haloacetate ester of formula A-2 to form a compound of formula A-3

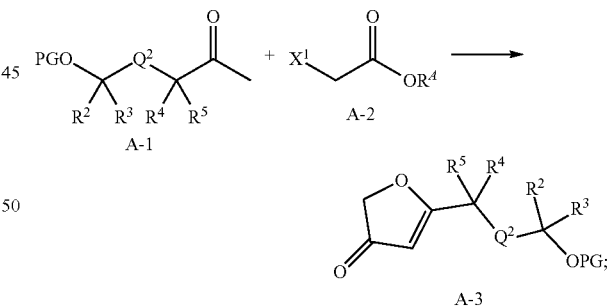

ii) treating the compound of formula A-3 with a compound of formula A-4 to form a compound of formula A-5

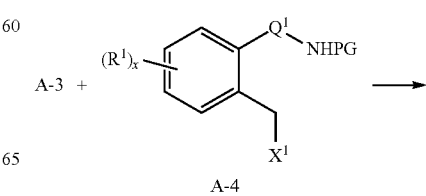

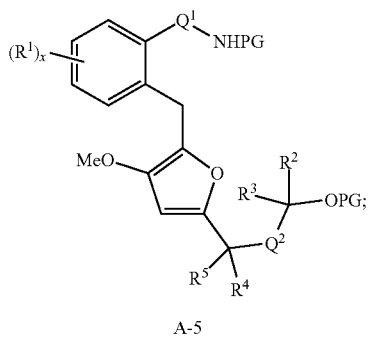

A-5 iii) converting the protected hydroxyl moiety of A-5 to a leaving group in a compound of formula A-6

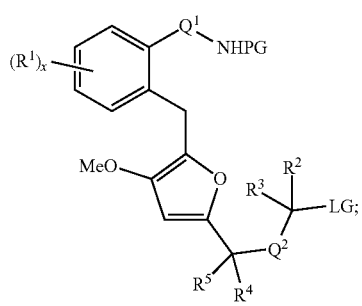

and iv) cyclizing A-6 to form the compound of Formula I as disclosed herein.

With respect to this method, each PG independently is a protecting group, such as trifluoroacetate or a silyl protecting group; LG is a leaving group, such as mesylate; $R^4$ is alkyl, such as $C_{1-6}$alkyl, or $C_{1-2}$alkyl; each $X^1$ independently is a halogen, typically, Cl; and x, $R^1$, $Q^1$, and $Q^2$ are as defined herein for Formula I.

The method may further comprise intramolecularly cyclizing the compound of Formula I, such as by providing an oxidizing agent, such as DDQ, to form a compound of Formula II. The compound of Formula II may be a racemic mixture of chiral isomers. Optionally, the method may also comprise treating the racemic compound of Formula II with Ru(p-cymene)-(S,S)-TsDPEN, trimethylamine, and formic acid to form a compound of Formula A-7 and (+)-compound of Formula II

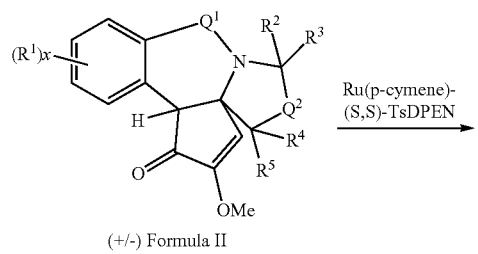

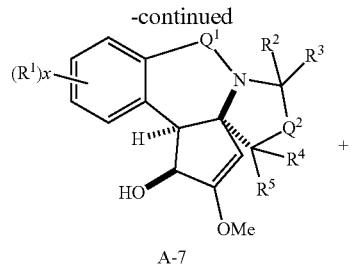

A-7

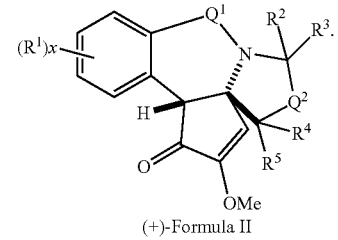

(+)-Formula II

Also disclosed are embodiments of a method for forming a racemate of a compound of Formula II, comprising treating the (+)-compound of Formula II with 2,2-dimethoxypropane and p-toluene sulfonic acid to form the racemate.

The foregoing and other objects, features, and advantages of the invention will become more apparent from the following detailed description.

DETAILED DESCRIPTION

I. Definitions

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference in their entirety, unless otherwise specified.

Unless otherwise indicated, all numbers expressing quantities of components, molecular weights, percentages, temperatures, times, and so forth, as used in the specification or claims, are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is expressly recited.

Unless explained otherwise, all technical and scientific terms used herein have the same meaning as commonly understood by one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

When chemical structures are depicted or described, unless explicitly stated otherwise, all carbons are assumed to include implicit hydrogens such that each carbon conforms to a valence of four. For example, in the structure on the left-hand side of the schematic below there are nine hydrogen atoms implied. The nine hydrogen atoms are depicted in the right-hand structure.

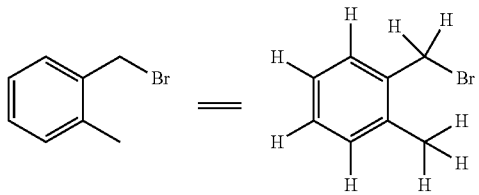

Sometimes a particular atom in a structure is described in textual formula as having a hydrogen or hydrogen atoms, for example —CH$_2$CH$_2$—. It will be understood by a person of ordinary skill in the art that the aforementioned descriptive techniques are common in the chemical arts to provide brevity and simplicity to description of organic structures.

If a group R is depicted as "floating" on a ring system, as for example in the group:

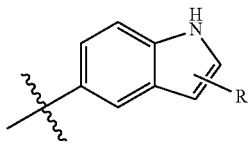

then, unless otherwise defined, a substituent R can reside on any atom of the fused bicyclic ring system, so long as a stable structure is formed that conforms to standard valence conditions as understood by a person of ordinary skill in the art. In the example depicted, the R group can reside on an atom in either the 5-membered or the 6-membered ring of the indolyl ring system, including the heteroatom by replacing the explicitly recited hydrogen, but excluding the atom carrying the bond with the ～ symbol and the bridging carbon atoms.

When there are more than one such depicted "floating" groups, as for example in the formulae:

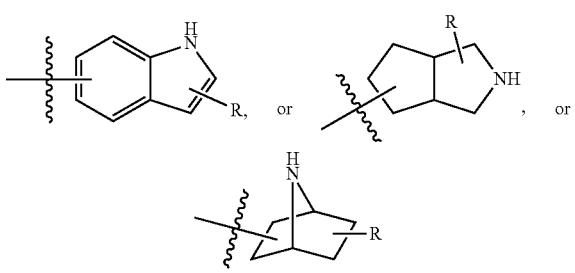

where there are two groups, namely, the R and the bond indicating attachment to a parent structure; then, unless otherwise defined, each "floating" group can reside on any atoms of the ring system, including germinal substitution, again assuming each replaces a depicted, implied, or expressly defined hydrogen on the ring system and a chemically stable compound would be formed by such an arrangement.

When a group R is depicted as existing on a ring system containing saturated carbons, for example as in the formula:

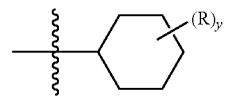

where, in this example, y can be more than one, and assuming each R replaces a currently depicted, implied, or expressly defined hydrogen on the ring; then, unless otherwise defined, two R's can reside on the same carbon. A simple example is when R is a methyl group. The depicted structure can exist as a geminal dimethyl on a carbon of the depicted ring (an "annular" carbon). In another example, two R's on the same carbon, including that same carbon, can form a ring, thus creating a spirocyclic ring (a "spirocyclyl" group) structure. For example, shown below two Rs can form a piperidine ring in a spirocyclic arrangement with the cyclohexane:

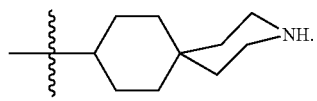

"Substituted," when used to modify a specified group or moiety, means that at least one, and perhaps two or more, hydrogen atoms of the specified group or moiety is independently replaced with the same or different substituent groups as defined below. In a particular embodiment, a group, moiety or substituent may be substituted or unsubstituted, unless expressly defined as either "unsubstituted" or "substituted." Accordingly, any of the groups specified herein may be unsubstituted or substituted. In particular embodiments, the substituent may or may not be expressly defined as substituted, but is still contemplated to be optionally substituted. For example, an "alkyl" moiety may be unsubstituted or substituted, but an "unsubstituted alkyl" is not substituted.

As used herein, the term "substituted" refers to all subsequent modifiers in a term, for example in the term "substituted arylC$_{1-8}$alkyl," substitution may occur on the "C$_{1-8}$ alkyl" portion, the "aryl" portion or both portions of the arylC$_{1-8}$alkyl group.

"Substituents" or "substituent groups" for substituting for one or more hydrogen atoms the specified group or moiety are, unless otherwise specified, halogen; aliphatic, such as alkyl, alkenyl, or alkynyl, preferably C$_{1-6}$alkyl or C$_{1-4}$alkyl; hydroxyl; hydroxylalkyl; protected hydroxyl; protected hydroxyalkyl; alkoxy; acyl; aryl; heteroaryl; cycloaliphatic; —O-aryl; —O-heterocyclyl; —O-cycloaliphatic, such as —O-cycloalkyl; —O-aliphatic; haloalkyl, such as CF$_3$; —O-haloalkyl; CO$_2$H; carboxylic ester, such as CO$_2$R where R is alkyl; CN; NO$_2$; amino; protected amino; =O; =S; or a combination thereof.

In one embodiment, a group that is substituted has at least one substituent up to the number of substituents possible for a particular moiety, such as 1 substituent, 2 substituents, 3 substituents, or 4 substituents.

Additionally, in embodiments where a group or moiety is substituted with a substituted substituent, the nesting of such substituted substituents is limited to three, thereby preventing the formation of polymers. Thus, in a group or moiety comprising a first group that is a substituent on a second group that is itself a substituent on a third group, which is attached to the parent structure, the first (outermost) group can only be substituted with unsubstituted substituents. For example, in a group comprising -(aryl-1)-(aryl-2)-(aryl-3), aryl-3 can only be substituted with substituents that are not themselves substituted.

Any group or moiety defined herein can be connected to any other portion of a disclosed structure, such as a parent or core structure, as would be understood by a person of ordinary skill in the art, such as by considering valence rules, comparison to exemplary species, and/or considering functionality, unless the connectivity of the group or moiety to the other portion of the structure is expressly stated, or is implied by context.

"Acyl" refers to the group —C(O)R, where R is H, aliphatic, such as alkyl, alkenyl, or alkynyl, heterocyclic or aryl. Exemplary acyl moieties include, but are not limited to, —C(O)H, —C(O)alkyl, —C(O)$C_1$-$C_{10}$alkyl, —C(O)$C_1$-$C_6$haloalkyl, —C(O)cycloalkyl, —C(O)alkenyl, —C(O)aryl, —C(O)heteroaryl, or —C(O)heterocyclyl. An acyl group can be substituted or unsubstituted unless otherwise specified. Specific examples include —C(O)H, —C(O)Me, —C(O)Et, or —C(O)cyclopropyl.

"Aliphatic" refers to a substantially hydrocarbon-based group or moiety. An aliphatic group or moiety can be acyclic, including alkyl, alkenyl, or alkynyl groups, cyclic versions thereof, such as cycloaliphatic groups or moieties including cycloalkyl, cycloalkenyl or cycloalkynyl, and further including straight- and branched-chain arrangements, and all stereo and position isomers as well. Unless expressly stated otherwise, an aliphatic group contains from one to twenty-five carbon atoms ($C_{1-25}$); for example, from one to fifteen ($C_{1-15}$), from one to ten ($C_{1-10}$), from one to six ($C_{1-6}$), or from one to four carbon atoms ($C_{1-4}$) for a saturated acyclic aliphatic group or moiety, from two to twenty-five carbon atoms ($C_{2-25}$); for example, from two to fifteen ($C_{2-15}$), from two to ten ($C_{2-10}$), from two to six ($C_{2-6}$), or from two to four carbon atoms ($C_{2-4}$) for an unsaturated acyclic aliphatic group or moiety, or from three to fifteen ($C_{3-15}$) from three to ten ($C_{3-10}$), from three to six ($C_{3-6}$), or from three to four ($C_{3-4}$) carbon atoms for a cycloaliphatic group or moiety. An aliphatic group may be substituted or unsubstituted, unless expressly referred to as an "unsubstituted aliphatic" or a "substituted aliphatic." An aliphatic group can be substituted with one or more substituents (up to two substituents for each methylene carbon in an aliphatic chain, or up to one substituent for each carbon of a —C=C— double bond in an aliphatic chain, or up to one substituent for a carbon of a terminal methine group).

"Lower aliphatic" refers to an aliphatic group containing from one to ten carbon atoms ($C_{1-10}$), such as from one to six ($C_{1-6}$), or from one to four ($C_{1-4}$) carbon atoms for a saturated acyclic lower aliphatic group or moiety; from two to ten ($C_{2-10}$), from two to six ($C_{2-6}$), or from two to four carbon atoms ($C_{2-4}$) for an unsaturated acyclic lower aliphatic group or moiety; or from three to ten ($C_{3-10}$), such as from three to six ($C_{3-6}$) carbon atoms for a lower cycloaliphatic group.

"Alkoxy" refers to the group —OR, where R is a substituted or unsubstituted alkyl or a substituted or unsubstituted cycloalkyl group. In certain examples R is a $C_{1-6}$ alkyl group or a $C_{3-6}$cycloalkyl group. Methoxy (—OCH$_3$) and ethoxy (—OCH$_2$CH$_3$) are exemplary alkoxy groups. In a substituted alkoxy, R is substituted alkyl or substituted cycloalkyl, examples of which include haloalkoxy groups, such as —OCF$_2$H, or —OCF$_3$.

"Alkyl" refers to a saturated aliphatic hydrocarbyl group having from 1 to 25 ($C_{1-25}$) or more carbon atoms, more typically 1 to 10 ($C_{1-10}$) carbon atoms such as 1 to 6 ($C_{1-6}$) carbon atoms, 1 to 4 ($C_{1-4}$) carbon atoms, or 1 to 2 ($C_{1-2}$) carbon atoms. An alkyl moiety may be substituted or unsubstituted. This term includes, by way of example, linear and branched hydrocarbyl groups such as methyl (CH$_3$), ethyl (—CH$_2$CH$_3$), n-propyl (—CH$_2$CH$_2$CH$_3$), isopropyl (—CH(CH$_3$)$_2$), n-butyl (—CH$_2$CH$_2$CH$_2$CH$_3$), isobutyl (—CH$_2$CH(CH$_3$)$_2$), sec-butyl (—CH(CH$_3$)(CH$_2$CH$_3$), t-butyl (—C(CH$_3$)$_3$), n-pentyl (—CH$_2$CH$_2$CH$_2$CH$_2$CH$_3$), and neopentyl (—CH$_2$C(CH$_3$)$_3$).

"Amino" refers to the group —NH$_2$, —NHR, or —NRR, where each R independently is selected from H, aliphatic, aryl or heterocyclic, or two R groups together with the nitrogen attached thereto form a heterocyclic ring, which may be optionally substituted. Examples of such heterocyclic rings include those wherein two R groups together with the nitrogen to which they are attached form a —(CH$_2$)$_{2-5}$— ring optionally interrupted by one or two heteroatom groups, such as —O— or —N(R$^g$) such as in the groups

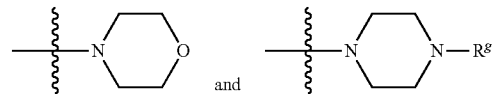

wherein $R^9$ is H, alkyl, —C(O)-alkyl, or —C(O)O-alkyl. A protected amino group is an amino group that is protected by a suitable protecting group, such as a protecting group defined herein.

"Aromatic" refers to a cyclic, conjugated group or moiety of, unless specified otherwise, from 5 to 15 ring atoms having a single ring (e.g., phenyl, pyridinyl, or pyrazolyl) or multiple condensed rings in which at least one ring is aromatic (e.g., naphthyl, indolyl, or pyrazolopyridinyl), that is at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example,

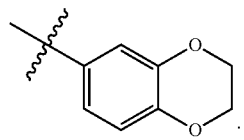 [SMILES: *c1ccc2c(c1)OCCO2]

However, in certain examples, context or express disclosure may indicate that the point of attachment is through a non-aromatic portion of the condensed ring system. For example

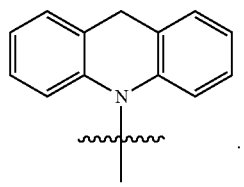 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si, preferably N, O or S), such as in a heteroaryl group or moiety. Unless otherwise stated, an aromatic group may be substituted or unsubstituted.

"Aryl" refers to an aromatic carbocyclic group of, unless specified otherwise, from 6 to 15 carbon atoms having a single ring (e.g., phenyl) or multiple condensed rings in which at least one ring is aromatic (e.g., 1,2,3,4-tetrahydroquinoline, benzodioxole, and the like) providing that the point of attachment is through an aromatic portion of the ring system. If any aromatic ring portion contains a heteroatom, the group is heteroaryl and not aryl. Aryl groups may be, for example, monocyclic, bicyclic, tricyclic or tetracyclic. Unless otherwise stated, an aryl group may be substituted or unsubstituted.

"Aralkyl" refers to an aryl group attached to the parent structure via an alkyl moiety. Exemplary aralkyl groups include benzyl and phenylethyl.

"Carboxylic acid" refers to the group —COOH.

"Carboxylic ester" refers to the group —COOR, where R is aliphatic, aryl, heterocyclyl, typically alkyl.

"Cycloaliphatic" refers to a cyclic aliphatic group having a single ring (e.g., cyclohexyl), or multiple rings, such as in a fused, bridged or spirocyclic system, at least one of which is aliphatic, provided that the point of attachment is through an atom of an aliphatic region of the cycloaliphatic group. Cycloaliphatic includes saturated and unsaturated systems, including cycloalkyl, cycloalkenyl and cycloalkynyl. Exemplary cycloaliphatic groups include, but are not limited to, cyclopropyl, cyclobutyl, cyclopentyl, cyclohexyl, cycloheptyl, cyclopentenyl, or cyclohexenyl.

"Cycloalkylalkyl" refers to a cycloalkyl group attached to the parent structure via an acyclic alkyl moiety. Exemplary cycloalkylalkyl groups include cyclohexylmethylene and cyclohexylethylene.

"Halo," "halide" or "halogen" refers to fluoro, chloro, bromo or iodo.

"Haloalkyl" refers to an alkyl moiety substituted with one or more halogens. Exemplary haloalkyl moieties include —CH$_2$F, —CHF$_2$ and —CF$_3$.

"Heteroaryl" refers to an aromatic group or moiety of, unless specified otherwise, from 5 to 15 ring atoms comprising at least one carbon atom and at least one heteroatom, such as N, S, or O. A heteroaryl group or moiety may comprise a single ring (e.g., pyridinyl, pyrimidinyl or imidazolyl) or multiple condensed rings (e.g., indolyl or benzimidazolyl). Heteroaryl groups or moiety may be, for example, monocyclic, bicyclic, tricyclic or tetracyclic. Unless otherwise stated, a heteroaryl group or moiety may be substituted or unsubstituted.

"Heterocyclyl," "heterocyclo" and "heterocycle" refer to both aromatic and non-aromatic ring systems, and more specifically refer to a stable three- to fifteen-membered ring moiety comprising at least one carbon atom, and typically plural carbon atoms, and at least one, such as from one to five, heteroatoms. The heteroatom(s) may be nitrogen, oxygen, sulfur, phosphorus, or silicon atom(s), preferably nitrogen, oxygen, or sulfur atom(s). The heterocyclyl moiety may be a monocyclic moiety, or may comprise multiple rings, such as in a bicyclic or tricyclic ring system, provided that at least one of the rings contains a heteroatom. Such a multiple ring moiety can include fused or bridged ring systems as well as spirocyclic systems, and may include all aromatic, all non-aromatic, or both aromatic and non-aromatic rings. Also, any nitrogen, carbon, or sulfur atoms in the heterocyclyl moiety can be optionally oxidized to various oxidation states. For convenience, nitrogens, particularly, but not exclusively, those defined as annular aromatic nitrogens, are meant to include their corresponding N-oxide form, although not explicitly defined as such in a particular example. Thus, for a compound having, for example, a pyridinyl ring, the corresponding pyridinyl-N-oxide is included as another compound of the invention, unless expressly excluded or excluded by context. In addition, annular nitrogen atoms can be optionally quaternized. Heterocycle includes heteroaryl moieties, and non-aromatic heterocyclyl moieties, also called heterocycloaliphatic moieties, which may be partially or fully saturated rings. Examples of heterocyclyl groups include, but are not limited to, azetidinyl, oxetanyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, diazabicycloheptane, diazapane, diazepine, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Hydroxyl" refers to the group —OH. A protected hydroxyl group is a hydroxyl group protected by a protecting group, such as in —O-PG. PG can be any suitable protecting group known to a person of ordinary skill in the art, including but not limited to, protecting groups specifically disclosed herein.

"Hydroxyalkyl" refers to an alkyl moiety substituted with one or more hydroxyl groups. A protected hydroxyalkyl is a hydroxyalkyl where at least one hydroxyl moiety is protected by a protecting group (PG), such as a protecting group disclosed herein. Exemplary hydroxyalkyl moieties include —CH$_2$OH, —CH$_2$CH$_2$OH, —CH(OH)CH$_3$,

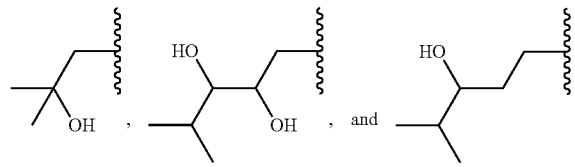

"Effective amount" refers to an amount sufficient to provide a beneficial, or desired, effect to a subject or a given percentage of subjects. The beneficial or desired effect may include inhibiting a protein or enzyme; eliciting a desired biological or medical response in a tissue, system, subject or patient; treating a specified disorder or disease; ameliorating or eradicating one or more of symptoms of a disease or disorder; and/or preventing the occurrence of a disease or disorder. An appropriate "effective" amount in any individual case can be determined using any suitable technique, such as a dose escalation study.

"Pharmaceutically acceptable salt: refers to a biologically compatible salt of a compound that can be used as a drug, which salts are derived from a variety of organic and inorganic counter ions well known in the art. Pharmaceutically acceptable salts include salts of organic or inorganic acids, such as hydrochloride, hydrobromide, tartrate, mesylate, acetate, maleate, oxalate, sulfate, nitrate, phosphate, formate, trifluoroactate, glycolate, citrate, tosylate, and the like. If the molecule contains an acidic functionality, pharmaceutically acceptable salts may include, by way of example only, sodium, potassium, calcium, magnesium, ammonium, tetraalkylammonium, and the like.

"Pharmaceutically acceptable excipient" refers to a substantially physiologically inert substance that is used as an additive in a pharmaceutical composition. As used herein, an excipient may be incorporated within particles of a pharmaceutical composition, or it may be physically mixed with particles of a pharmaceutical composition. An excipient can be used, for example, as a carrier, flavoring, thickener, diluent, buffer, preservative, or surface active agent and/or to modify properties of a pharmaceutical composition. Examples of excipients include, but are not limited, to polyvinylpyrrolidone (PVP), tocopheryl polyethylene glycol 1000 succinate (also known as vitamin E TPGS, or TPGS), dipalmitoyl phosphatidyl choline (DPPC), trehalose, sodium bicarbonate, glycine, sodium citrate, and lactose.

"Protecting group" refers to any protecting group known to a person of ordinary skill in the art as suitable to protect a particular moiety, such as a hydroxyl or amino moiety. Suitable protecting groups, and methods for attaching and removing such groups, are known to persons of ordinary skill in the art, and additional information concerning such groups can be found in Greene, *Protective Groups in Organic Synthesis;* 4th Ed.; John Wiley & Sons, New York, 2014, which is incorporated herein by reference. Exemplary protecting groups include, but are not limited to, acetate, chloroacetate, dichloroacetate, trichloroacteate, trifluoroacetate, pivaloate, benzoate, p-methoxybenzoate, p-bromobenzoate, methyl carbonate, 9-(fluorenylmethyl) carbonate (Fmoc), allyl carbonate, benzyl carbonate (CBZ), t-butyl carbonate (Boc), dimethylthiocarbonate (DMTC), methoxymethyl (MOM), tert-butyl, iso-propyl, and silyl protecting groups, such as tert-butyldimethylsilyl (TBS or TBDMS), trimethylsilyl (TMS), triethylsilyl (TES), tert-butyldiphenylsilyl (TBDPS), or triisopropylsilyl (TIPS).

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. The compounds described herein can exist in un-solvated as well as solvated forms when combined with solvents, pharmaceutically acceptable or not, such as water, ethanol, and the like. When a compound forms a solvate with water it may be referred to as a hydrate. Solvated forms of the presently disclosed compounds are within the scope of the embodiments disclosed herein.

Particular examples of the presently disclosed compounds may include one or more asymmetric centers; thus these compounds can exist in different stereoisomeric forms. Accordingly, compounds and compositions may be provided as individual pure enantiomers or diasteriomers, or as stereoisomeric mixtures, including racemic mixtures. In certain embodiments the compounds disclosed herein are synthesized in or are purified to be in substantially enantiopure form, such as in an 85% enantiomeric excess (e.e.), a 90% enantiomeric excess, a 95% enantiomeric excess, a 97% enantiomeric excess, a 98% enantiomeric excess, a 99% enantiomeric excess, or even in greater than a 99% enantiomeric excess, such as in a substantially enantiopure form.

A person of ordinary skill in the art understands that in a compound comprising one or more asymmetric centers, one or both enantiomers or diastereomers are contemplated unless a specific enantiomer or diastereomer is shown or described. For example, a

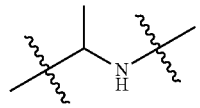 [SMILES: *NC(*)C]

moiety contemplates

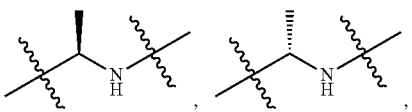

or a mixture thereof, such as a racemic mixture.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a hydroxyl, amino, and/or phosphonate group functionalized with any group that is cleaved in vivo to yield the corresponding hydroxyl, amino and/or phosphonate group, respectively. Examples of prodrugs include, without limitation, compounds having an acylated hydroxyl group, an acylated amino group, an ascorbate moiety, an ortho ester, an imidate group, a phosphonate ester or phosphonate amide group.

In any embodiments, any or all hydrogens present in the compound, or in a particular group or moiety within the compound, may be replaced by a deuterium or a tritium. Thus, a recitation of alkyl includes deuterated alkyl, where from one to the maximum number of hydrogens present may be replaced by deuterium. For example, ethyl may be $C_2H_5$ or $C_2H_5$ where from 1 to 5 hydrogens are replaced by deuterium, such as in $C_2D_xH_{5-x}$. In certain embodiments, a deuterated compound comprises an amount of deuterium at a specified position that is greater than an amount of deuterium that might be present at that position due to the natural abundance of deuterium had the compound been a natural product rather than synthetically produced.

II. Compounds

Disclosed herein are compound having a Formula I

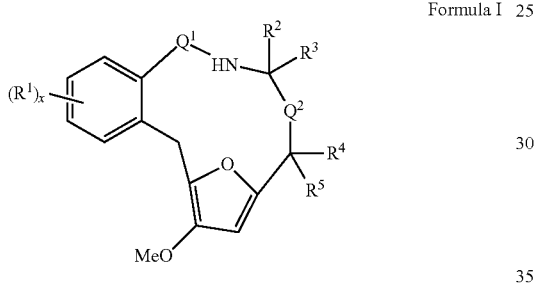

Formula I or a salt, solvate, N-oxide, prodrug, diastereomer or enantiomer thereof. With respect to Formula I, x is from 0 to 4, such as 0, 1, 2, 3, or 4, and if present, each $R^1$ independently is hydroxyl; halogen, such as F, Br, Cl, or I; aliphatic, such as alkyl, alkenyl, or alkynyl, preferably $C_{1-6}$alkyl, $C_{1-4}$alkyl, or $C_{1-2}$alkyl; alkoxy, such as $C_{1-6}$alkoxy, $C_{1-4}$alkoxy or $C_{1-2}$alkoxy; haloalkyl, such as $C_{1-6}$haloalkyl, $C_{1-4}$haloalkyl, or $C_{1-2}$haloalkyl, and may comprise from 1 to 3 or more halogens, from F, Cl, Br, or I, preferably F; amino; protected amino; carboxylic ester; and/or two $R^1$s, together with the atoms to which they are attached, form an aryl or heterocyclyl. Such as aryl or heterocyclyl may be unsubstituted or substituted, such as substituted with one or more substituents, typically, 1, 2, 3 or 4 substituents, that may be selected from halogen, =O, or aliphatic, such as alkyl. In some embodiments, each $R^1$ independently is hydroxy; halogen, selected from F, Br, or Cl; $C_{1-4}$alkyl, preferably methyl, ethyl, propyl, isopropyl or tert-butyl; $C_{1-4}$alkoxy, preferably, methoxy, ethoxy, propoxy, isopropoxy or cyclopropoxy; haloalkyl, $C_{1-2}$haloalkyl, such as $CF_3$; and/or two R's, together with the atoms to which they are attached, form a phenyl or a 5- or 6-membered heterocyclyl, such as 5- or 6-membered heteroaryl, or 5- or 6-membered non-aromatic heterocyclyl, any of which may be optionally substituted as previously described. The 5- or 6-membered heteroaryl may be pyridinyl, imidazolyl, pyrazolyl, pyrrolyl, oxazolyl, thiazolyl, furanyl, or thiophenyl. The 5- or 6-membered non-aromatic heterocyclyl may be 1,3-dioxole, 1,4-dioxine, 2,3-dihydro-1,4-dioxine, 1,4-oxazine, or 3,4-dihydro-1,4-oxazine. In particular embodiments, the moiety is

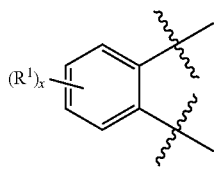

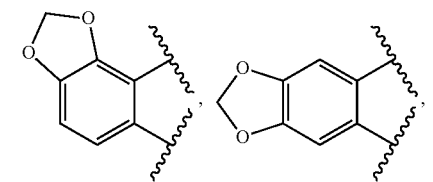

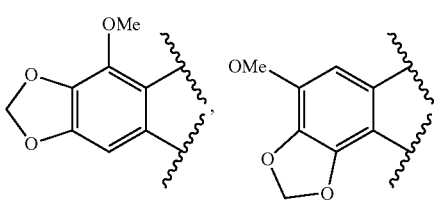

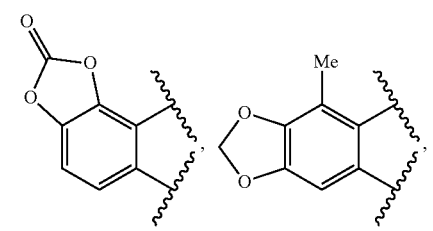

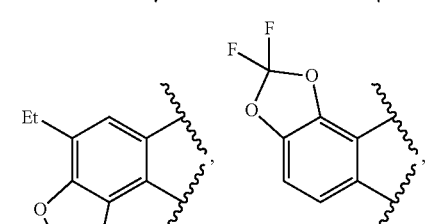

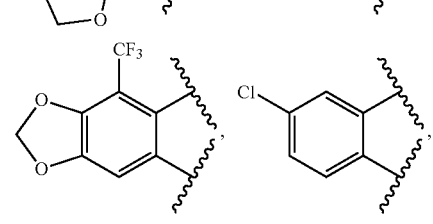

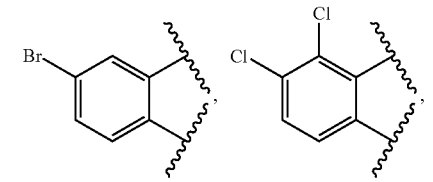

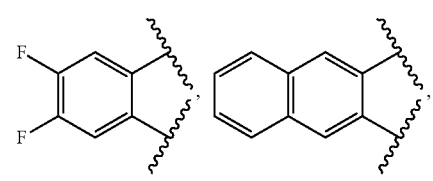

-continued

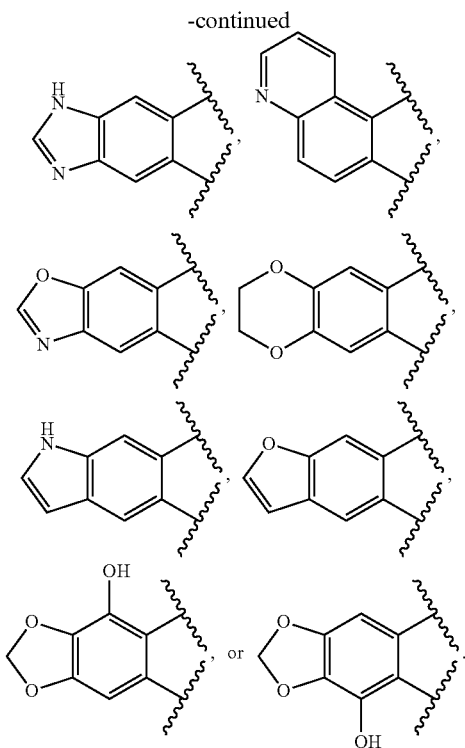

In certain embodiments, the

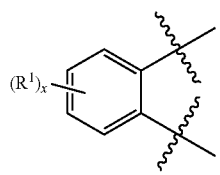

moiety is

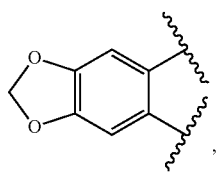 [SMILES: *c1cc2c(cc1*)OCO2]

but in other embodiments, the

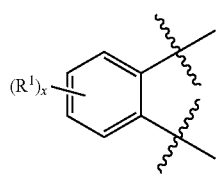

moiety is not

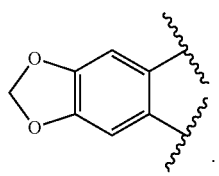 [SMILES: *c1cc2c(cc1*)OCO2]

Each of $Q^1$ and $Q^2$ independently is aliphatic, such as alkyl, alkenyl, or alkynyl, preferably alkyl, such as $C_{1-2}$alkyl, and may be unsubstituted or substituted with 1 or more substituents, such as 1, 2, 3, or 4 substituents. In some embodiments, $Q^1$ and/or $Q^2$ is substituted with halogen, such as F, Br, Cl, or I; aliphatic, such as alkyl, typically $C_{1-6}$alkyl, $C_{1-4}$alkyl or $C_{1-2}$alkyl; hydroxyalkyl, such as $C_{1-4}$hydroxyalkyl or $C_{1-3}$hydroxyalkyl, or a protected hydroxyalkyl, such as protected $C_{1-4}$hydroxyalkyl or protected $C_{1-3}$hydroxyalkyl; =O; =S; aryl, such as phenyl, which may be optionally substituted; heteroaryl, such as 5- or 6-membered heteroaryl, which may be optionally substituted; hydroxyl; protected hydroxyl; haloalkyl, such as —$CF_3$; carboxylic ester; amino; protected amino; or any combination thereof.

In some embodiments, $Q^1$ is $C_{1-2}$alkyl and may be unsubstituted, such as —$CH_2$— or —$CH_2CH_2$—, or substituted with 1, 2, 3, or 4 substituents from halogen, alkyl, hydroxyalkyl, protected hydroxyalkyl, =O, =S, aryl, hydroxyl, protected hydroxyl, haloalkyl, carboxylic ester, amino, protected amino, or a combination thereof. In certain embodiments, $Q^1$ is substituted with $C_{1-4}$alkyl, preferably methyl, ethyl, propyl, isopropyl; hydroxyl; protected hydroxyl; $C_{1-4}$hydroxyalkyl or a protected $C_{1-4}$hydroxyalkyl, and may be hydroxyethyl, hydroxypropyl, or a protected derivative thereof; phenyl; =O; =S; or a combination thereof.

In particular embodiments, $Q^1$ is $C_1$alkyl, and may be unsubstituted or substituted with $C_{1-4}$alkyl, such as $C_{1-2}$alkyl, preferably methyl, or ethyl; $C_{1-4}$hydroxyalkyl or a protected $C_{1-4}$hydroxyalkyl, and may be hydroxyethyl, hydroxypropyl, or a protected derivative thereof; phenyl; hydroxyl; protected hydroxyl; or a combination thereof.

In other embodiments, $Q^1$ is $C_2$alkyl, and may be unsubstituted or substituted with $C_{1-4}$alkyl, such as $C_{1-2}$alkyl, preferably methyl, or ethyl; $C_{1-4}$hydroxyalkyl or a protected $C_{1-4}$hydroxyalkyl, and may be hydroxyethyl, hydroxypropyl, or a protected derivative thereof; phenyl; hydroxyl; protected hydroxyl; =O; =S, or a combination thereof. And in certain embodiments, $Q^1$ is not an unsubstituted $C_2$alkyl.

In some embodiments, the

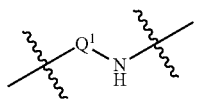

moiety is

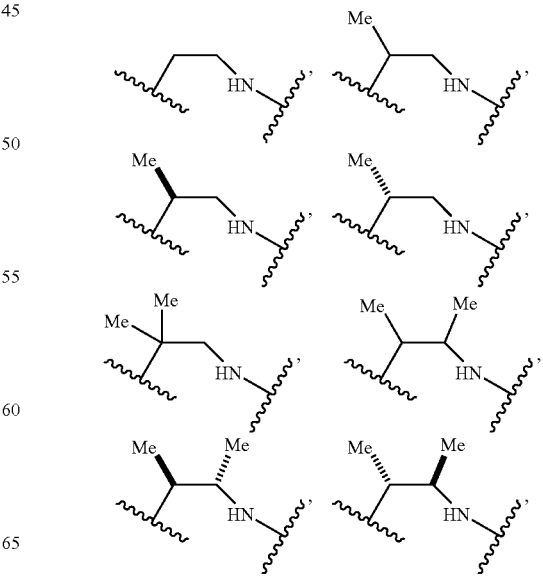

-continued

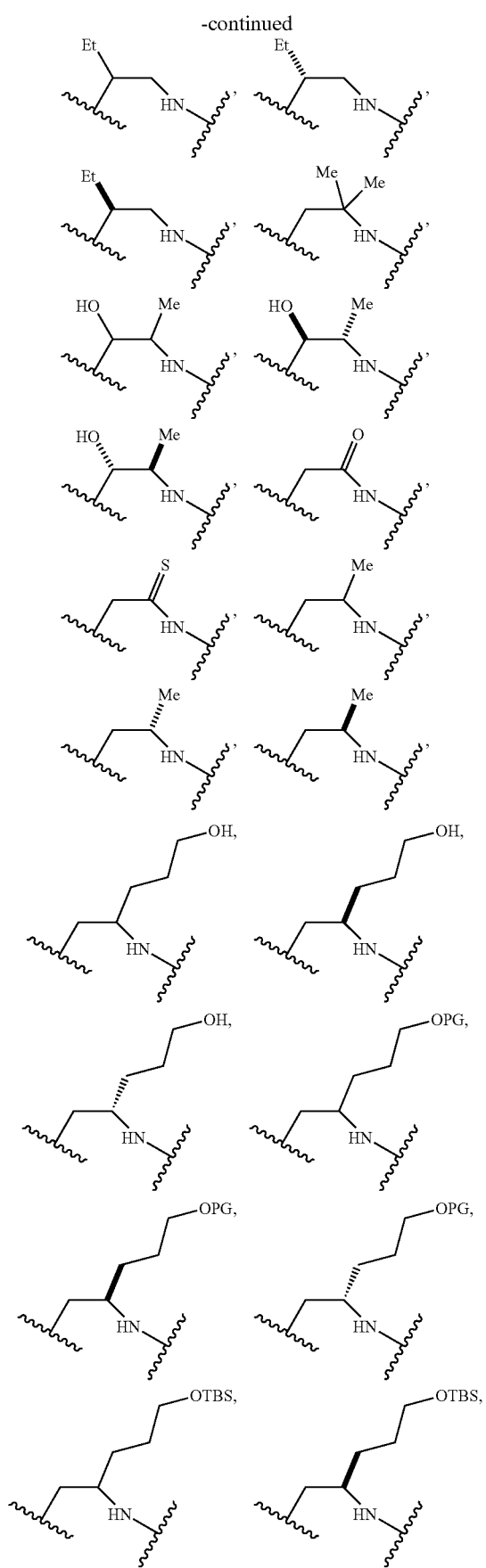

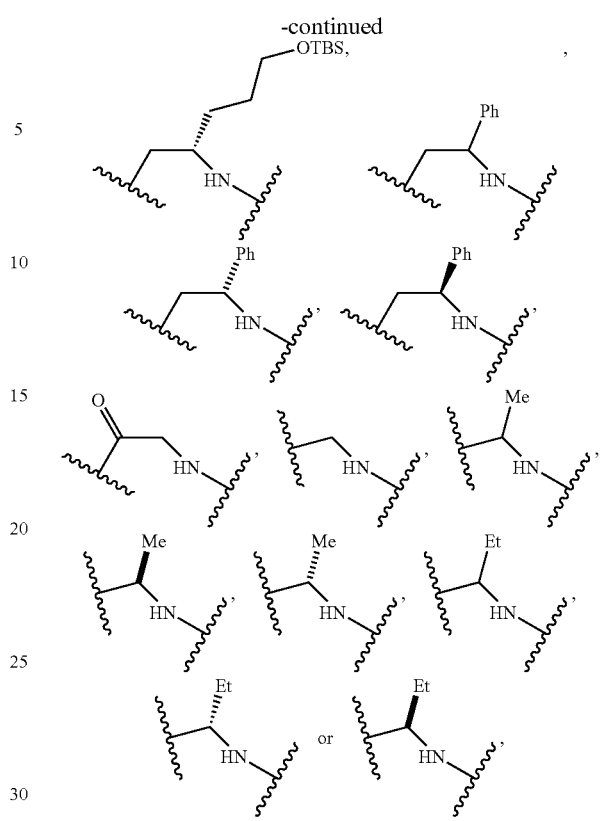

wherein PG is a hydroxyl protecting group as defined herein, and/or known to a person of ordinary skill in the art. In certain embodiments, the

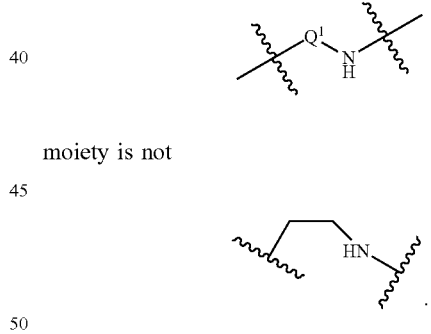

moiety is not

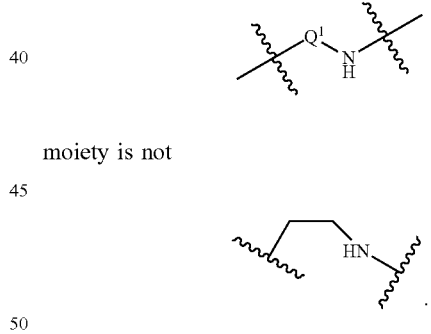

In any of the above embodiments, $Q^2$ is $C_{1-2}$alkyl and may be unsubstituted, such as —$CH_2$— or —$CH_2CH_2$—, or substituted with 1, 2, 3, or 4 substituents selected from halogen, alkyl, hydroxyalkyl, protected hydroxyalkyl, =O, =S, aryl, hydroxyl, protected hydroxyl, haloalkyl, carboxylic ester, amino, protected amino, or a combination thereof. In some embodiments, $Q^2$ is unsubstituted, but in other embodiments, $Q^2$ is substituted with $C_{1-4}$alkyl, preferably methyl, ethyl, propyl, isopropyl; $C_{1-4}$hydroxyalkyl or a protected $C_{1-4}$hydroxyalkyl, and may be hydroxyethyl, hydroxypropyl, or a protected derivative thereof, hydroxyl; protected hydroxyl; =O; =S; or a combination thereof. In particular embodiments, $Q^2$ is $C_2$alkyl, and may be unsubstituted or substituted with halogen, such as F, Cl, Br, or I, preferably Cl; $C_{1-4}$alkyl, such as $C_{1-2}$alkyl, preferably methyl, or ethyl; $C_{1-4}$hydroxyalkyl or a protected $C_{1-4}$hydroxyalkyl, and may be hydroxyethyl, hydroxypropyl, or a protected derivative thereof, hydroxyl; protected hydroxyl; or a combination thereof. In other embodiments, $Q^1$ is $C_1$alkyl, and may be unsubstituted or substituted with halogen, such as F, Cl, Br, or I, preferably Cl; $C_{1-4}$alkyl, such as $C_{1-2}$alkyl, preferably methyl, or ethyl; $C_{1-4}$hydroxyalkyl or a protected $C_{1-4}$hydroxyalkyl, and may be hydroxyethyl, hydroxypropyl, or a protected derivative thereof, =O; =S; hydroxyl; protected hydroxyl; or a combination thereof.

In any of the above embodiments, each of $R^2$, $R^3$, $R^4$ and $R^5$ independently may be H; halogen, such as F, Br, Cl, or I; aliphatic, such as alkyl, alkenyl or alkynyl, preferably alkyl, such as $C_{1-6}$alkyl, $C_{1-4}$alkyl or $C_{1-2}$alkyl; hydroxyalkyl, such as $C_{1-4}$hydroxyalkyl or $C_{1-3}$hydroxyalkyl, or a protected hydroxyalkyl, such as protected $C_{1-4}$hydroxyalkyl or protected $C_{1-3}$hydroxyalkyl; aryl, such as phenyl, which may be optionally substituted; heteroaryl, such as 5- or 6-membered heteroaryl, which may be optionally substituted; hydroxyl; or protected hydroxyl; haloalkyl, such as —$CF_3$; carboxylic ester; amino; protected amino; or two of $R^2$, $R^3$, $R^4$ and $R^5$ that are attached to the same carbon together form =O or =S, that is either $R^2$ and $R^3$ together form =O or =S, and/or $R^4$ and $R^5$ together form =O or =S.

With respect to protected hydroxyl, protected hydroxyalkyl, and protected amino moieties disclosed herein, the protecting group may be any protecting group known to a person of ordinary skill in the art as suitable to protect a hydroxyl or amino moiety. Exemplary protecting groups include, but are not limited to, acetate, chloroacetate, dichloroacetate, trichloroacteate, trifluoroacetate, pivaloate, benzoate, p-methoxybenzoate, p-bromobenzoate, methyl carbonate, 9-(fluorenylmethyl) carbonate (Fmoc), allyl carbonate, benzyl carbonate (CBZ), t-butyl carbonate (Boc), dimethylthiocarbonate (DMTC), methoxymethyl (MOM), tert-butyl, iso-propyl, and silyl protecting groups, such as tert-butyldimethylsilyl (TBS or TBDMS), trimethylsilyl (TMS), triethylsilyl (TES), tert-butyldiphenylsilyl (TBDPS), or triisopropylsilyl (TIPS). In certain embodiments, a protected hydroxyl and/or a protected hydroxyalkyl comprises a silyl protecting group, such as TBS.

And in some embodiments, if $R^2$, $R^3$, $R^4$ and $R^5$ are all hydrogen then $Q^2$ is not an unsubstituted $C_1$alkyl.

In exemplary embodiments, the

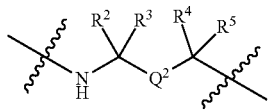

moiety is

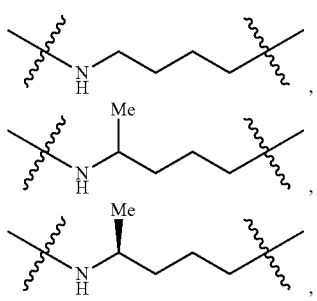

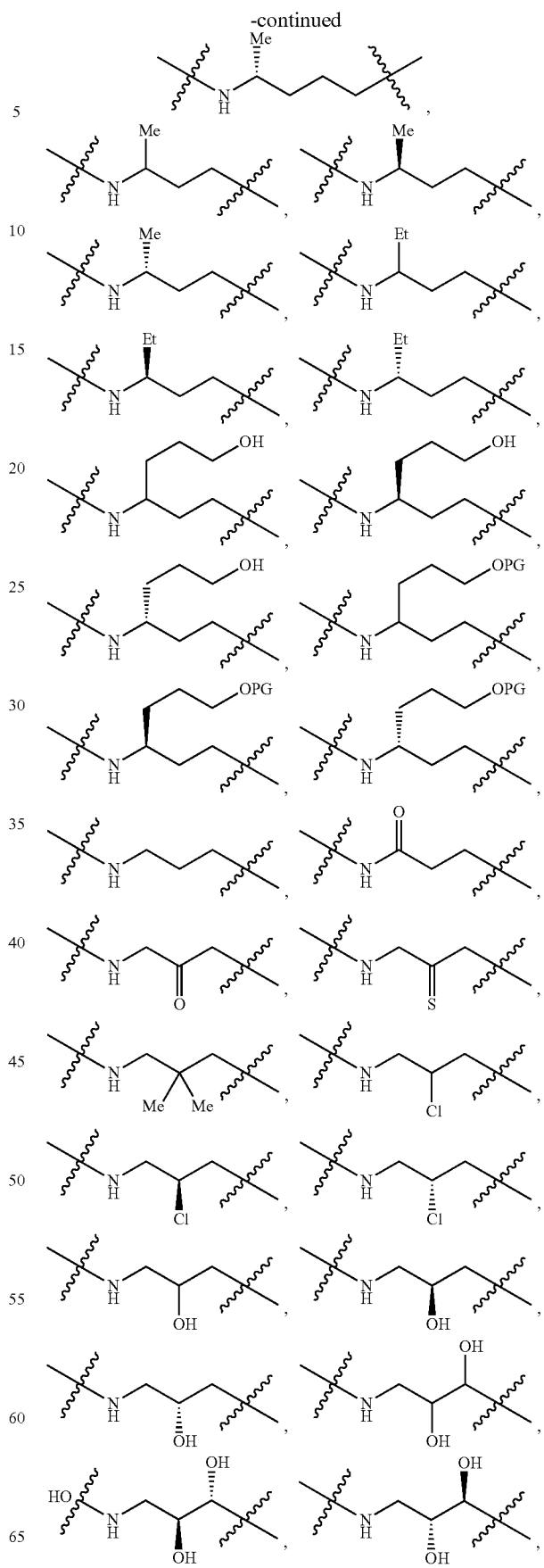

-continued

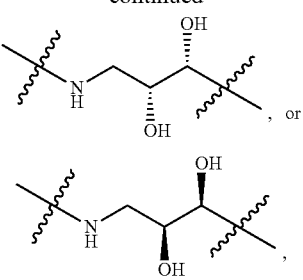, or

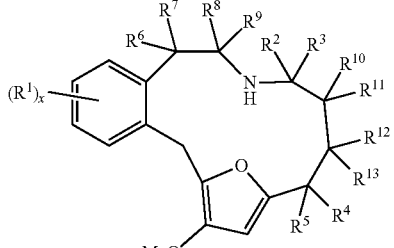

Formula I-c

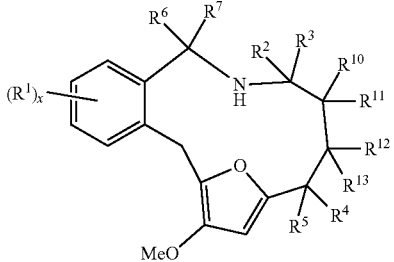

Formula I-d wherein PG is a hydroxyl protecting group as defined herein, and/or known to a person of ordinary skill in the art. In certain embodiments, the

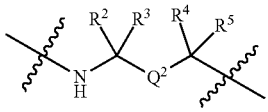

moiety is not

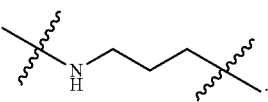 [SMILES: *CCCN*].

In one embodiment, $Q^1$ is $C_1$alkyl and $Q^2$ is $C_1$alkyl.
In one embodiment, $Q^1$ is $C_1$alkyl and $Q^2$ is $C_2$alkyl.
In one embodiment, $Q^1$ is $C_2$alkyl and $Q^2$ is $C_1$alkyl.
In one embodiment, $Q^1$ is $C_2$alkyl and $Q^2$ is $C_2$alkyl.

In some embodiments, compounds accordingly to Formula I have a formula selected from Formulas I-a, I-b, I-c, I-d, or a salt, solvate, N-oxide, prodrug, diastereomer or enantiomer thereof.

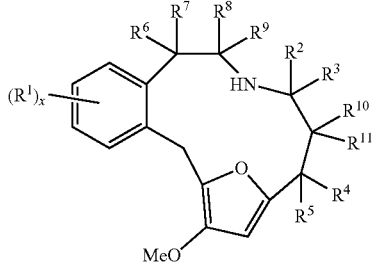

Formula I-a

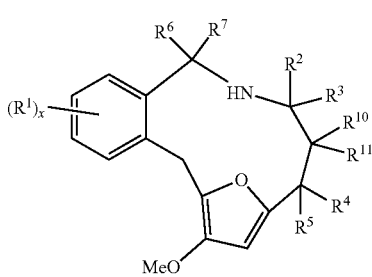

Formula I-b

With respect to Formulas I-a, I-b, I-c, and I-d, x, $R^1$, $R^2$, $R^3$, $R^4$, and $R^5$ are as previously defined for Formula I. Each of $R^6$-$R^9$ independently is H; halogen, such as F, Br, Cl, or I; aliphatic, such as alkyl, alkenyl or alkynyl, preferably alkyl, such as $C_{1-6}$alkyl, $C_{1-4}$alkyl or $C_{1-2}$alkyl; hydroxyalkyl, such as $C_{1-4}$hydroxyalkyl or $C_{1-3}$hydroxyalkyl, or a protected hydroxyalkyl, such as protected $C_{1-4}$hydroxyalkyl or protected $C_{1-3}$hydroxyalkyl; aryl, such as phenyl, which may be optionally substituted; heteroaryl, such as 5- or 6-membered heteroaryl, which may be optionally substituted; hydroxyl; protected hydroxyl; haloalkyl, such as —$CF_3$; carboxylic ester; amino; protected amino; or two of $R^6$, $R^7$, $R^8$ and $R^9$ that are attached to the same carbon together form =O or =S, that is $R^6$ and $R^7$ together form =O or =S, or $R^8$ and $R^9$ together form =O or =S; or any combination thereof.

Each of $R^6$-$R^9$ independently, if present, may be H; $C_{1-4}$alkyl, preferably methyl, ethyl, propyl, isopropyl, more preferably $C_{1-2}$alkyl, such as methyl or ethyl; hydroxyl; protected hydroxyl; $C_{1-4}$hydroxyalkyl or a protected $C_{1-4}$hydroxyalkyl, and may be hydroxyethyl, hydroxypropyl, or a protected derivative thereof, phenyl; or two of $R^6$, $R^7$, $R^8$ and $R^9$ that are attached to the same carbon together form =O or =S; or any combination thereof.

In some embodiments, each of $R^6$-$R^9$, if present, is H, but in other embodiments, at least one of $R^6$-$R^9$ is not H.

And if present, each of $R^{10}$-$R^{13}$ independently is H, halogen, aliphatic, such as alkyl, alkenyl or alkynyl, preferably alkyl, hydroxyalkyl, protected hydroxyalkyl, optionally substituted aryl, hydroxyl, protected hydroxyl, haloalkyl, such as —$CF_3$, carboxylic ester, amino, protected amino, or two of $R^{10}$, $R^{11}$, $R^{12}$ and $R^{13}$ that are attached to the same carbon together form =O or =S, that is $R^{10}$ and $R^{11}$ together form =O or =S, or $R^{12}$ and $R^{13}$ together form =O or =S, or a combination thereof. In some embodiments, each of $R^{10}$-$R^{13}$ independently is H; halogen, such as F, Cl, Br, or I, preferably Cl; $C_{1-4}$alkyl, such as $C_{1-2}$alkyl, preferably methyl, ethyl; $C_{1-4}$hydroxyalkyl or a protected $C_{1-4}$hydroxyalkyl, and may be hydroxyethyl, hydroxypropyl, or a protected derivative thereof, hydroxyl; protected hydroxyl; or $R^{10}$ and $R^{11}$ together form =O or =S; or $R^{12}$ and $R^{13}$ together form =O or =S; or a combination thereof.

In some embodiments, each of $R^{10}$-$R^{13}$, if present, is H, but in other embodiments, at least one of $R^{10}$-$R^{13}$ is not H.

Also disclosed herein are compounds having a Formula II, Formula III or Formula IV, or a salt, solvate, N-oxide, prodrug, diastereomer or enantiomer thereof.

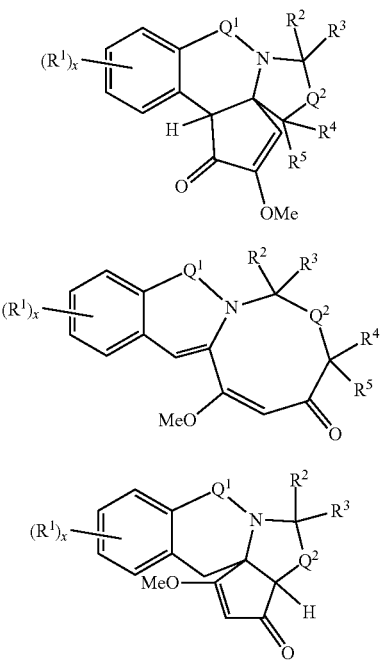

Formula II

Formula III

Formula IV

A person of ordinary skill in the art understand that a compound of Formula II may have a structure according to Formula II-1 or Formula II-2, or a combination thereof, such as a racemic mixture of Formulas II-1 and II-2. For brevity, in the following formulas, the fused ring system is shown with the specific orientation illustrated by Formula II-1. However, a person of ordinary skill in the art will understand that the isomer shown in Formula II-2 also is contemplated, as are mixtures of the two isomers, including racemic mixtures.

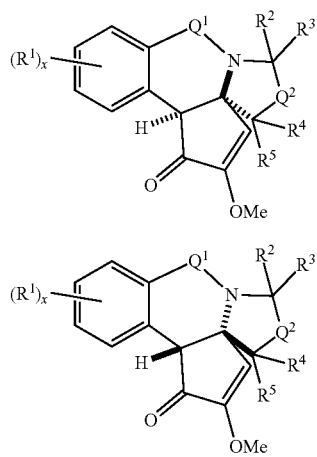

Formula II-1

Formula II-2

Similarly, a compound of Formula IV may have a structure according to Formula VI-1 or Formula IV-2, or a combination thereof, such as a racemic mixture.

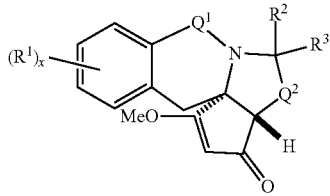

Formula IV-1

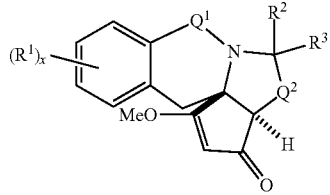

Formula IV-2

With respect to Formulas II, II-1, II-2, III, IV, IV-1, and IV-2, x, $R^1$, $R^2$, $R^3$, $R^4$, $R^5$, $Q^1$ and $Q^2$ are as previously defined for Formula I. In some embodiments, the compound according to Formula II is not

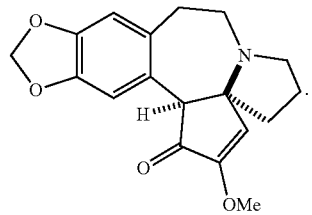

Compounds according to Formula II may have a formula selected from Formulas II-a, II-b, II-c, or II-d, or a salt, solvate, N-oxide, prodrug, diastereomer or enantiomer thereof.

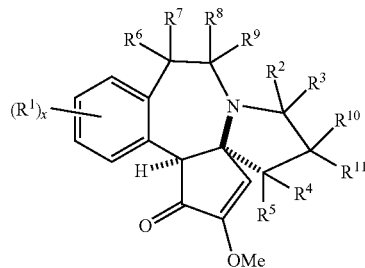

Formula II-a

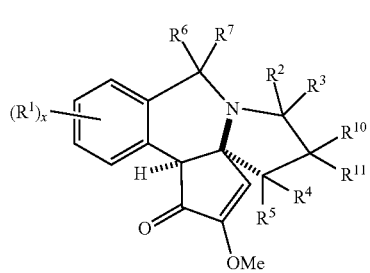

Formula II-b

Formula II-c

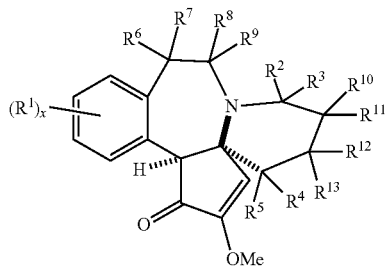

Formula II-d

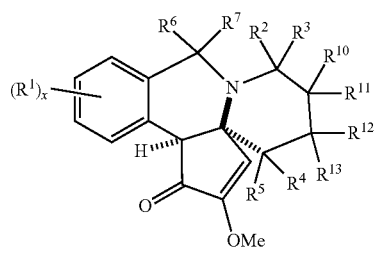

With respect to Formulas II-a, II-b, II-c, and II-d, x, and $R^1$-$R^{13}$ are as previously defined for Formulas I-a to I-d. In some embodiments, the compound according to Formula II-a is not

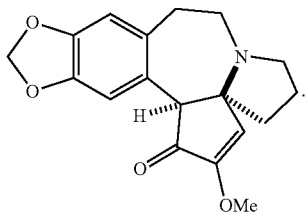

Compounds according to Formula III may have a formula selected from Formulas III-a, III-b, III-c, or III-d, or a salt, solvate, N-oxide, prodrug, diastereomer or enantiomer thereof.

Formula III-a

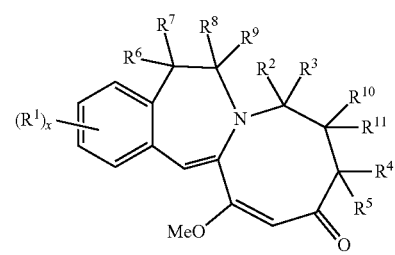

Formula III-b

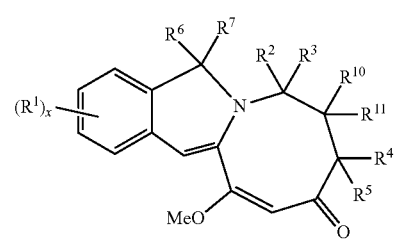

Formula III-c

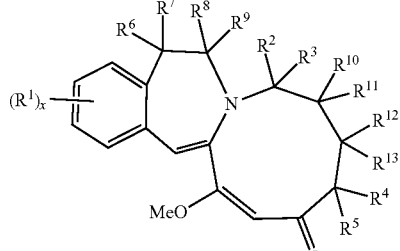

Formula III-d

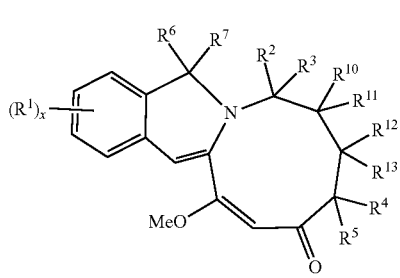

With respect to Formulas III-a, III-b, III-c, and III-d, x, and $R^1$-$R^3$ are as previously defined for Formulas I-a to I-d.

Compounds according to Formula IV may have a formula selected from Formulas IV-a, IV-b, IV-c, or IV-d, or a salt, solvate, N-oxide, prodrug, diastereomer or enantiomer thereof.

Formula IV-a

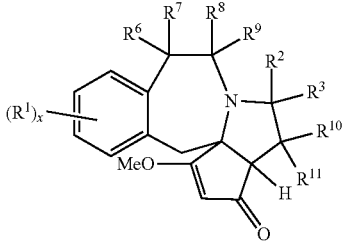

Formula IV-b

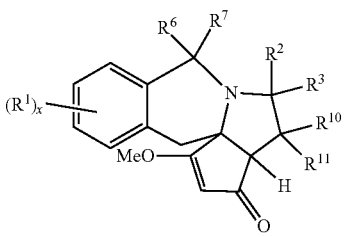

Formula IV-c

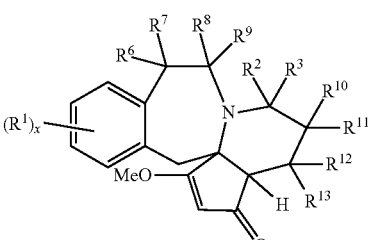

-continued

Formula IV-d

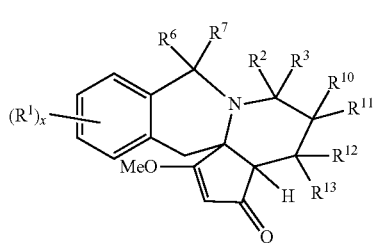

With respect to Formulas IV-a, IV-b, IV-c, and IV-d, x, and $R^1$-$R^{13}$ are as previously defined for Formulas I-a to I-d.

Further disclosed are compounds having a Formula V-1, V-2 or V-3, or a salt, solvate, N-oxide, prodrug, diastereomer or enantiomer thereof.

Formula V-1

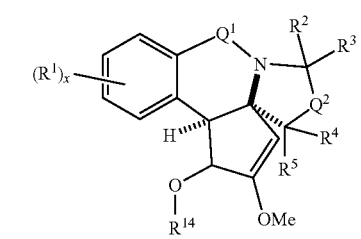

Formula V-2

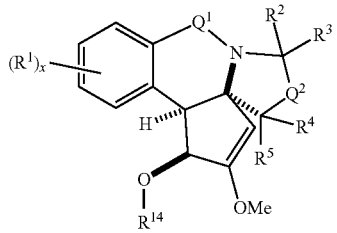

Formula V-3

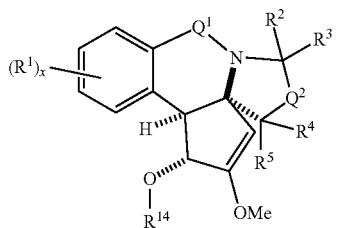

With respect to Formulas V-1, V-2 and V-3, x, $R^1$, $R^2$, $R^3$, $R^4$, $R^5$, $Q^1$ and $Q^2$ are as previously defined for Formula I, and $R^{14}$ is H; aliphatic, such as $C_{1-10}$aliphatic, typically, $C_{1-10}$alkyl or $C_{2-10}$alkenyl; acyl, such as $C_{1-10}$acyl; aryl, such as phenyl, which may be optionally substituted; or heterocyclyl, such as 5- or 6-memebered heterocyclyl, and may be optionally substituted. In some embodiments, $R^{14}$ is H, but in other embodiments, $R^{14}$ is not H, that is $R^{14}$ is aliphatic, such as $C_{1-10}$aliphatic, typically, $C_{1-10}$alkyl or $C_{2-10}$alkenyl; acyl, such as $C_{1-10}$acyl; aryl, such as phenyl; or heterocyclyl, such as 5- or 6-memebered heterocyclyl. In some embodiments, $R^{14}$ is other than H and is substituted with at least a hydroxyl, such as 1, 2, or 3 hydroxyl moieties. In certain embodiments, $R^{14}$ is $C_{1-10}$acyl, optionally substituted with hydroxyl, alkyl, aralkyl, cycloalkylalkyl, hydroxyalkyl, carboxylic ester, carboxylic acid, —$CH_2$-carboxylic ester, or a combination thereof. And in certain embodiments where $R^{14}$ comprises one or more chiral centers, the R or S enantiomer of each chiral center is contemplated, as well as a racemic mixture of enantiomers or diastereomers.

In some embodiments, $R^{14}$ is

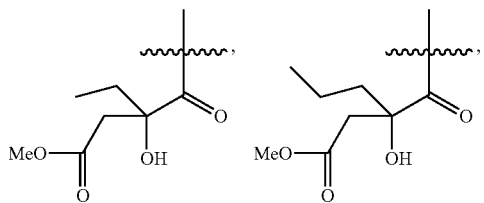

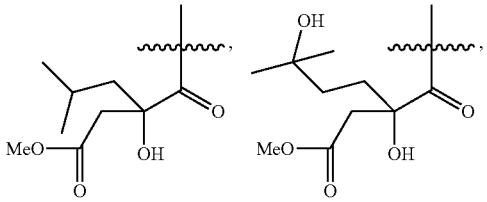

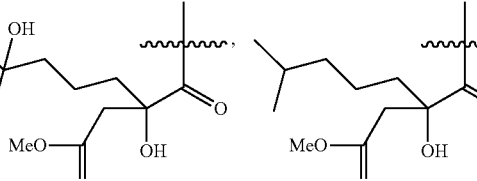

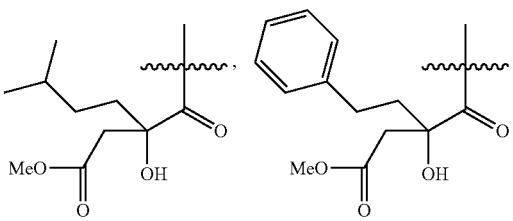

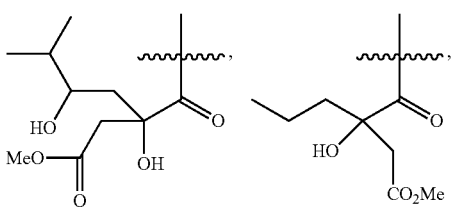

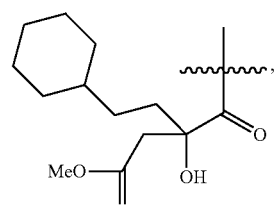

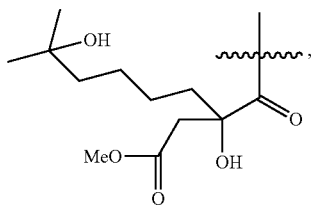

33
-continued
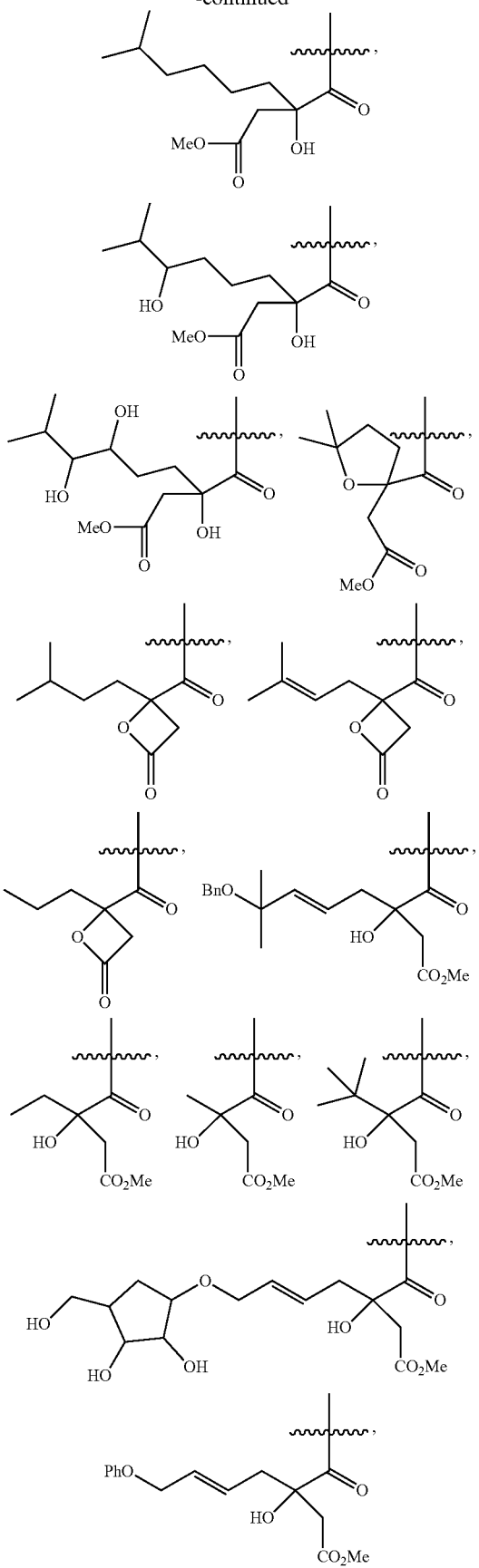
34
-continued
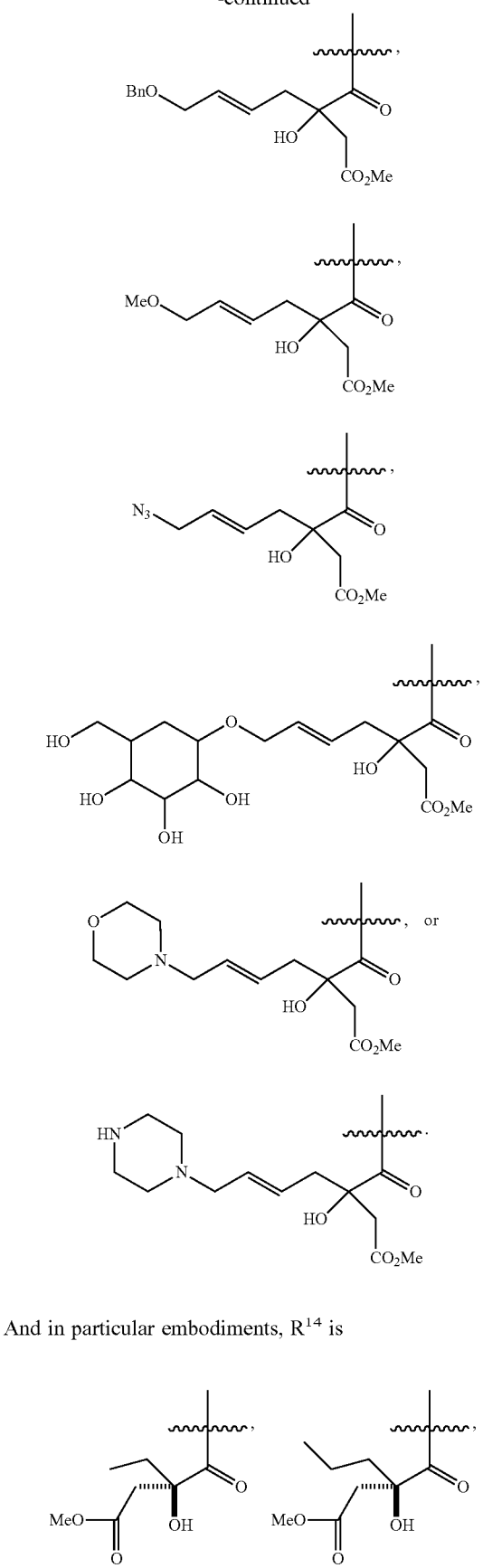
And in particular embodiments, $R^{14}$ is
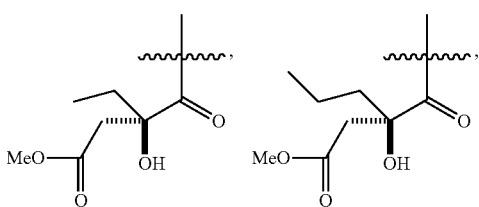

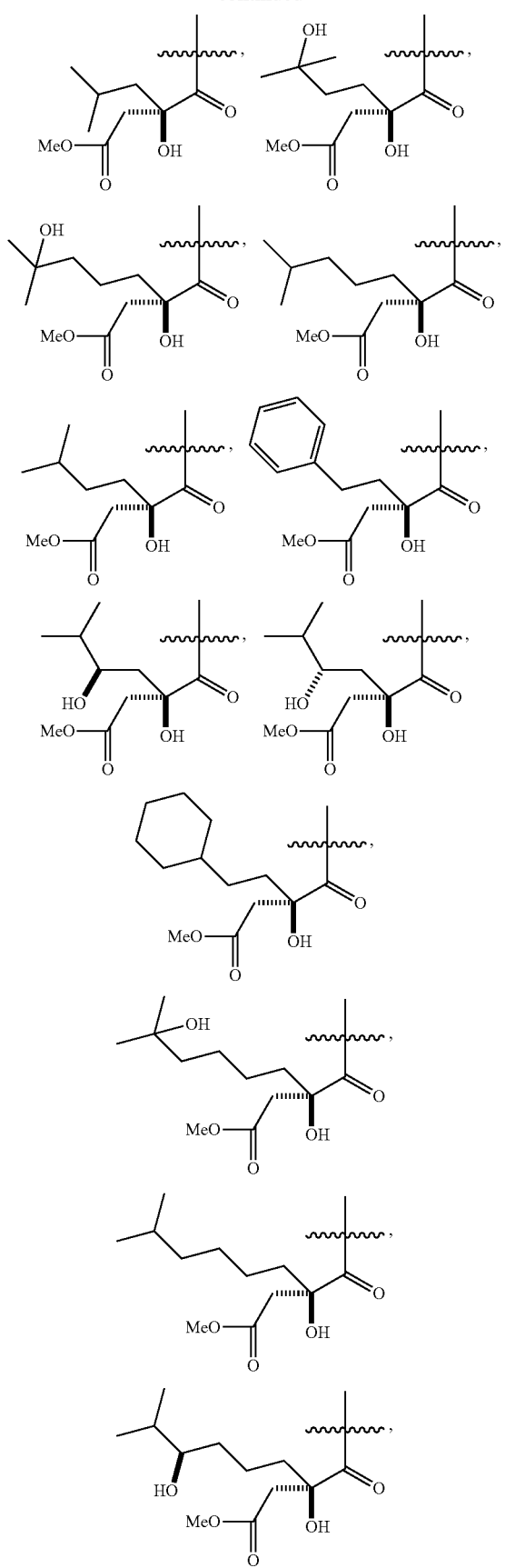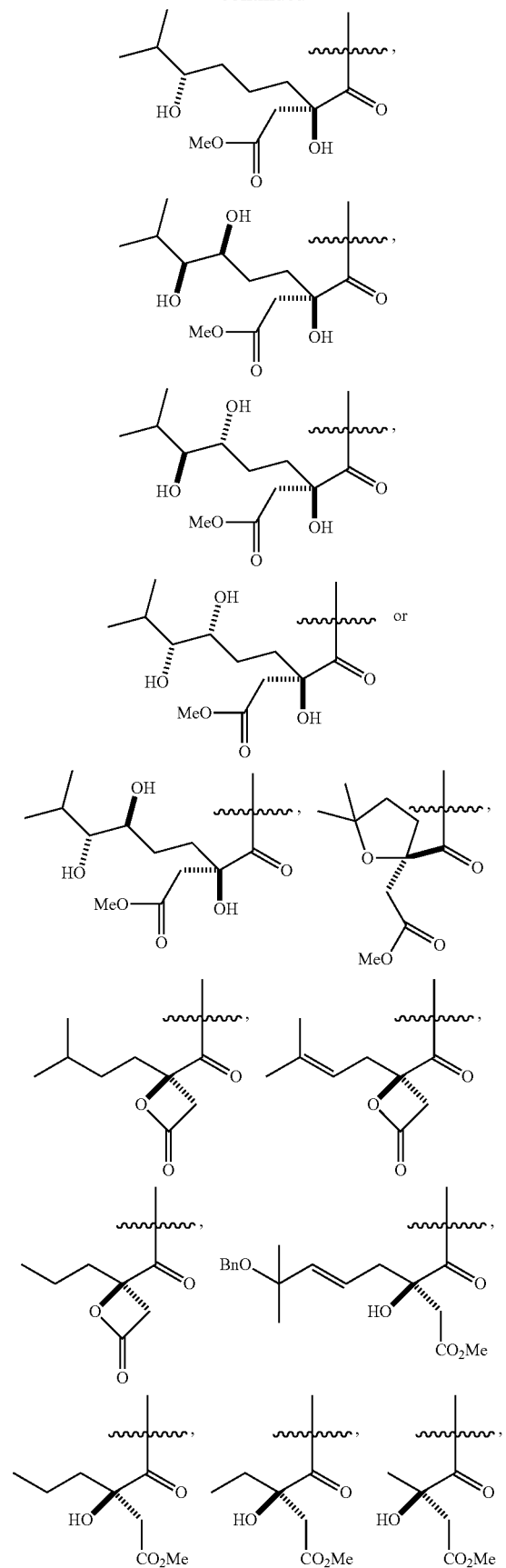

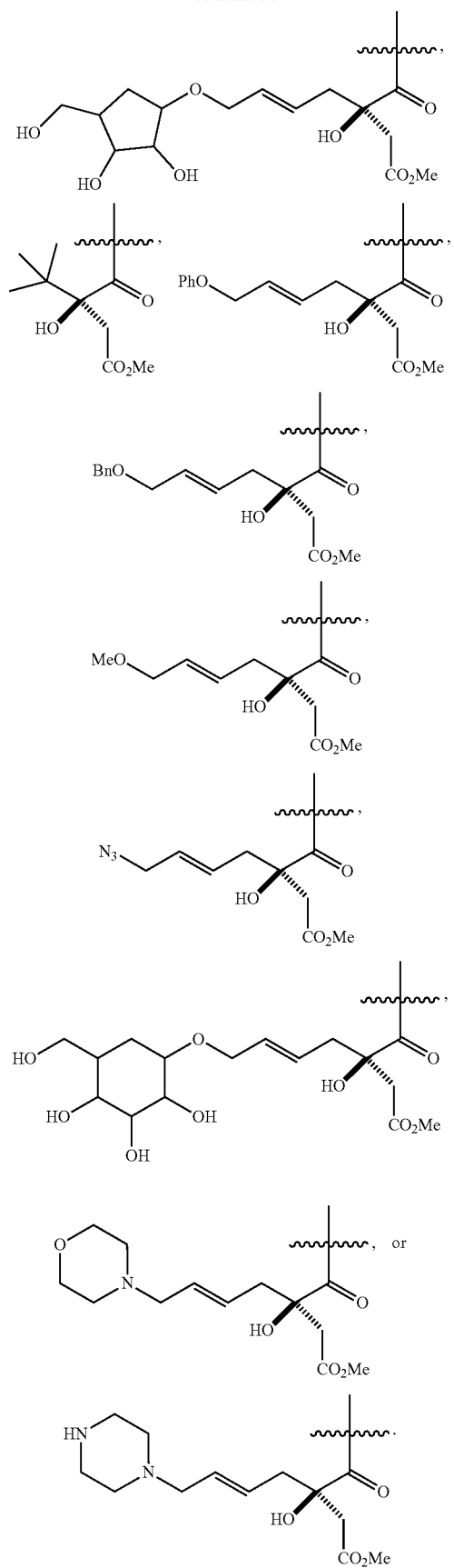
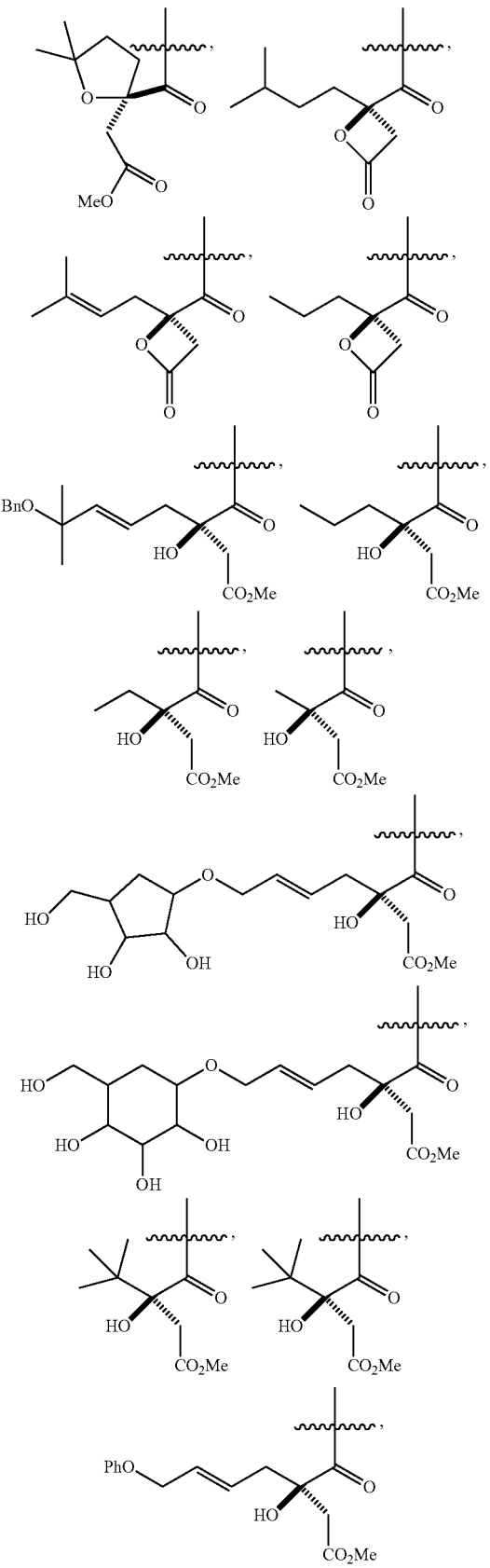
However, in certain other embodiment, $R^{14}$ is not

-continued
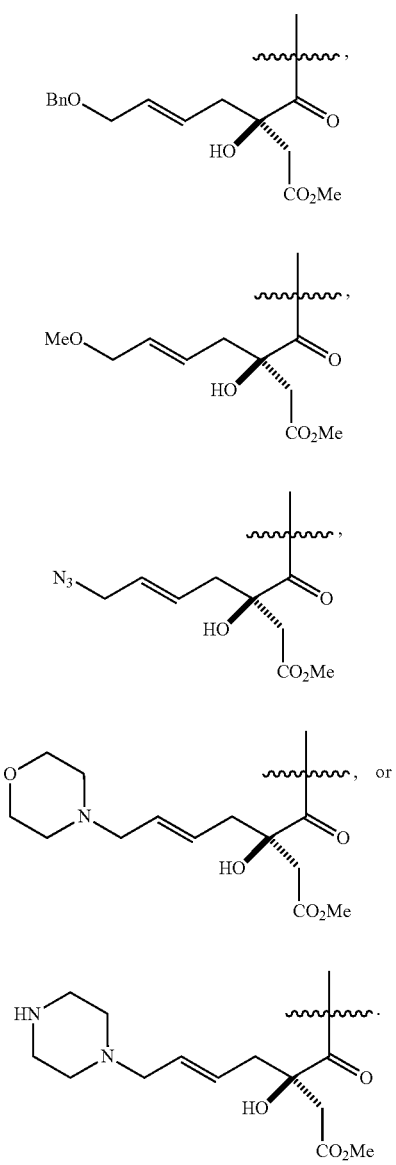
Additionally, or alternatively, in some embodiments, $R^{14}$ is not
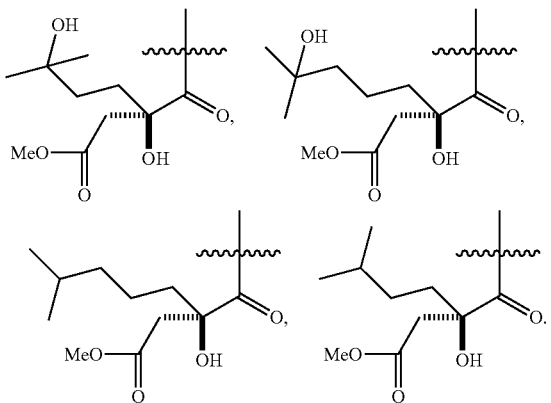
In some embodiment, $R^{14}$ is
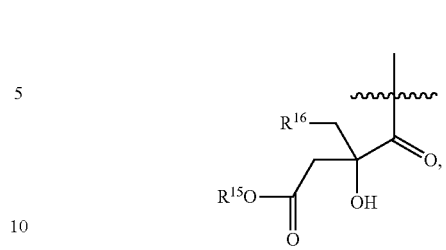
and may be
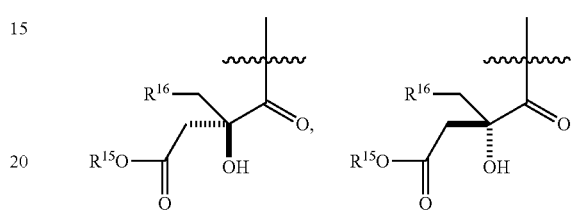
or a combination thereof, preferably
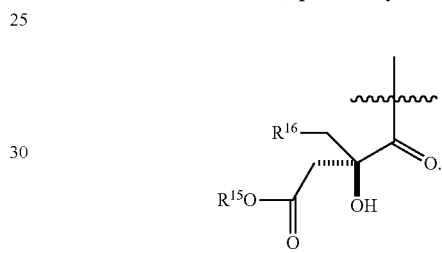
In particular embodiments of Formula V-2, the compound has a Formula VI-1, VI-2, VI-3, or a salt, solvate, N-oxide, prodrug, diastereomer or enantiomer thereof.
Formula VI-1
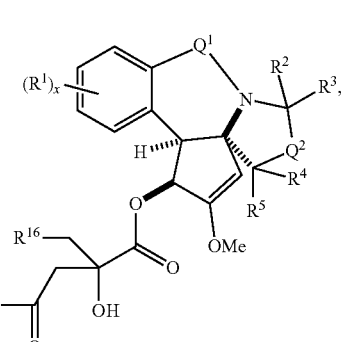
Formula VI-2
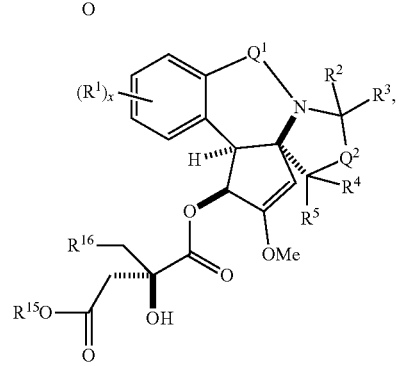

Formula VI-3

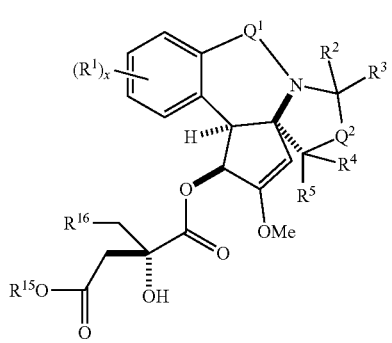

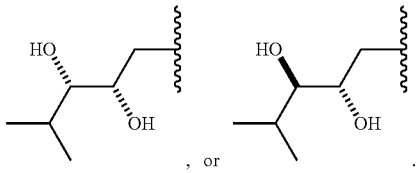
, or .

Compounds according to Formulas VI-1, VI-2 or VI-3 may have a formula selected from Formulas VI-1a, VI-1b, VI-1c, VI-1d, VI-2a, VI-2b, VI-2c, VI-2d, VI-3a, VI-3b, VI-3c, or VI-3d, or a salt, solvate, N-oxide, prodrug, diastereomer or enantiomer thereof.

With respect to Formulas VI-1, VI-2 and VI-3, x, $R^1$, $R^2$, $R^3$, $R^4$, $R^5$, $Q^1$ and $Q^2$ are as previously defined for Formula V-2. And with respect to $R^{14}$, and Formulas VI-1, VI-2 and VI-3. $R^{15}$ is H; alkyl, such as $C_{1-6}$alkyl, or $C_{1-4}$alkyl; or cycloalkyl, such as $C_{3-6}$cycloalkyl. $R^{16}$ is alkyl, cycloalkyl, aralkyl, hydroxyalkyl, or cycloalkylalkyl. In some embodiments, $R^{15}$ is methyl, ethyl, propyl, isopropyl, or cyclopropyl, and in certain embodiments, $R^{15}$ is methyl.

In certain embodiments, $R^{16}$ is methyl, ethyl, isopropyl,

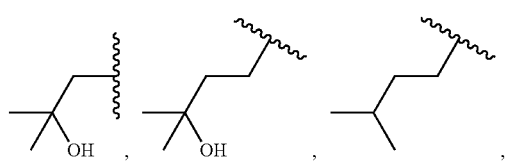

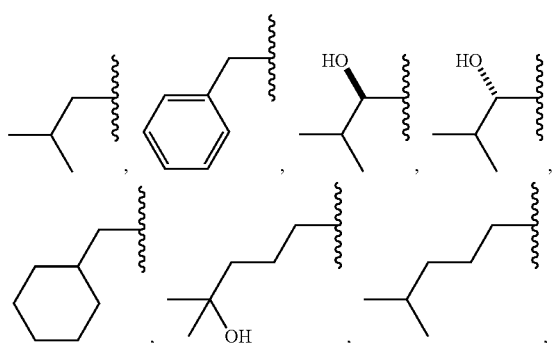

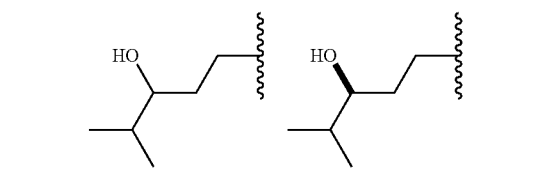

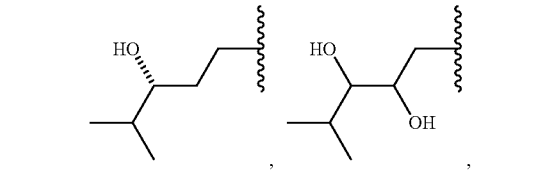

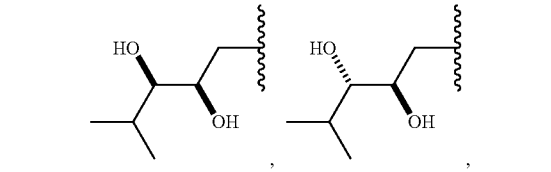

Formula VI-1a

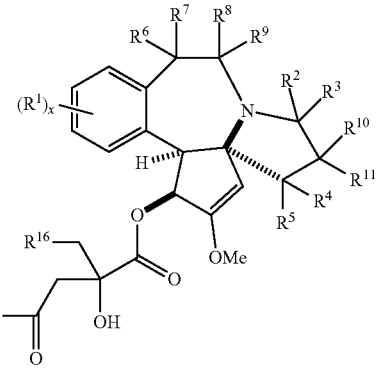

Formula VI-1b

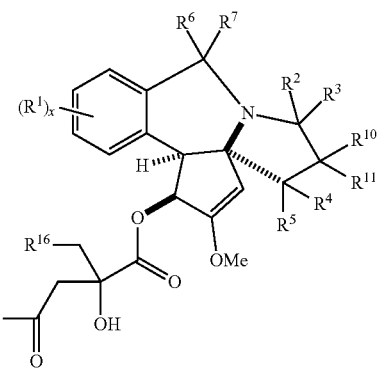

Formula VI-1c

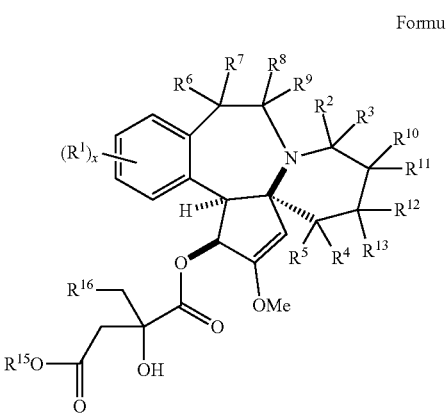

Fromula VI-1d
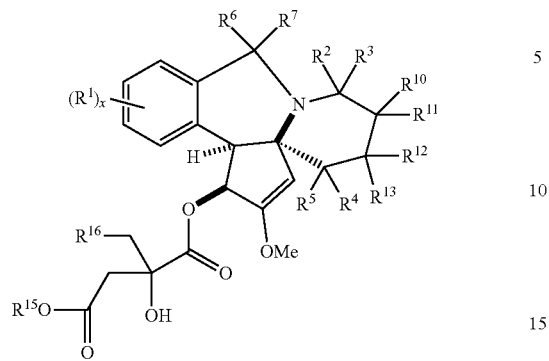
Fromula VI-2d
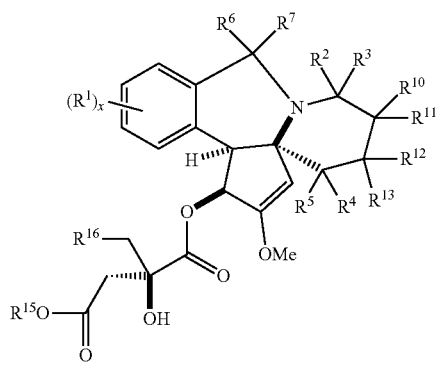
Formula VI-2a
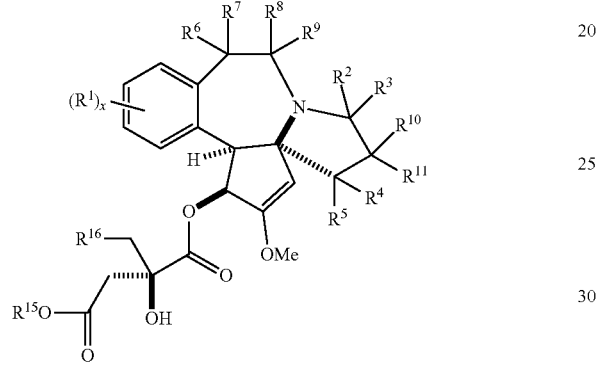
Formula VI-3a
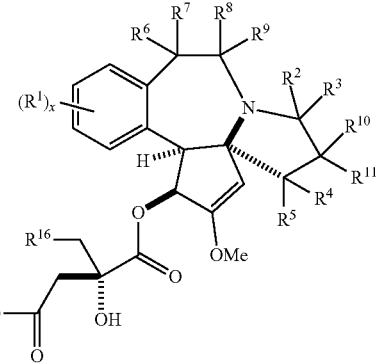
Formula VI-2b
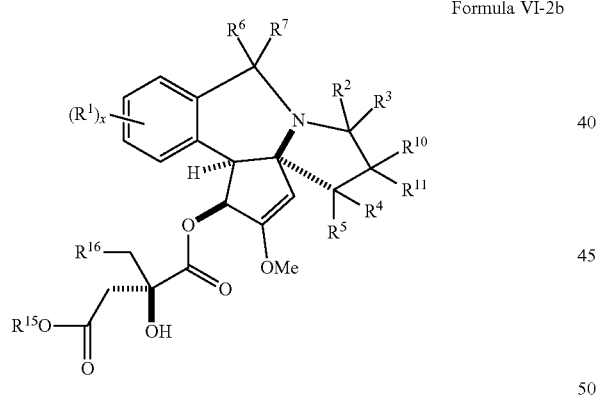
Formula VI-3b
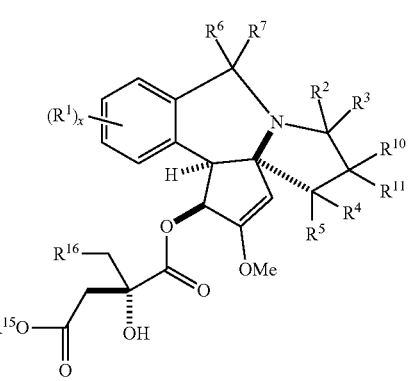
Formula VI-2c
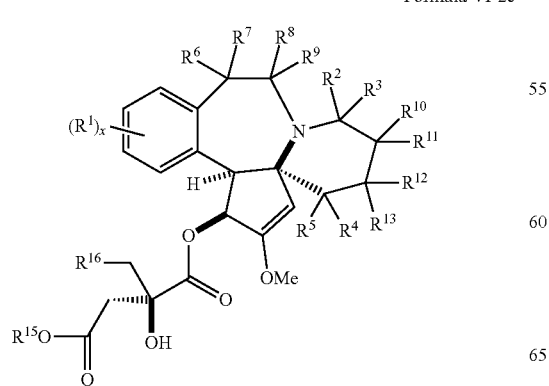
Formula VI-3c
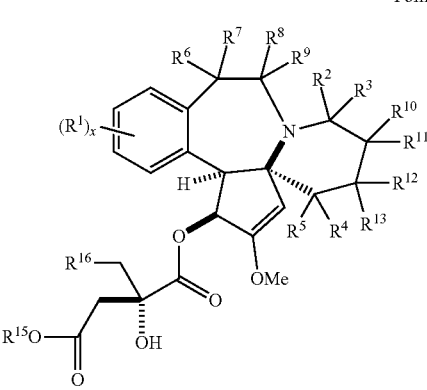

-continued
Fromula VI-3d
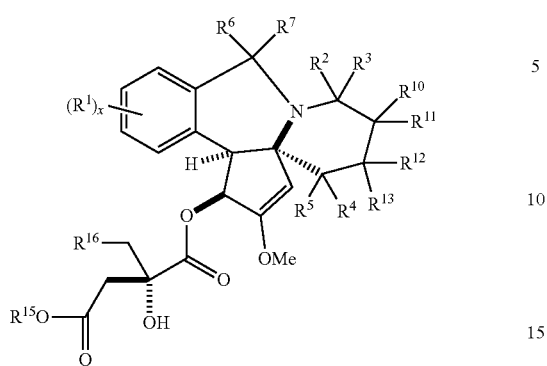
With respect to Formulas VI-1a, VI-1b, VI-1c, VI-1d, VI-2a, VI-2b, VI-2c, VI-2d, VI-3a, VI-3b, VI-3c, or VI-3d, x, and $R^1$-$R^{13}$ are as previously defined for Formulas I-a to I-d, and $R^{15}$ and $R^{16}$ are as previously defined for Formula VI-1, VI-2 and VI-3.
In some embodiments of Formulas V-2, VI-1, VI-2, VI-1a, and VI-2a, the compound is not
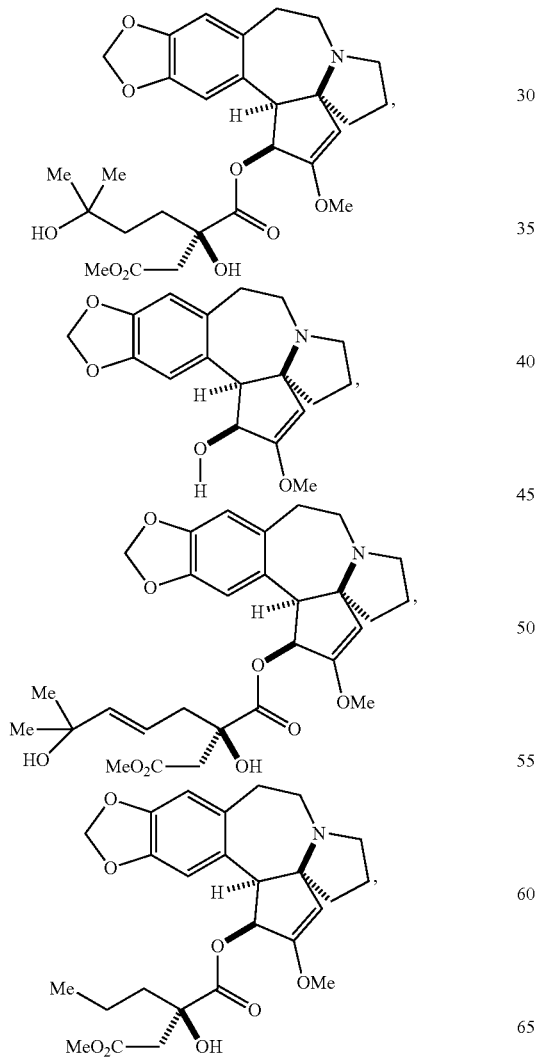
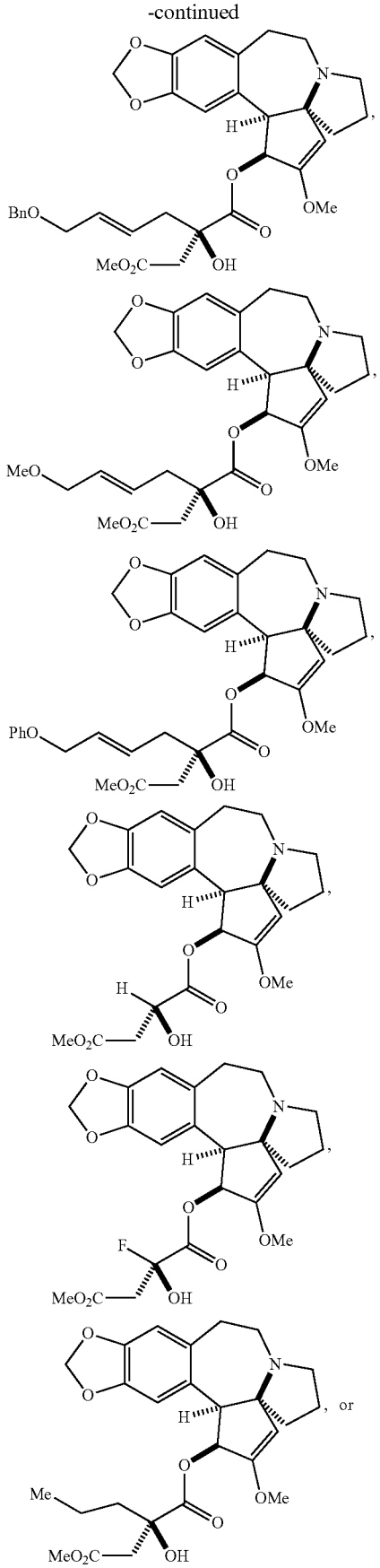

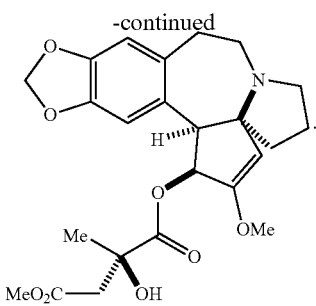

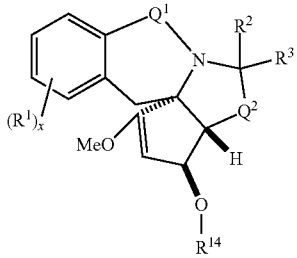
Formula VIII-2

Also disclosed are compounds according to Formulas VII-1, VII-2, and VII-3 and VIII-1, VIII-2 and VIII-3, or a salt, solvate, N-oxide, prodrug, diastereomer or enantiomer thereof.

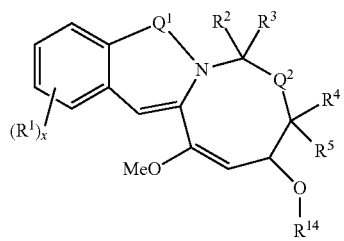
Formula VII-1

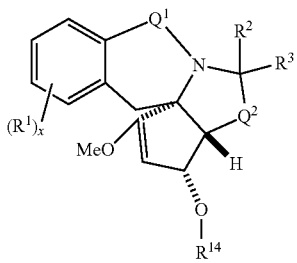
Formula VIII-3

With respect to Formulas VII-1, VII-2, VII-3, VIII-1, VIII-2 and VIII-3, x, $R^1$, $R^2$, $R^3$, $R^4$, $R_5$, $Q^1$ and $Q^2$ are as previously defined for Formula I, and $R^{14}$ is as previously defined for Formulas V-1, V-2 and V-3.

In some embodiments of Formulas VII-1 and VIII-1, the compounds have a Formula IX-1, IX-2, or IX-3 or X-1, X-2 or X-3, respectively, or a salt, solvate, N-oxide, prodrug, diastereomer or enantiomer thereof.

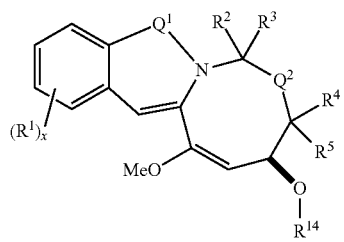
Formula VII-2

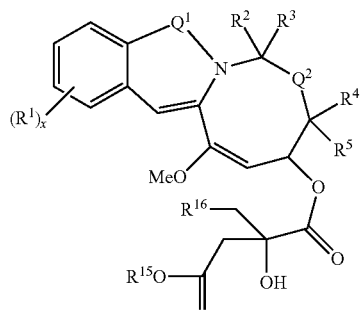
Formula IX-1

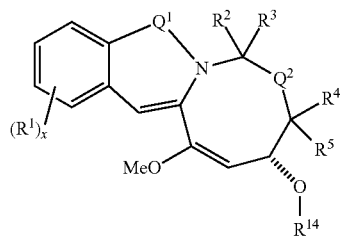
Formula VII-3

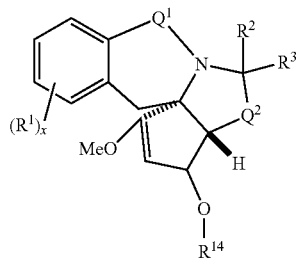
Formula VIII-1

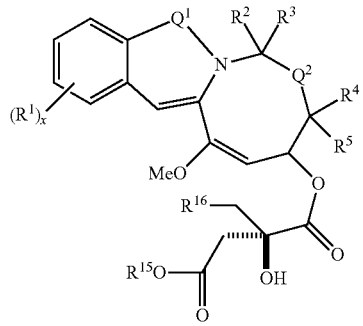
Formula IX-2

Formula IX-3
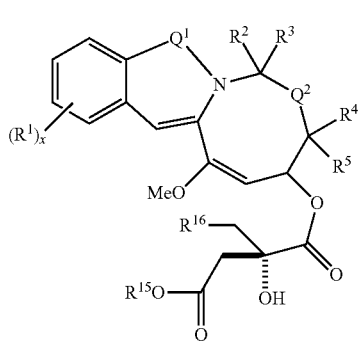

Formula X-1
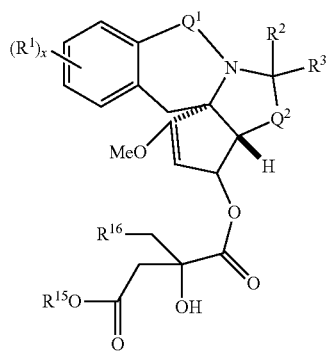

Formula X-2
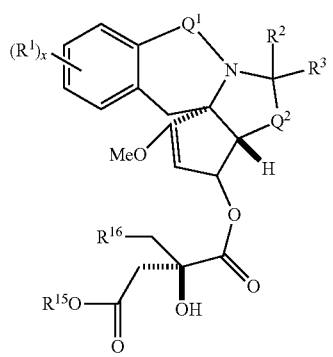

Formula X-3
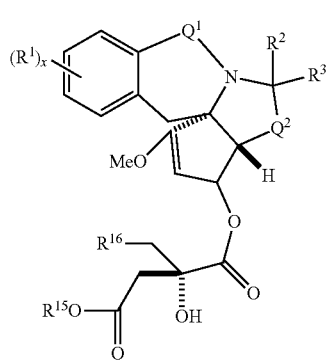

Formula IX-2a
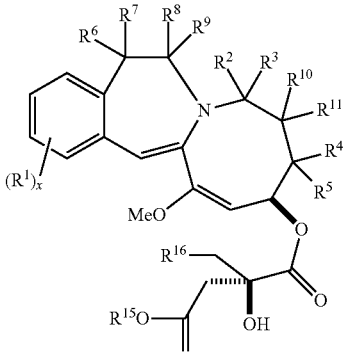

Formula IX-2b
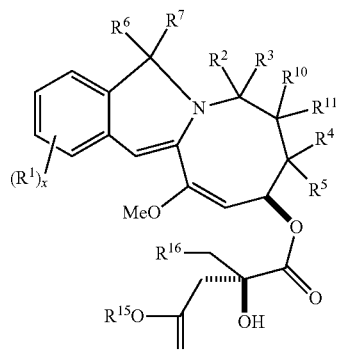

Formula IX-2c
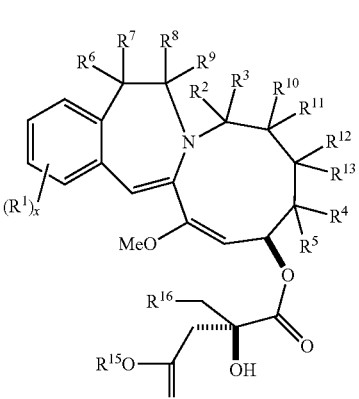

Formyla IX-2d
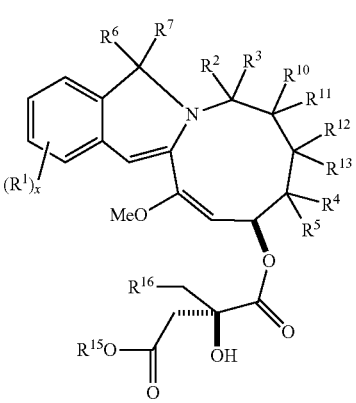

With respect to Formulas IX-1, IX-2, IX-3, X-1, X-2, and X-3, x, $R^1$, $R^2$, $R^3$, $R^4$, $R^5$, $Q^1$ and $Q^2$ are as previously defined for Formula I, and $R^{15}$ and $R^{16}$ are as previously defined for Formulas VI-1, VI-2 and VI-3.

Compounds according to Formula IX-2 may have a formula selected from Formulas IX-2a, IX-2b, IX-2c, IX-2d, IX-2e, IX-2f, IX-2g, or IX-2h, or a salt, solvate, N-oxide, prodrug, diastereomer or enantiomer thereof.

Formula IX-2e

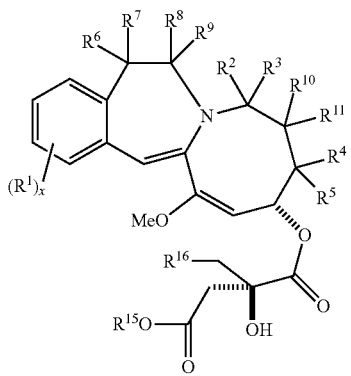

Formula IX-2f

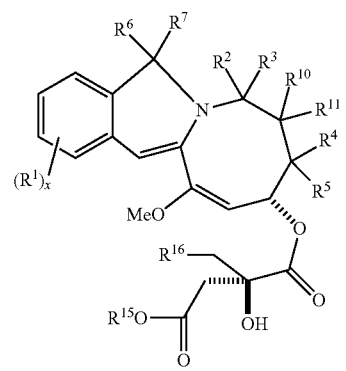

Formula IX-2g

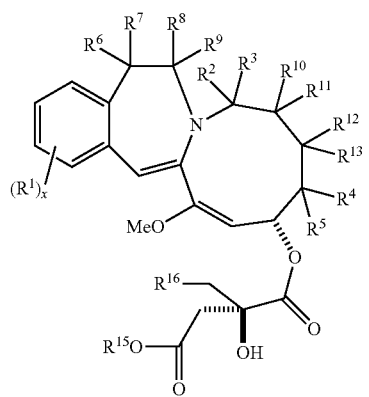

Formula IX-2h

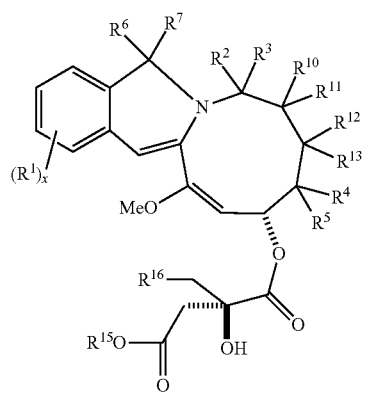

With respect to Formulas IX-2a, IX-2b, IX-2c, IX-2d, IX-2e, IX-2f, IX-2g, and IX-2h, x, and $R^1$-$R^{13}$ are as previously defined for Formulas I-a to I-d, and $R^{15}$ and $R^{16}$ are as previously defined for Formula VI-1, VI-2 and VI-3.

Compounds according to Formula X-2 may have a formula selected from Formulas X-2a, X-2b, X-2c, X-2d, X-2e, X-2f, X-2g, or X-2h, or a salt, solvate, N-oxide, prodrug, diastereomer or enantiomer thereof.

Formula X-2a

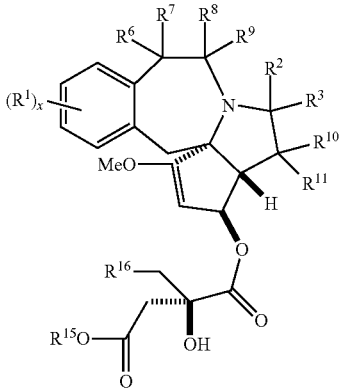

Formula X-2b

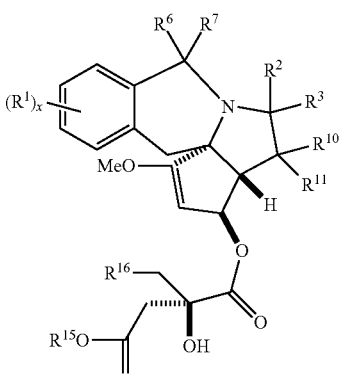

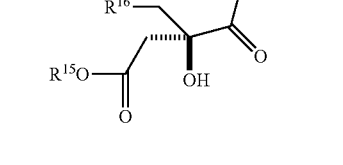

Formula X-2c

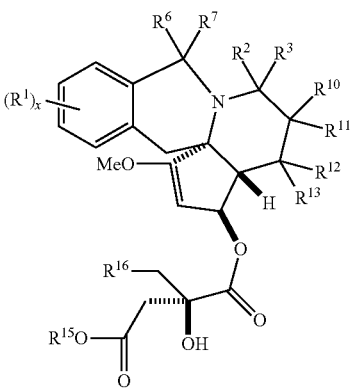

Formula X-2d

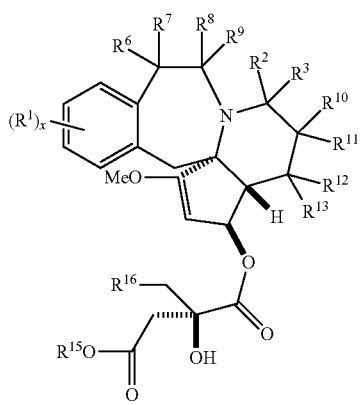

Formula X-2e

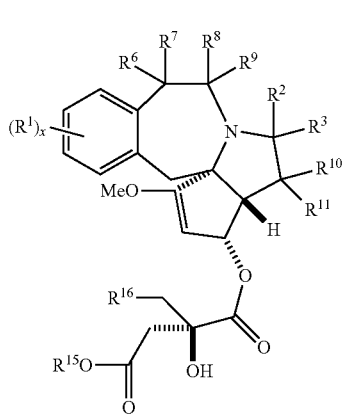

Formula X-2f

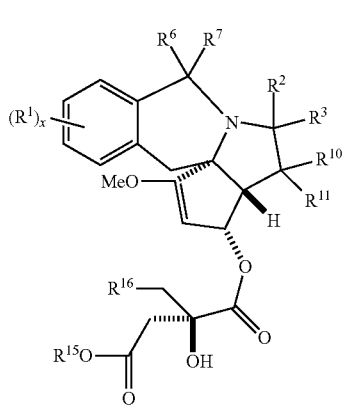

Formula X-2g

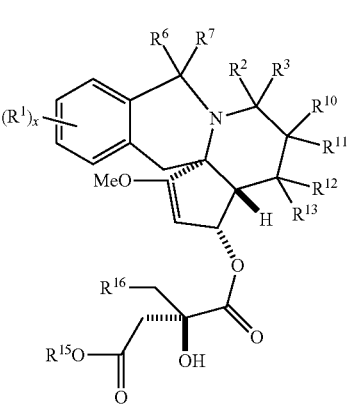

Formula X-2h

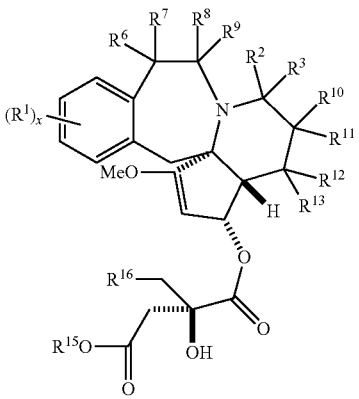

With respect to Formulas X-2a, X-2b, X-2c, X-2d, X-2e, X-2f, X-2g, and X-2h, x, and $R^1$-$R^3$ and $R^6$-$R^{13}$ are as previously defined for Formulas I-a to I-d, and $R^{15}$ and $R^{16}$ are as previously defined for Formula VI-1, VI-2 and VI-3.

And in any of Formulas I to X-2h described herein one or more of the following conditions may apply, if the particular moiety or variable(s) recited in the condition is present in the formula(s):

the

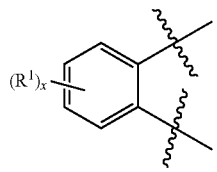

moiety is not

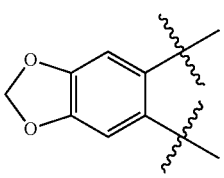

;

if $R^2$, $R^3$, $R^4$ and $R^5$ are all hydrogen then $Q^2$ is not —CH$_2$—;

if $Q^2$ is —CH$_2$— then one or more of $R^2$, R, $R^4$ and $R^5$ is not hydrogen;

$Q^1$ is not —CH$_2$CH$_2$—;

at least one of $R^6$, $R^7$, $R^8$ and $R^9$ is not H; or at least one of $R^2$, $R^3$, $R^4$, $R^5$, $R^{10}$ and $R^{11}$ is not hydrogen.

III. Methods for Making the Disclosed Compounds

I. Overview

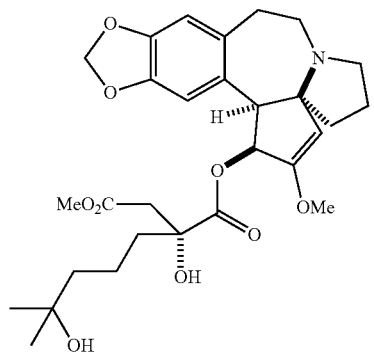
(−)-homoharringtonine (HHT)

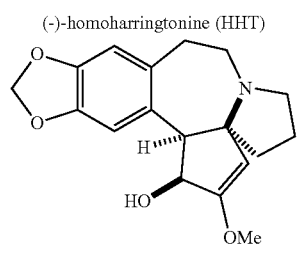
(−)-cephalotaxine (1)

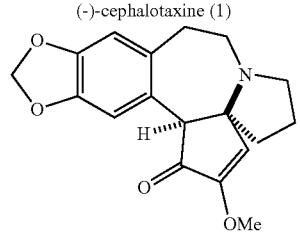
(−)-cephalotaxinone (2)

Despite total syntheses of HHT being reported, HHT is still prepared commercially by esterification of (−)-cephalotaxine (1). Cephalotaxine has been synthetically prepared, but commercial HHT is still prepared from plant-derived cephalotaxine, rather than by a fully synthetic method.

Cephalotaxine (1) has been prepared by borohydride reduction of cephalotaxinone (2). Retrosynthetic analysis by the present inventors suggested that 2 could be made from a macrocycle 5, via intermediates 3 and 4 (Scheme 1). And, in turn, macrocycle 5 could be synthesized from coupling partners 6 and 7.

Scheme 1

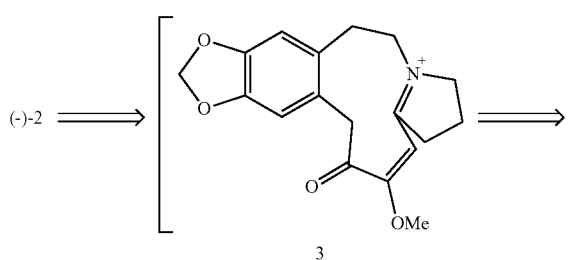

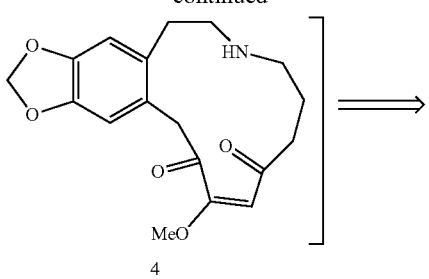

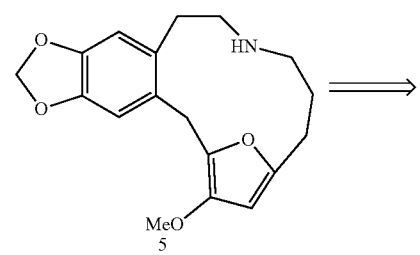

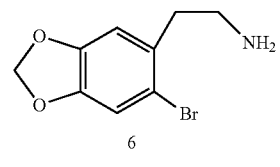

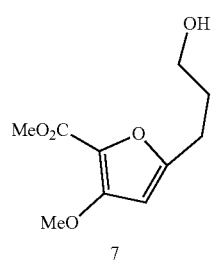

Scheme 2 provides the synthetic route that was attempted based on the retrosynthetic analysis shown in Scheme 1. Furan 7 was coupled to amine 8 to produce intermediate 9. However, conditions to produce macrocycle 5 from intermediate 9 could not be identified. The ester functionality in 9 was surprisingly resistant to any types of hydride reduction or nucleophilic additions. Similarly, the ester in 7 (or alcohol protected congeners) was resistant to reduction or intermolecular addition of nucleophilic reagents derived from 8. Without being bound to a particular theory, the lack of electrophilicity of 7 and 9 may arise from the lone pairs on the methoxy group and the furanyl oxygen, which can donate to the ester carbonyl decreasing reactivity.

Scheme 2

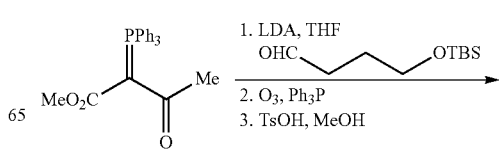

-continued

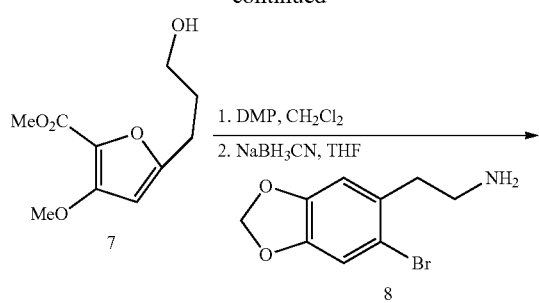

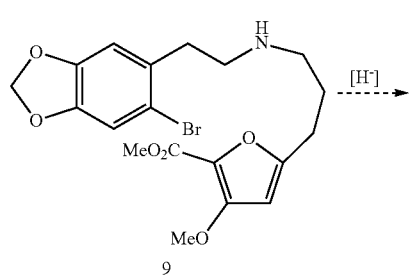

II. Synthesis

A. Formula I

A second synthetic route to make intermediate 5 was proposed. In some embodiments, the second synthetic route comprises:

i) treating a protected hydroxyl ketone of Formula A-1 with a haloacetate ester of Formula A-2 to form a compound of Formula A-3

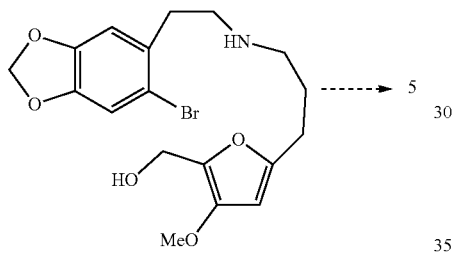

ii) treating the compound of Formula A-3 with a protected amino compound of Formula A-4 to form a compound of Formula A-5

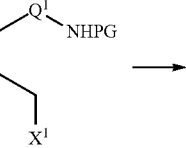
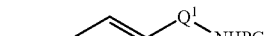

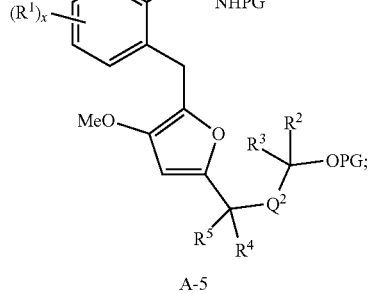

iii) converting the protected hydroxyl (OPG) moiety of A-5 to a leaving group in a compound of Formula A-6

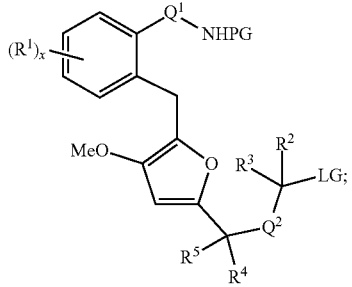

and iv) cyclizing A-6, typically in the presence of a base, such as LiOH, to form the compound of Formula I,

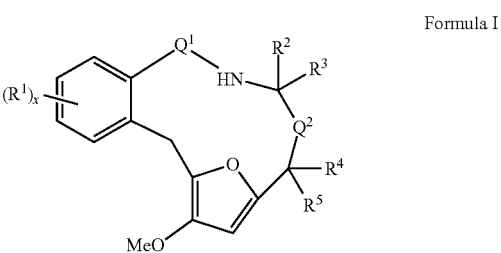

Formula I or a salt, solvate, N-oxide, prodrug, enantiomer or diastereomer thereof.

With respect to the above method, each PG independently is a protecting group, such as a protecting group disclosed herein, and in some embodiments, the protecting group is a carbamate, acetate and/or silyl protecting group described herein. LG is a leaving group, such as a sulfonyl leaving group, typically, methylate or tosylate. Each $X^1$ independently is a halogen, such as F, Br, Cl, or I, preferably Cl or Br. $R^a$ is alkyl, such as $C_{1-6}$alkyl, $C_{1-4}$alkyl or $C_{1-2}$alkyl. And the compound of Formula I is as defined herein.

In certain embodiments, each PG independently is trifluoroacetate or a silyl protecting group; LG is mesylate; $X^1$ is Cl; or any combination thereof.

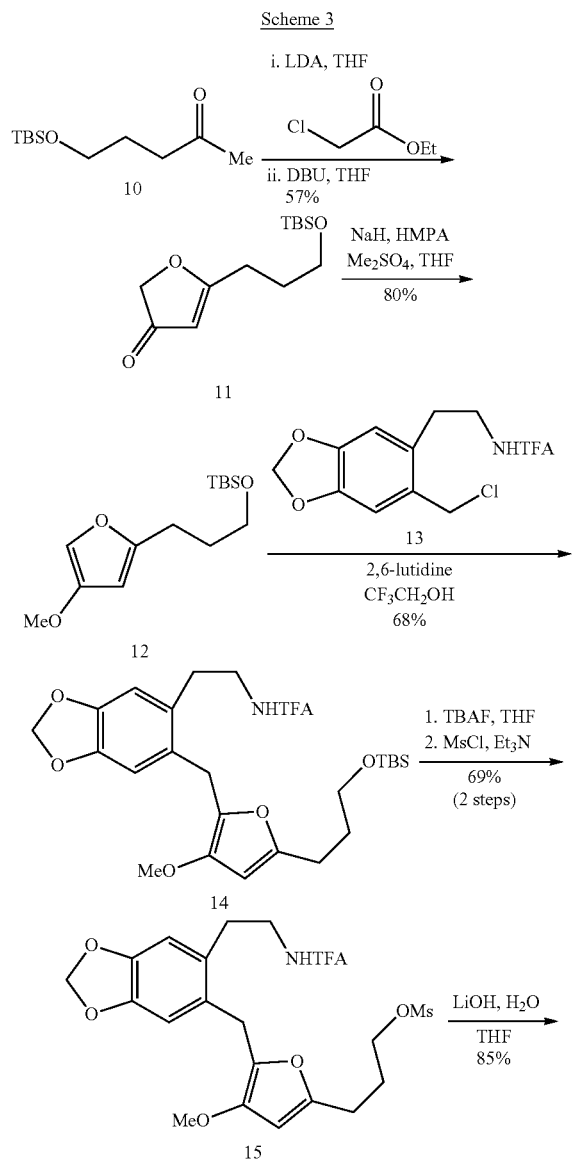

Scheme 3 provides an exemplary embodiment of the second synthetic route, along with exemplary reagents and solvents. With respect to Scheme 3, a protected hydroxypentanone 10 was treated with a haloacetate in a Claisen-type condensation and cyclization to produce furanone 11. Methylation of furanone 11, such as with dimethylsulfate, in the presence of a suitable base, such as sodium hydride in a suitable solvent, gave 3-methoxyfuran 12. 3-Methoxyfuran 12 was treated with protected amine 13 to give compound 14. Then the alcohol protecting group was replaced with a mesylate leaving group to form compound 15. Treatment of 15 with a suitable aqueous base produced macrocycle 5. Suitable aqueous bases include, but are not limited to, any base that facilitates the cyclization reaction, such as a hydroxide base including lithium hydroxide, sodium hydroxide, potassium hydroxide, or a combination thereof.

B. Formula II

The method may further comprise v) treating the compound of Formula I with an oxidizing agent to form a racemic compound of Formula II

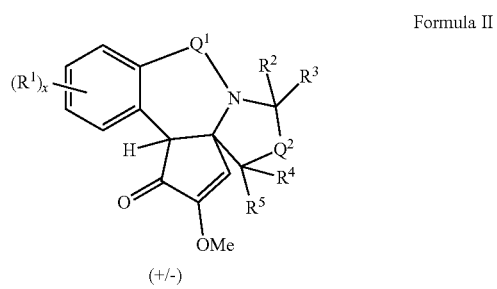

Formula II wherein x, $R^1$, $R^2$, $R^3$, $R^4$, $R^5$, $Q^1$ and $Q^2$ are as defined herein with respect to Formula II. The oxidizing agent may be any suitable oxidizing agent, such as 2,3-dichloro-5,6-dicyano-1,4-benzoquinone (DDQ). And the reaction is performed in a solvent suitable to facilitate the reaction. Exemplary solvents include, but are not limited to, an alcohol, such as methanol, ethanol, propanol, isopropanol, tert-butanol, or trifluoroethanol; toluene; tetrahydrofuran (THF); a chlorinated solvent, such as chloroform or dichloromethane; or a combination thereof.

Compounds according to Formula III and/or Formula IV may also be formed by the reaction to form a compound according to Formula II. Using a solvent that comprises, or is, an alcohol may facilitate the formation of a mixture of compounds having a Formula II, II and IV. In some embodiments, using an alcohol solvent, such as methanol, ethanol, propanol, isopropanol, or tert-butanol, produces a mixture of compounds of Formula II, II and IV in substantially equal molar amounts, i.e., approximately, 1:1:1 molar ratio. However, in certain embodiments, using trifluoroethanol results in a substantially higher yield of a compound according to Formula II, such as greater than 50%, greater than 60%, or greater than 70%, and lower yields of compounds of Formulas II and IV, such as from 0% to 20%.

The compounds of Formulas II, III and IV can be separated and purified by chromatography, such as flash column chromatography, and/or recrystallization.

Without being bound to a particular theory, the synthesis of compounds of Formula II may proceed as shown in Scheme 4.

Scheme 4

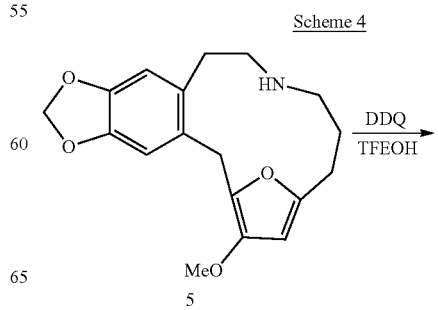

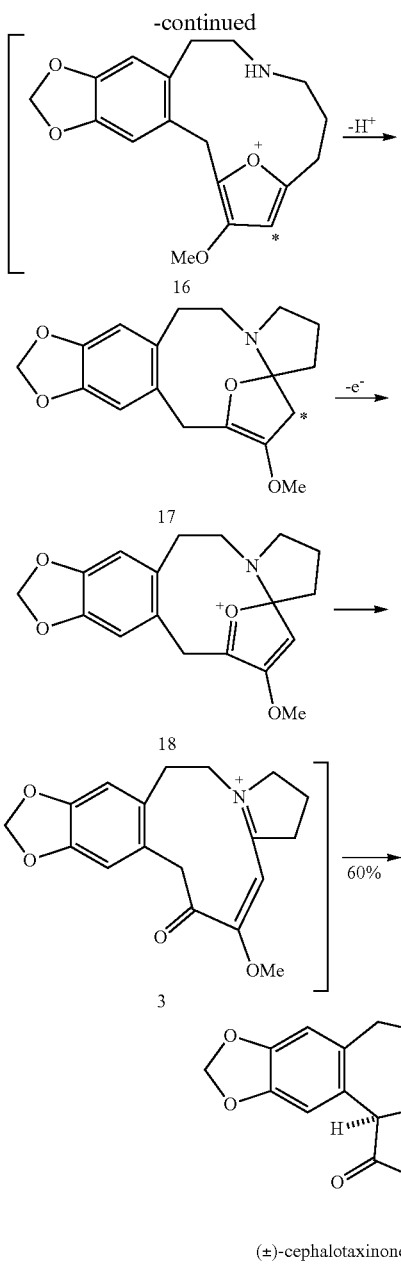

(±)-cephalotaxinone (2)

In an exemplary synthesis, intermediate 5 was first treated with DDQ in tert-butanol to produce racemic 2. Although the reaction produced cephalotaxinone 2, the yield was only about ~10%. Oxidative furan openings may be responsive to the reaction solvent, and the oxidations often result in incorporation of an alcoholic solvent to the furan. It was suspected that polar non-nucleophilic solvents might stabilize the charged reactive intermediates without solvolytic trapping, and thus could increase the reaction yield. A solvent screen was performed using tert-butanol, various tert-butanol-water mixtures, ethanol, toluene, $CH_2Cl_2$, THF, and trifluoroethanol. The solvent screen revealed that trifluoroethanol markedly increased the reaction yield to 60%, whereas, the other solvents tested only produced yields of from 0 to 20% (Scheme 4).

Without being bound to a particular theory, single electron oxidation of 5 may produce a radical cation 16. Transannular trapping of the radical oxocarbenium ion by the tethered amine results in 17. Oxidation of 17 gives oxocarbenium ion 18. Fragmentation of 18 releases iminium ion 3, which can proceed via Mannich cyclization to give (±)-cephalotaxinone (2) as a single diasteromer.

Synthesis of non-racemic cephalotaxinone could, at least in principle, be accomplished by rendering the key transformation (5→2) enantioselective; however, it was unclear which step of the mechanism would need to be controlled. Considering the plausible mechanism shown, the enantio-determining step may be the final Mannich event. Alternatively, if hypothetical intermediate 3 has a conformation that is stable on the timescale of the Mannich step, then there would be a possibility of conformational chirality of the undecatrienone ring. In such a scenario, the initial transannular addition to the furanyl radical cation 16 could be enantiodetermining. Finally, such a scenario would require good transfer of point-to-conformational chirality, and non-reversibility of the mechanistic steps.

In these scenarios, the enantiodeterming step is an addition to a cationic species. The counter anion is dichlorodicyanohydroquinone anion. Efforts to control this process by introducing a chiral counter anion were unsuccessful, despite adding several chiral protic acids in multiple solvents. No measureable enantioenrichment of cephalotaxinone was ever observed.

C. Formulas V-1, V-2 and V-3

In some embodiments, the method further comprises a step vi) comprising treating the compound of Formula II with a reducing agent to produce an alcohol according to one or more of Formulas V-1, V-2 or V-3. The reducing agent can be an agent suitable to reduce the ketone to an alcohol, such as sodium borohydride. In some embodiments, a chiral reducing agent is used. And in certain embodiments, step iv) comprises treating the racemic compound of Formula II with a suitable chiral catalyst, such as Ru(p-cymene)-(S,S)-TsDPEN, a suitable base, such as trimethylamine, and a suitable acid, such as formic acid, to form a compound of Formula A-7 and (+)-compound of Formula II (Scheme 5). The base and acid may be present in any suitable ratio to facilitate the reaction, such as 5:1 base:acid.

Scheme 5

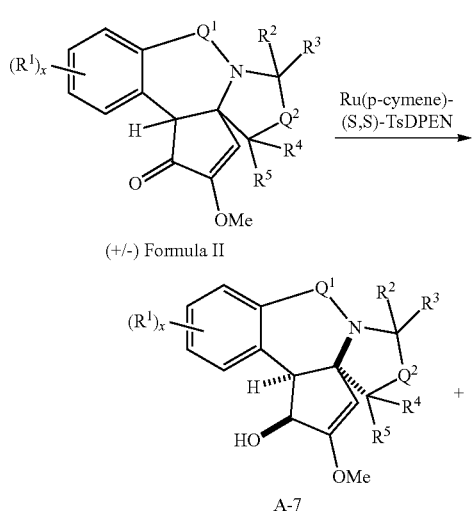

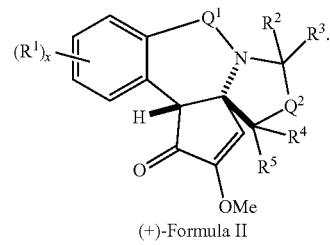

(+)-Formula II

A person of ordinary skill in the art understands that the (+)-Formula II and (−)-Formula II refer to the (+) and (−) isomers, respectively, of the compound of Formula II, or a compound having an enantiomeric excess of either the (+) or (−) isomer, respectively, as defined herein, and racemic or (±)-Formula II refers to an approximate 50:50 mixture of the (+) and (−) isomers, i.e., an e.e. of about zero. In an exemplary embodiment of Scheme 5, enantioenriched cephalotaxine 1 was prepared. To the inventors' knowledge, no enantioselective reduction of 2 has previously been reported.

Compounds according to Formulas VII-1 to VII-3 and VIII-1 to VIII-3 can synthesized by a similar method using the appropriate starting compound.

A side chain moiety can then be added to the compound at the hydroxyl position to form an ester or ether moiety. Techniques for adding the side chain are known to persons of ordinary skill in the art, and may comprise treating the hydroxyl compound with an activated side chain moiety in the presence of a base and/or coupling agent. The activated side chain moiety may comprise a suitable leaving group, such as a halogen, typically, Cl or Br, mesylate, tosylate, or anhydride. In some embodiments, the starting material for the side chain comprises an acid, and the activated side chain moiety comprises an activated acid, such as an acyl halide or a mixed anhydride. The resulting products are purified by chromatography and/or recrystallization.

Scheme 6

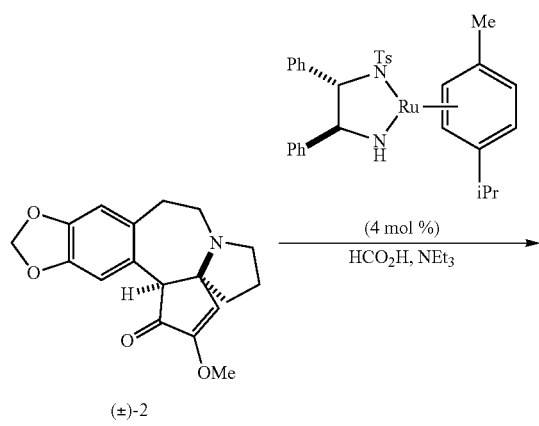

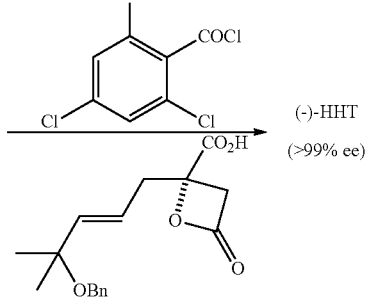

For example, Scheme 6 provides the synthetic route used to produce (−)-cephalotaxine 1 with very high enantioselectivity at 50% conversion. Spectroscopic data and optical rotation for (−)-cephalotaxine matched those previously reported. (−)-HHT was then produced from (−)-cephalotaxine 1 following a literature procedure described herein in Examples 9-11, and also by Eckelbarger, et al., *Chem. Eur. J.* 2008, 14, 4293-4306, which is incorporated herein by reference in its entirety. Spectral data and optical rotation for (−)-HHT also matched those from previous reports.

In embodiments where the side chain moiety comprises one or more chiral centers and the product therefore comprises diastereomers, separate diastereomers are separated by chromatography and/or recrystallization. For example, compounds according to Formulas IX-2d and IX-2h are separated by chromatography and/or recrystallization.

D. Racemization

The method described in Schemes 5 and 6 also produces about 49% yield of the undesired (+)-compound of Formula II, such as (+)-2 as a by-product. To improve the overall yield of the synthetic route, and reduce the amount of waste, the (+)-compound of Formula II may be further treated with 2,2-dimethoxypropane and p-toluene sulfonic acid to form an additional amount of the racemic compound of Formula II, i.e., an approximate 50:50 mixture of (−)-Formula II and (+)-Formula II (Scheme 7).

Scheme 7

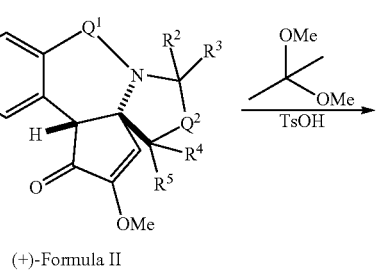

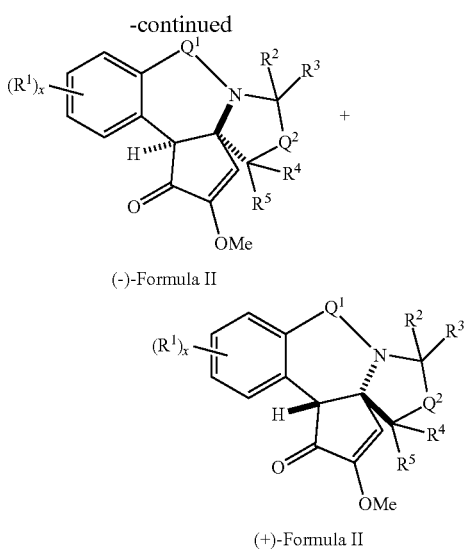

(-)-Formula II (+)-Formula II

The additional amount of the racemic mixture can then be treated with an additional amount of the catalyst as described above, to form an additional amount of compound A-7.

In an exemplary embodiment shown in Scheme 8, (+)-2 was treated with 2,2-dimethoxypropane and p-toluenesulfonic acid (TsOH) to produce (±)-2, which could then be treated according to Schemes 5 and 6 to produce additional enantioenriched cephalotaxine 1.

Scheme 8

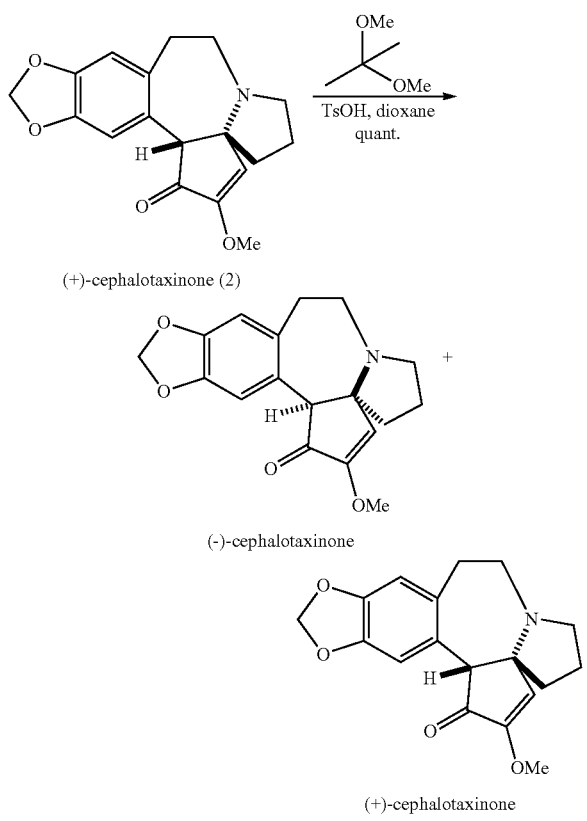

(+)-cephalotaxinone (2)

(-)-cephalotaxinone (+)-cephalotaxinone

IV. Methods for Using the Compounds

I. Compositions

Pharmaceutical compositions for administration to a subject, such as a human or animal subject, can include at least one further pharmaceutically acceptable additive such as carriers, thickeners, diluents, buffers, preservatives, surface active agents and the like, in addition to the disclosed compound(s). Pharmaceutical compositions can also include one or more additional active ingredients such as antimicrobial agents, anti-inflammatory agents, anticancer agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds disclosed herein.

Compositions comprising one or more of the disclosed compounds typically comprise from greater than 0 up to 99% of the disclosed compound, or compounds, and/or other therapeutic agent by total weight percent. More typically, compositions comprising one or more of the disclosed compounds comprise from about 1 to about 20 total weight percent of the disclosed compound(s) and other therapeutic agent, and from about 80 to about 99 weight percent of a pharmaceutically acceptable excipient.

Preferably, the disclosed compound, combinations of disclosed compounds, or compositions thereof, will provide therapeutic or prophylactic benefit without causing substantial toxicity. Toxicity of the disclosed compound can be determined using standard pharmaceutical procedures. The dose ratio between toxic and therapeutic (or prophylactic) effect is the therapeutic index. Disclosed compounds that exhibit high therapeutic indices are preferred.

In general, the nature of the excipient, such as a carrier, will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the disclosed compound(s) can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of 0.3 to 3.0, such as 0.5 to 2.0, or 0.8 to 1.7.

The disclosed compound(s), or a composition thereof, can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The disclosed compound(s), or a composition thereof, can be combined with the base or vehicle according to a variety of methods, and release of the compound can be by diffusion, disintegration of the vehicle, or associated formation of water channels. In some circumstances, the disclosed compound(s) or a composition thereof is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the disclosed compound(s), or a composition thereof, can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the disclosed compound can be brought about by including in the composition an agent which delays absorption, for example, monostearate salts and gelatin.

In certain embodiments, the disclosed compound(s) or a composition thereof can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the disclosed compound(s) and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid).

Other useful biodegradable or bioerodable polymers include, but are not limited to, such polymers as poly(ε-caprolactone), poly(ε-caprolactone-CO-lactic acid), poly(ε-caprolactone-CO-glycolic acid), poly(D-hydroxy butyric acid), poly(alkyl-2-cyanoacrilate), hydrogels, such as poly (hydroxyethyl methacrylate), polyamides, poly(amino acids) (for example, L-leucine, glutamic acid, L-aspartic acid and the like), poly(ester urea), poly(2-hydroxyethyl-DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the disclosed compound(s) or a composition thereof can be delivered to a subject in a manner consistent with conventional methodologies associated with management of the disorder for which treatment or prevention is sought. In accordance with the disclosure herein, a prophylactically or therapeutically effective amount of the disclosed compound(s), or a composition thereof, is administered to a subject in need of such treatment for a time and under conditions sufficient to inhibit, and/or ameliorate a selected disease or condition or one or more symptom(s) thereof.

II. Administration

The administration of the disclosed compound(s), or a composition thereof, can be for either prophylactic or therapeutic purpose. When provided prophylactically, the disclosed compound(s) is provided in advance of any symptom. The prophylactic administration of the disclosed compound(s) serves to inhibit or ameliorate any subsequent disease process. When provided therapeutically, the disclosed compound(s) is provided at (or shortly after) the onset of a symptom of disease.

In some embodiments, the disclosed compounds are useful for treating and/or preventing diseases and/or disorders, such as proliferation diseases including solid tumor and non-solid tumor cancers. Exemplary proliferation diseases include, but are not limited to, bladder cancer, breast cancer, glioma, brain cancer, cervical cancer, colon cancer, rectal cancer, endometrial cancer, kidney cancer, oral cancer, ovarian cancer, prostate cancer, pancreatic cancer, head and neck cancer, liver cancer, lung cancer including non-small cell lung cancer and small cell lung cancer, skin melanomas, non-melanoma skin cancer, mesothelioma, sarcoma, lymphoma, such as Hodgkin lymphoma and non-Hodgkin lymphoma, leukemia, such as acute lymphoblastic leukaemia (ALL), acute myeloid leukaemia (AML), chronic lymphocytic leukaemia (CLL), and chronic myeloid leukaemia (CML), and myeloma.

Additionally or alternatively, the disclosed compounds are useful as antimicrobial agents and antiparasitic agents, such as antimalarial agents, particularly against chloroquine-resistant *Plasmodium falciparum*.

For prophylactic and therapeutic purposes, the disclosed compound(s), or a composition thereof, can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the disclosed compound(s) can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the disclosed compound(s).

Effective dosages can be estimated initially from in vitro assays. For example, an initial dosage for use in subjects can be formulated to achieve a circulating blood or serum concentration of active compound that is at or above an $IC_{50}$ or $EC_{50}$ of the particular compound as measured in an in vitro assay. Dosages can be calculated to achieve such circulating blood or serum concentrations taking into account the bioavailability of the particular compound. For guidance, the reader is referred to Fingl & Woodbury, "General Principles," In: *Goodman and Gilman's The Pharmaceutical Basis of Therapeutics*, latest edition, Pergamon Press, and the references cited therein.

Initial dosages can also be estimated from in vivo data, such as animal models. Animal models useful for testing the efficacy of compounds to treat or prevent the various diseases described above are well-known in the art. Persons of ordinary skill in the art can adapt such information to determine dosages suitable for human and/or other animal administration.

The actual dosage will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum therapeutic response. A therapeutically effective amount is also one in which any toxic or detrimental side effects of the compound and/or other biologically active agent is outweighed in clinical terms by therapeutically beneficial effects.

Dosage amounts of the disclosed compounds will typically be in the range of from about greater than 0 mg/kg/day, such as 0.0001 mg/kg/day or 0.001 mg/kg/day or 0.01 mg/kg/day, up to at least about 100 mg/kg/day. More typically, the dosage (or effective amount) may range from about 0.0025 mg/kg to about 1 mg/kg administered at least once per day, such as from 0.01 mg/kg to about 0.5 mg/kg or from about 0.05 mg/kg to about 0.15 mg/kg. The total daily dosage typically ranges from about 0.1 mg/kg to about 10 mg/kg or to about 20 mg/kg per day, such as from 0.5 mg/kg to about 10 mg/kg per day or from about 0.7 mg/kg per day to about 5 mg/kg/day. Dosage amounts can be higher or lower depending upon, among other factors, the activity of the disclosed compound, its bioavailability, the mode of administration, and various factors discussed above.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

The disclosed compounds may be co-administered with one or more additional therapeutic or active agents. Such agents include, but are not limited to, anticancer agents, antimicrobials, anti-inflammatory agent, immunosuppressant, antibiotic, anticoagulant, antibody, antiviral, antiparasitic including antimalarial, antifungal, anti-nausea, antidiarrhea, or a combination thereof. Exemplary additional agents include, but are not limited to, etoposide, amsacrine, cytarabine, mitoxantrone, bisantrene, IFN-α, or a combination thereof.

Additionally, or alternatively, the compounds may be used as part of a combination therapy, such as a combination comprising one or more of chemotherapy, biological therapy, targeted therapy, radiation therapy, or stem cell therapy.

V. EXAMPLES

General Experimental Details

All reactions were carried out under an inert Ar atmosphere in oven-dried glassware. Flash column chromatography (FCC) was carried out with SiliaFlash P60, 60 Å silica gel. Reactions and column chromatography were monitored with EMD silica gel 60 F254 plates and visualized with potassium permanganate, ceric ammonium molybdate, molybdate, ninhydrin, or iodine stains. Tetrahydrofuran (THF), methylene chloride ($CH_2Cl_2$), and methanol (MeOH) were dried by passage through activated columns. Triethylamine ($NEt_3$) and 1,4-dioxane was dried and distilled over calcium hydride. All other reagents and solvents were used without further purification from commercial sources.

Instrumentation: FT-IR spectra were obtained on NaCl plates with a PerkinElmer Spectrum Vision spectrometer. Proton and carbon NMR spectra ($^1$H NMR and $^{13}$C NMR) were recorded in deuterated chloroform ($CDCl_3$) unless otherwise noted on a Bruker 700 MHz Avance III Spectrometer with carbon-optimized cryoprobe and Bruker 400 MHz DPX-400 spectrometer. Multiplicities are abbreviated as follows: s=singlet, d=doublet, t=triplet, q=quartet, sept=septet, br=broad, m=multiplet. Enantiomeric excesses (ee values) were determined by HPLC analysis using a Shimadzu LC-2030 HPLC. Melting points were determined with a Cole-Parmer instrument and are uncorrected.

Example 1

5-(3-((tert-butyldimethylsilyl)oxy)propyl)furan-3 (2H)-one (11)

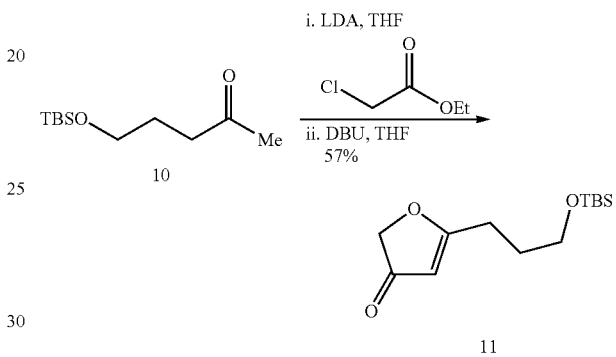

To a solution of diisopropylamine (3.67 mL, 26.2 mmol, 2.2 eq) in THF (23.8 mL, 0.5 M) at −78° C. was added n-butyllithium (10.8 mL, 23.8 mmol, 2.0 eq) dropwise. The solution was stirred for 10 minutes, warmed to −30° C. and stirred for an additional 10 minutes. Then 5-((tert-butyldimethylsilyl)oxy)pentan-2-one (5.15 g, 23.8 mmol, 2.0 eq) was added dropwise, and the temperature was maintained for 30 minutes. The reaction mixture was cooled to −50° C., ethyl chloroacetate (1.27 mL, 11.9 mmol, 1.0 eq) was added, and the mixture was slowly warmed to −30° C. over 5 hours. The mixture was acidified to pH 4-5 with 2 M hydrochloric acid solution and extracted with $Et_2O$ (20 mL×3). The combined organic phases were washed with brine, dried over $Na_2SO_4$ and filtered. The solution was concentrated and used directly without further purification.

To a stirred solution of the crude residue from above in THF (24.3 ml, 0.5 M) at room temperature was added 1,8-diazabicyclo[5.4.0]undec-7-ene (1.81 mL, 12.1 mmol, 1.02 eq) dropwise. Precipitation was observed after about 5 minutes. After stirring for 1 hour, the mixture was quenched by addition of saturated ammonium chloride solution and extracted with $Et_2O$ (30 ml×3). The combined organic layers were washed with brine, dried over $Na_2SO_4$, filtered and concentrated. Purification by FCC (4:1 hexanes:EtOAc) yielded 11 as a colorless oil (1.72 g, 57%).

Data for 11: Rf0.40 (3:1 hexanes:EtOAc); IR (thin film) 2955, 2930, 2886, 2858, 1741, 1704, 1599 cm$^{-1}$; $^1$H NMR (700 MHz, CDCl$_3$) δ 5.48 (s, 1H), 4.49 (s, 2H), 3.67 (t, J=5.6 Hz, 2H), 2.60 (t, J=7.7 Hz, 2H), 1.85 (quintet, J=7.0 Hz, 2H), 0.89 (s, 9H), 0.05 (s, 6H); $^{13}$C NMR (176 MHz, CDCl$_3$) δ 201.6, 194.4, 103.2, 74.4, 60.9, 28.2, 26.5, 25.0, 17.4, −6.2; FIRMS (ESI) calcd for $C_{13}H_{25}O_3Si$ [M+H]: 257.1573, found 257.1568.

Example 2 tert-butyl(3-(4-methoxyfuran-2-yl)propoxy)dimethylsilane (12)

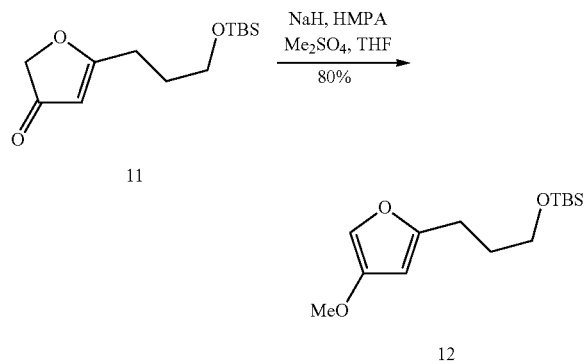

To a slurry of sodium hydride (74.9 mg, 60% dispersion in mineral oil, 1.87 mmol, 3.0 eq) in THF (1.46 mL) at 0° C. was added a solution of furanone 11 (160 mg, 0.624 mmol, 1.0 eq) in THF (0.62 mL) and HMPA (0.32 mL, 1.87 mmol, 3.0 eq). The mixture was stirred at 0° C. for 30 minutes, and then dimethyl sulfate (0.072 mL, 0.749 mmol, 1.2 eq) was added. The reaction mixture was stirred for additional 1.5 hours. Concentrated ammonium hydroxide (1.0 mL) was slowly added to the solution and stirring was continued for 30 minutes. The reaction mixture was extracted with Et$_2$O (4 mL×3). The combined organic phases were washed with brine, dried over Na$_2$SO$_4$ and filtered. The concentrated mixture was filtered through a pad of 1:1 Celite:silica gel, washed with 20 mL hexane, and the light yellow fraction was collected and concentrated to yield furan 12 as a light yellow oil (134.7 mg, 80%).

Data for 12: $R_f$ 0.68 (4:1 hexanes:EtOAc); IR (thin film) 2954, 2931, 2898, 2858, 1622, 1256, 1102 cm$^{-1}$; $^1$H NMR (700 MHz, CDCl$_3$) δ 6.95 (s, 1H), 5.85 (s, 1H), 3.68 (s, 3H), 3.63 (t, J=6.2 Hz, 2H), 2.60 (t, J=7.5 Hz, 2H), 1.83-1.79 (m, 2H), 0.90 (s, 9H), 0.05 (s, 6H); $^{13}$C NMR (176 MHz, CDCl$_3$) δ 155.6, 150.8, 121.2, 99.5, 62.3, 58.0, 301.0, 26.1, 25.0, 18.5, −5.2; HRMS (ESI) calcd for C$_{14}$H$_{27}$O$_3$Si [M+H]: 271.1729, found 271.1728.

Example 3

N-(2-(6-((5-(3-((tert-butyldimethylsilyl)oxy)propyl)-3-methoxyfuran-2-yl)methyl)benzo[d][1,3]dioxol-5-yl)ethyl)-2,2,2-trifluoroacetamide (14)

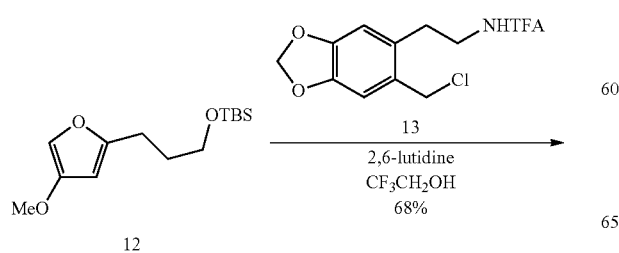

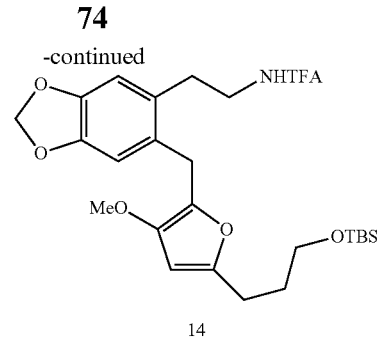

To a solution of furan 12 (850 mg, 3.14 mmol, 1.2 eq) and 2,6-lutidine (0.364 ml, 3.14 mmol, 1.2 eq) in 2,2,2-trifluoroethanol (5.24 mL, 0.5 M) at 0° C. was added benzyl chloride 13 (811.1 mg, 2.62 mmol, 1.0 eq). The mixture was stirred at room temperature for 5 hours. Water (10 mL) was added and the aqueous layer was extracted with ethyl acetate (5 mL×3). The combined organic layers were dried over Na$_2$SO$_4$, filtered and concentrated. Purification by FCC (4:1 hexanes:EtOAc) yielded 14 as a yellow film (962.3 mg, 68%).

Data for 14: $R_f$ 0.55 (4:1 hexanes:EtOAc); IR (thin film) 3316, 2954, 2929, 2857, 1709, 1646, 1554, 1487, 1207, 1163 cm$^{-1}$; $^1$H NMR (700 MHz, CDCl$_3$) δ 6.74 (s, 1H), 6.60 (s, 1H), 6.52 (br, 1H), 5.91 (s, 3H), 3.79 (s, 2H), 3.71 (s, 3H), 3.60 (t, J=6.3 Hz, 2H), 3.42 (q, J=6.3 Hz, 2H), 2.88 (t, J=7.0 Hz, 2H), 2.55 (t, J=7.7 Hz, 2H), 1.77 (quintet, J=7.0 Hz, 2H), 0.88 (s, 9H), 0.02 (s, 6H); $^{13}$C NMR (176 MHz, CDCl$_3$) δ (157.5, 157.3, 157.1, 156.9), 146.7, 146.6, 143.6, 135.4, 130.5, 143.6, 135.4, 130.5, 128.8, (118.4, 116.8, 115.2, 113.5), 110.7, 109.7, 101.1, 98.5, 62.3, 59.6, 40.6, 31.9, 31.0, 28.7, 26.1, 25.1, 18.5, −5.2; HRMS (ESI) calcd for C$_{26}$H$_{37}$F$_3$NO$_6$Si [M+H]: 544.2342, found 544.2330.

Example 4

2,2,2-trifluoro-N-(2-(6-((5-(3-hydroxypropyl)-3-methoxyfuran-2-yl)methyl)benzo[d][1,3]dioxol-5-yl)ethyl)acetamide (22)

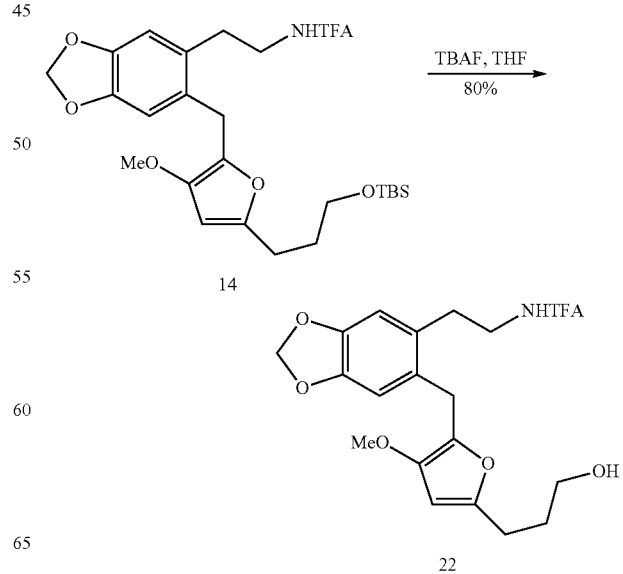

To a solution of silyl ether 14 (500 mg, 0.920 mmol, 1.0 eq) in THF (9.20 mL, 0.1 M) at 0° C. was added 1M tetrabutylammonium fluoride solution (2.76 ml, 3.0 eq). The mixture was warmed up to room temperature and stirred for 5 hours. The reaction was quenched with water (10 mL) and extracted with ethyl acetate (20 mL×3). The combined organic layers were washed with brine, dried over $Na_2SO_4$, filtered and concentrated. Purification by FCC (1:1 $CH_2Cl_2$: EtOAc) afforded 22 as a white solid (317.5 mg, 80%).

Data for 22: mp 72-73° C.; $R_f$ 0.26 (1:1 hexanes:EtOAc); IR (thin film) 3330, 2955, 2931, 2897, 2859, 1715, 1677, 1580, 1488, 1209, 1162 $cm^{-1}$; $^1$H NMR (700 MHz, $CDCl_3$) δ 6.73 (s, 1H), 6.71 (br, 1H), 6.60 (s, 1H), 5.94 (s, 1H), 5.91 (s, 2H), 3.79 (s, 2H), 3.71 (s, 3H), 3.64 (t, J=6.3 Hz, 2H), 3.42 (q, J=6.3 Hz, 2H), 2.88 (t, J=7.0 Hz, 2H), 2.60 (t, J=7.0 Hz, 2H), 1.82 (sept, J=6.3 Hz, 2H); $^{13}$C NMR (176 MHz, $CDCl_3$) δ (157.6, 157.4, 157.2, 157.0), 152.9, 146.7, 146.6, 143.6, 135.7, 130.4, 128.8, (118.5, 116.8, 115.2, 113.6), 110.7, 109.7, 101.1, 98.8, 62.1, 59.5, 40.6, 31.9, 31.0, 28.7, 25.0; HIRMS (ESI) calcd for $C_{20}H_{23}F_3NO_6$ [M+H]: 430.1477, found 430.1474.

Example 5

3-(4-methoxy-5-((6-(2-(2,2,2-trifluoroacetamido)ethyl)benzo[d][1,3]dioxol-5-yl)methyl) furan-2-yl) propyl methanesulfonate (15)

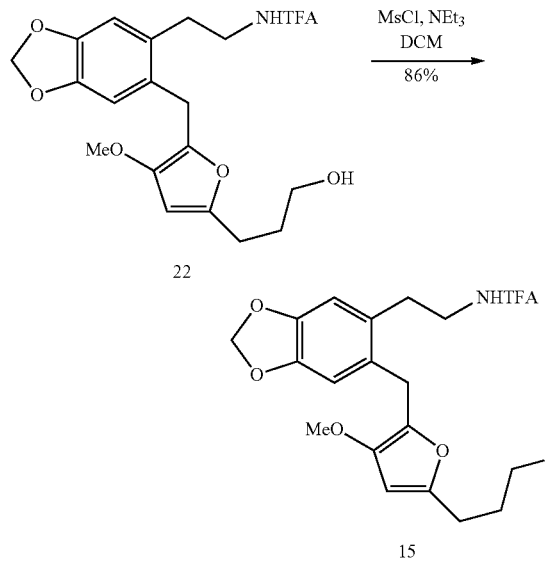

To a solution of alcohol 22 (468 mg, 1.09 mmol, 1.0 eq) in $CH_2Cl_2$ (5.45 mL, 0.2 M) at 0° C. was added $NEt_3$ (0.380 mL, 2.72 mmol, 2.5 eq). The reaction mixture was stirred for 10 minutes, after which methanesulfonyl chloride (0.169 mL, 2.18 mmol, 2.0 eq) was added dropwise. The solution was slowly warmed to room temperature and stirred for additional 1 hour. Water (5 mL) was added and the mixture was extracted with $CH_2Cl_2$ (10 mL×3). The combined organic layers were washed with brine, filtered and dried over $Na_2SO_4$. Purification by FCC (1:1 hexanes:EtOAc) gave mesylate 15 as a pale yellow solid (476.8 mg, 86%).

Data for 15: mp 78-79° C.; $R_f$ 0.41 (1:1 hexanes:EtOAc); IR (thin film) 3336, 2919, 2850, 1717, 1645, 1555, 1487, 1353, 1173 $cm^{-1}$; $^1$H NMR (700 MHz, $CDCl_3$) δ 6.75 (br, 1H), 6.70 (s, 1H), 6.60 (s, 1H), 5.98 (s, 1H), 5.89 (s, 2H), 4.20 (t, J=6.3 Hz, 2H), 3.79 (s, 2H), 3.70 (s, 3H), 3.42 (q, J=6.3 Hz, 2H), 2.96 (s, 3H), 2.88 (t, J=7.7 Hz, 2H), 2.63 (t, J=7.0 Hz, 2H), 2.00 (quintet, J=7.0 Hz, 2H); $^{13}$C NMR (176 MHz, $CDCl_3$) δ (157.6, 157.3, 157.1, 156.9), 151.2, 146.7, 146.6, 143.7, 136.2, 130.4, 128.8, (118.5, 116.8, 115.2, 113.6), 110.5, 109.7, 101.1, 99.5, 69.0, 59.5, 40.7, 37.4, 31.9, 28.5, 27.7, 24.5; HRMS (ESI) calcd for $C_{21}H_{25}F_3NOsS$ [M+H]: 508.1253, found 508.1242.

Example 6

$3^3$-methoxy-7-aza-1(5,6)-benzo[d][1,3]dioxola-3(2,5)-furanacyclononaphane (5)

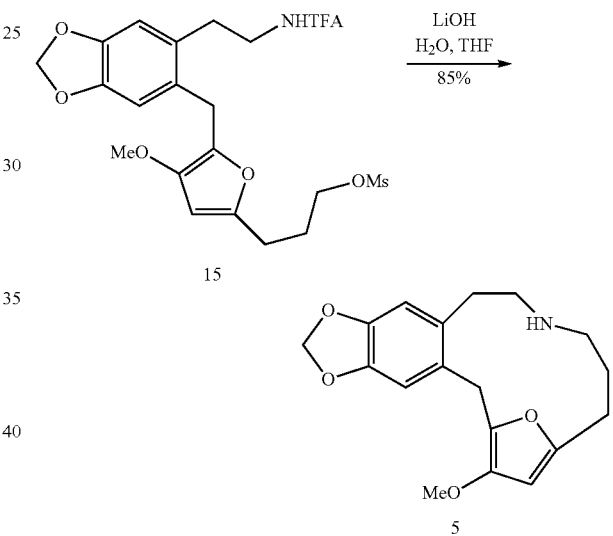

To a solution of mesylate 15 (21.0 mg, 0.0414 mmol, 1.0 eq) in THF (0.83 mL, 0.05 M) was added lithium hydroxide (3.0 mg, 0.124 mmol, 3.0 eq) and water (0.04 mL, 1.0 M). The mixture was heated to reflux and stirred for 36 hours. The reaction was cooled to room temperature, diluted with water (3 mL) and extracted with ethyl acetate (4 mL×3). The combined organic layers were washed with brine, dried over $Na_2SO_4$, filtered and concentrated. Purification by FCC (10:1 $CH_2Cl_2$:MeOH with 10% $NH_4OH$) yielded macrocycle 5 as a pale yellow film (12.1 mg, 85%).

Data for 5: $R_f$ 0.26 (10:1 $CH_2Cl_2$:MeOH with 10% $NH_4OH$); IR (thin film) 3327, 2936, 1641, 1503, 1485 $cm^{-1}$; $^1$H NMR (400 MHz, $CDCl_3$) δ 6.73 (s, 1H), 6.69 (s, 1H), 5.89 (s, 3H), 3.84 (s, 2H), 3.69 (s, 3H), 2.82 (t, J=5.6 Hz, 4H), 2.65 (t, J=7.0 Hz, 2H), 2.54 (t, J=5.6 Hz, 2H), 1.78-1.72 (m, 2H); $^{13}$C NMR (176 MHz, $CDCl_3$) δ 152.5, 146.6, 145.8, 143.3, 135.6, 132.7, 130.2, 110.8, 109.5, 101.0, 99.3, 59.4, 49.0, 47.5, 31.8, 30.3, 28.2, 25.9; HRMS (ESI) calcd for $C_{18}H_{22}NO_4$ [M+H]: 316.1549, found 316.1548.

Example 7

(±)-Cephalotaxinone (2)

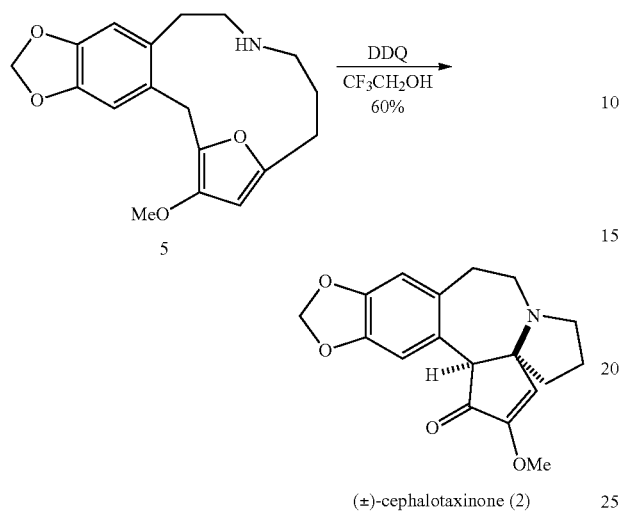

To a solution of furan 5 (8.2 mg, 0.026 mmol, 1.0 eq) in 2,2,2-trifluoroethanol (0.26 mL, 0.1 M) was added DDQ (5.9 mg, 0.026 mmol, 1.0 eq). The mixture was warmed to 50° C. and stirred for 14 hours. The reaction mixture was quenched by saturated sodium bisulfite and sodium bicarbonate solution, and then extracted with ethyl acetate (3 mL×5). The combined organic phases were dried over $Na_2SO_4$, filtered and evaporated. Purification by FCC (10:1 $CH_2Cl_2$:MeOH with 10% $NH_4OH$) gave (±)-2 as a pale yellow film (5.0 mg, 60%).

Data for 2: $R_f$ 0.74 (10:1 $CH_2Cl_2$:MeOH with 10% $NH_4OH$); IR (thin film) 2925, 1724, 1625, 1487, 1230, 1103, 1037, 803 cm$^{-1}$; $^1$H NMR (700 MHz, $CDCl_3$) δ 6.70 (s, 1H), 6.64 (s, 1H), 6.40 (s, 1H), 5.92 (d, J=1.4 Hz, 1H), 5.91 (d, J=1.4 Hz, 1H), 3.80 (s, 1H), 3.53 (s, 1H), 3.11-3.08 (m, 1H), 2.93-2.89 (m, 1H), 2.71-2.67 (m, 1H), 2.54-2.51 (m, 1H), 2.45-2.43 (m, 2H), 2.11-2.08 (m, 1H), 1.98-1.95 (m, 1H), 1.89-1.85 (m, 2H); $^{13}$C NMR (176 MHz, $CDCl_3$) δ 201.0, 158.3, 147.4, 146.4, 130.7, 128.6, 123.9, 112.6, 110.4, 101.2, 65.5, 60.8, 57.4, 53.0, 47.8, 39.0, 31.5, 20.1; HRMS (ESI) calcd for $C_{18}H_{20}NO_4$ [M+H]: 314.1392, found 314.1379.

Example 8

(−)-Cephalotaxine (1) and (+)-Cephalotaxinone (2)

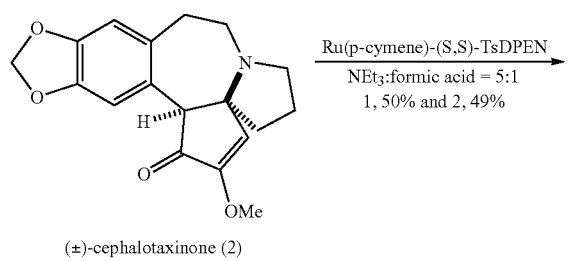

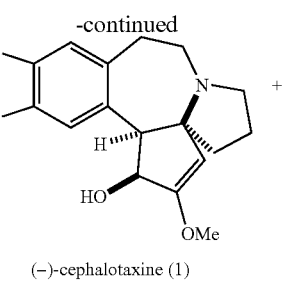

(−)-cephalotaxine (1)

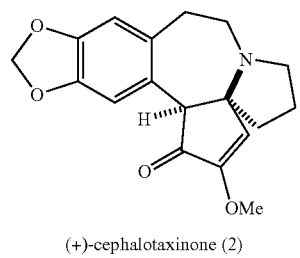

(+)-cephalotaxinone (2)

A thick walled reaction tube containing racemic cephalotaxinone (13.0 mg, 0.0415 mmol, 1.0 eq) was evacuated and backfilled with argon. Then a solution of freshly prepared Ru(p-cymene)-(S,S)-TsDPEN catalyst (1.0 mg, 4 mol %) in 5:1 $NEt_3$: formic acid mixture (0.166 mL, 0.25 M) was added. (Methods for preparing the catalyst are known to persons of ordinary skill in the art, but additional information can be found in Haack, et al. *Angew. Chem. Int. Ed. Engl.* 1997, vol. 36, 285-288, incorporated herein by reference.) The reaction mixture was sealed, heated to 40° C. and stirred for 48 hours. The mixture was cooled to room temperature, diluted with saturated sodium bicarbonate solution (2 mL) and extracted with ethyl acetate (4 mL×3). The combined organic layers were washed with brine, dried over $Na_2SO_4$, filtered and evaporated. Purification by FCC (50:1 to 10:1 $CH_2Cl_2$:MeOH with 10% $NH_4OH$) gave (−)-1 as a pale yellow film (6.5 mg, 50%, ee.=97.34%) and (+)-2 a pale yellow film (6.4 mg, 49%, ee.=97.26%).

Data for 1: $R_f$ 0.34 (15:1 $CH_2Cl_2$:MeOH with 10% $NH_4OH$); IR (thin film) 3376, 2933, 2883, 1651, 1503, 1487, 1224, 1037 cm$^{-1}$; $^1$H NMR (700 MHz, $CDCl_3$) δ 6.68 (s, 1H), 6.65 (s, 1H), 5.91 (d, J=2.5 Hz, 2H), 4.93 (s, 1H), 4.77 (dd, J=9.4, 3.4 Hz, 1H), 3.73 (s, 3H), 3.68 (d, J=9.4 Hz, 1H), 3.37-3.32 (m, 1H), 3.08 (td, J=9.0, 4.3 Hz, 1H), 2.92 (td, J=11.6, 7.2 Hz, 1H), 2.61-2.56 (m, 2H), 2.36 (dd, J=14.5, 7.0 Hz, 1H), 2.04-1.99 (m, 1H), 1.89-1.85 (m, 1H), 1.77-1.71 (m, 2H), 1.61 (d, J=3.4 Hz, 1H); $^{13}$C NMR (176 MHz, $CDCl_3$) δ 160.7, 147.1, 146.3, 134.5, 128.2, 112.8, 110.5, 101.1, 97.9, 73.5, 70.7, 58.3, 57.3, 54.1, 48.7, 43.9, 31.9, 20.6; HRMS (ESI) calcd for $C_{18}H_{22}NO_4$ [M+H]: 316.1549, found 316.1551; $[\alpha]_D^{20}$=−172.1° (c 0.21, $CHCl_3$); HPLC (DAICEL, Chiralcel OD-RH, 30:70 $H_2O$:MeOH with 2% $NH_4OH$, 0.5 mL/min, 25° C.): $t_R$[min]= 12.44 (98.67%), 14.42 (1.33%), ee.=97.34%.

Example 9

(1S,3aR,14bS)-2-methoxy-1,5,6,8,9,14b-hexahydro-4H-[1,3]dioxolo[4',5':4,5]benzo[1,2-d]cyclopenta[b]pyrrolo[1,2-a]azepin-1-yl (R)-2-((E)-4-(benzyloxy)-4-methylpent-2-en-1-yl)-4-oxooxetane-2-carboxylate (23)

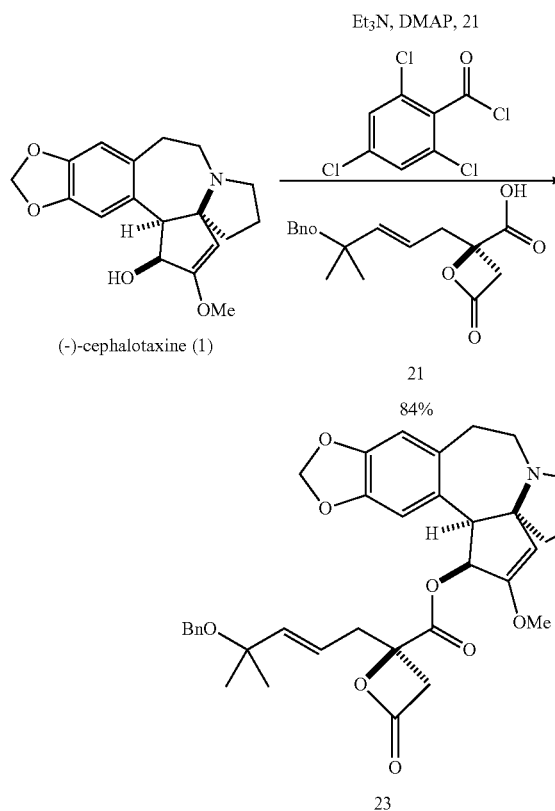

To a solution of β-lactone 21 (10.0 mg, 0.033 mmol, 2.00 eq) and NEt₃ (0.015 mL, 0.11 mmol, 6.6 eq) in CH₂C₂ (0.12 mL) was added 2,4,6-trichlorobenzoyl chloride (5.7 μL, 0.036 mmol, 2.20 eq). The resulting solution was stirred for 1 hour and then transferred via syringe to a solution of cephalotaxine (1) (5.2 mg, 0.017 mmol, 1.00 eq) and N,N-dimethylaminopyridine (2.2 mg, 0.018 mmol, 1.10 eq) in CH₂Cl₂ (0.12 mL). This solution was then stirred for 3 hours and directly loaded onto a pH 7.0 buffered silica gel column. Purification by FCC (30:1 CH₂Cl₂:MeOH with 10% NH₄OH) afforded 23 as a light yellow oil (8.5 mg, 84%).

Data for 23: $R_f$ 0.37 (20:1 CH₂Cl₂:MeOH with 10% NH₄OH); IR (neat film) 2931, 2807, 1841, 1748, 1655, 1507, 1224 cm⁻¹; ¹H NMR (700 MHz, CDCl₃) δ 7.32-7.24 (m, 5H), 6.60 (s, 1H), 6.59 (s, 1H), 5.86 (d, J=12.2 Hz, 3H), 5.71 (d, J=16.1 Hz, 1H), 5.49-5.45 (m, 1H), 5.08 (s, 1H), 4.30 (s, 2H), 3.81 (d, J=9.7 Hz, 1H), 3.69 (s, 3H), 3.10-3.06 (m, 2H), 2.98 (d, J=16.5 Hz, 1H), 2.94-2.92 (m, 1H), 2.63 (d, J=16.7 Hz, 1H), 2.60-2.56 (m, 3H), 2.41 (dd, J=14.4, 7.1 Hz, 1H), 2.35 (dd, J=14.4, 6.7 Hz, 1H), 2.06-2.01 (m, 1H), 1.91-1.88 (m, 1H), 1.77-1.73 (m, 2H), 1.32 (s, 6H); ¹³C NMR (176 MHz, CDCl₃) δ 168.1, 165.5, 156.6, 147.1, 146.0, 143.1, 139.7, 133.6, 128.4, 127.90, 127.6, 127.4, 127.3, 120.5, 113.4, 109.9, 101.3, 101.2, 75.9, 75.6, 75.3, 70.8, 65.1, 57.4, 56.5, 54.1, 48.7, 46.2, 43.6, 37.7, 31.6, 26.5, 26.3, 20.5; HRMS (ESI) calcd for C₃₅H₄₀NO₈ [M+H]: 602.2754, found 602.2742.

Example 10

1-((1S,3aR,14bS)-2-methoxy-1,5,6,8,9,14b-hexahydro-4H-[1,3]dioxolo[4',5':4,5]benzo[1,2-d]cyclopenta[b]pyrrolo[1,2-a]azepin-1-yl) 4-methyl (R)-2-((E)-4-(benzyloxy)-4-methylpent-2-en-1-yl)-2-hydroxysuccinate (24)

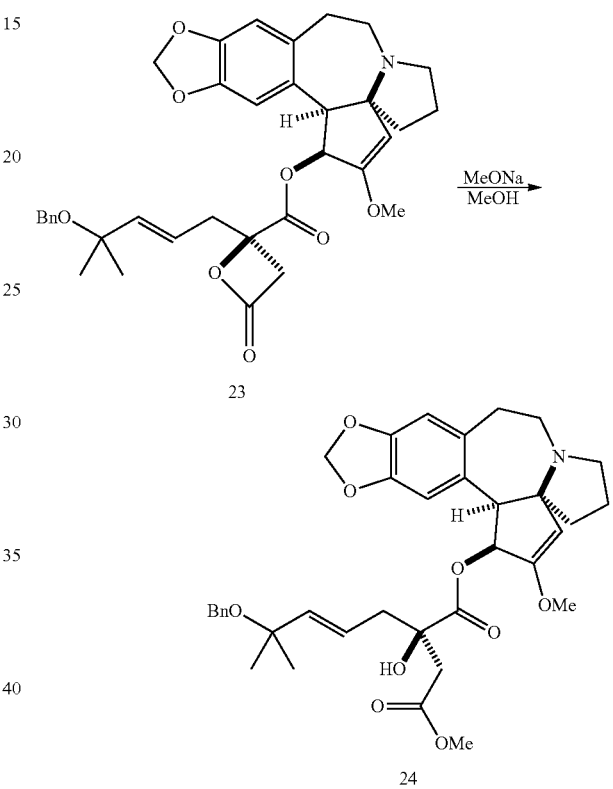

To a solution of β-lactone 23 (5.6 mg, 0.0092 mmol, 1.0 eq) in MeOH (0.092 mL, 0.1 M) was added a freshly prepared solution of 0.5 M NaOMe in MeOH (0.020 mL, 0.011 mmol, 1.1 eq). After 10 minutes the solution was quenched with saturated ammonia chloride solution (2 mL) diluted with CH₂Cl₂ (2 mL). The phases were separated and the aqueous phase was extracted with CH₂Cl₂ (3 mL×3). The combined organic phases were dried over Na₂SO₄, filtered and concentrated. The crude ester 24 was used directly in next step without further purification.

Data for 24: $R_f$ 0.63 (15:1 CH₂Cl₂:MeOH with 10% NH₄OH); IR (neat film) 3520, 2927, 1745, 1655, 1504, 1487, 1364, 1038, 933, 748 cm⁻¹; ¹H NMR (700 MHz, CDCl₃) δ 7.34-7.23 (m, 5H), 6.61 (s, 1H), 6.55 (s, 1H), 5.94 (d, J=9.7 Hz, 1H), 5.85 (d, J=13.5 Hz, 2H), 5.61 (d, J=15.8 Hz, 1H), 5.51-5.47 (m, 1H), 5.05 (s, 1H), 4.32 (s, 2H), 3.77 (d, J=9.7 Hz, 1H), 3.67 (s, 3H), 3.58 (s, 3H), 3.47 (s, 1H), 3.14-3.11 (m, 2H), 2.97-2.92 (m, 1H), 2.59 (m, 2H), 2.39 (dd, J=12.6, 5.2 Hz, 1H), 2.29 (d, J=16.3 Hz, 1H), 2.23-2.16 (m, 2H), 2.04-2.01 (m, 1H), 1.96 (d, J=16.1 Hz, 1H), 1.90 (m, 1H), 1.76-1.74 (m, 2H), 1.33 (d, J=4.9 Hz, 6H); ¹³C NMR (176 MHz, CDCl₃) δ 173.5, 170.4, 146.8, 145.9, 141.0, 139.7, 128.3, 127.5, 127.1, 122.9, 112.9, 109.7, 100.9, 100.2, 75.3, 75.25, 74.61, 65.15, 57.49, 56.16, 54.15, 51.80, 48.81, 43.56, 41.92, 41.77, 31.63, 26.69, 26.52, 20.50; HRMS (ESI) calcd for $C_{36}H_{44}NO_9$ [M+H]: 634.3016, found 634.3007.

Example 11

(−)-Homoharringtonine

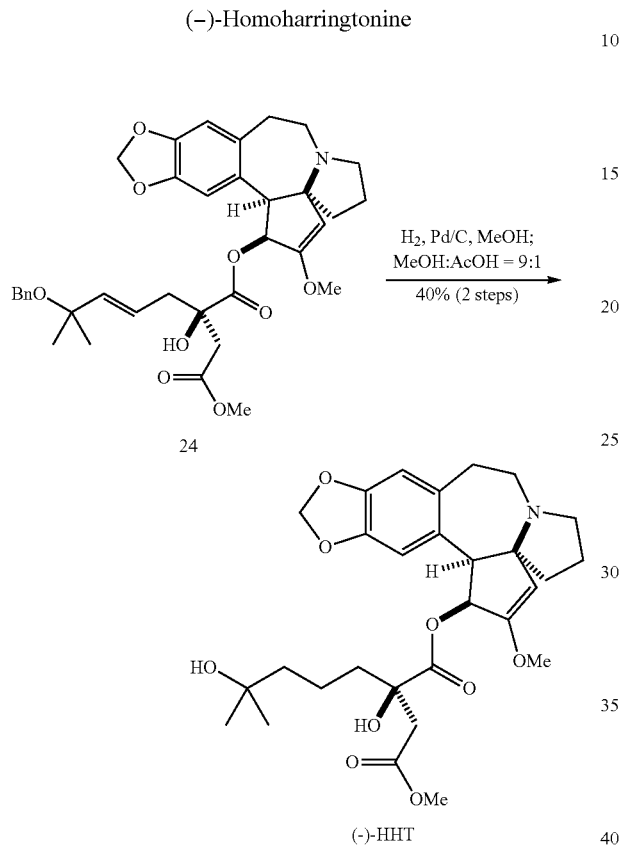

To a solution of crude allylic benzyl ether 24 (7.0 mg, 0.011 mmol, 1.0 eq) in MeOH (0.11 mL) was added 10% Pd/C (1.4 mg, 20% by wt). A $H_2$ balloon was applied to the vessel and the suspension was stirred at room temperature for 48 hours. Glacial acetic acid (11 μL) was added via syringe and the solution was stirred under $H_2$ for 22 hours. Further 10% Pd/C (0.7 mg, 10% by wt) and glacial acetic acid (11 μL) were added and the suspension was stirred under $H_2$ for 48 hours. The mixture was filtered through a plug of celite and the solvent was evaporated. Purification by FCC (20:1 $CH_2Cl_2$:MeOH with 10% $NH_4OH$) afforded (−)-HHT as a colorless film (2.4 mg, 40% over 2 steps).

Data for (−)-HHT: $R_f$ 0.38 (10:1 $CH_2Cl_2$:MeOH with 10% $NH_4OH$); IR (neat film) 2920, 2852, 1746, 1654, 1505, 1488, 1366, 1225 cm$^{-1}$; $^1$H NMR (700 MHz, CDCl$_3$) δ 6.62 (s, 1H), 6.54 (s, 1H), 6.00 (d, J=10.1 Hz, 1H), 5.87 (d, J=2.3 Hz, 2H), 5.05 (s, 1H), 3.78 (d, J=9.8 Hz, 1H), 3.68 (s, 3H), 3.57 (s, 3H), 3.53 (s, 1H), 3.13-3.08 (m, 2H), 2.96-2.93 (m, 1H), 2.60-2.57 (m, 2H), 2.38 (dd, J=14.4, 6.8 1H), 2.26 (d, J=16.5 Hz, 1H), 2.06-2.01 (m, 1H), 1.91 (d, J=16.3 Hz, 1H), 1.91-1.89 (m, 1H), 1.77-1.74 (m, 2 H), 1.42-1.38 (m, 5H), 1.27 (s, 1H), 1.19 (d, J=3.4 Hz, 6H); $^{13}$C NMR (176 MHz, CDCl$_3$) δ 174.1, 170.6, 157.8, 146.8, 146.0, 133.5, 128.5, 112.8, 128.8, 109.8, 101.0, 100.4, 74.9, 74.8, 71.1, 70.7, 57.6, 56.0, 54.1, 51.7, 48.8, 43.9, 43.5, 42.7, 39.3, 31.5, 29.5, 29.1, 20.4, 18.0; HRMS (ESI) calcd for $C_{29}H_{40}NO_9$ (M+H) 545.2703 found 545.2703; $[\alpha]_D^{20}$=−110.5° (c 0.24, CHCl$_3$).

Example 12

(±)-Cephalotaxinone (2)

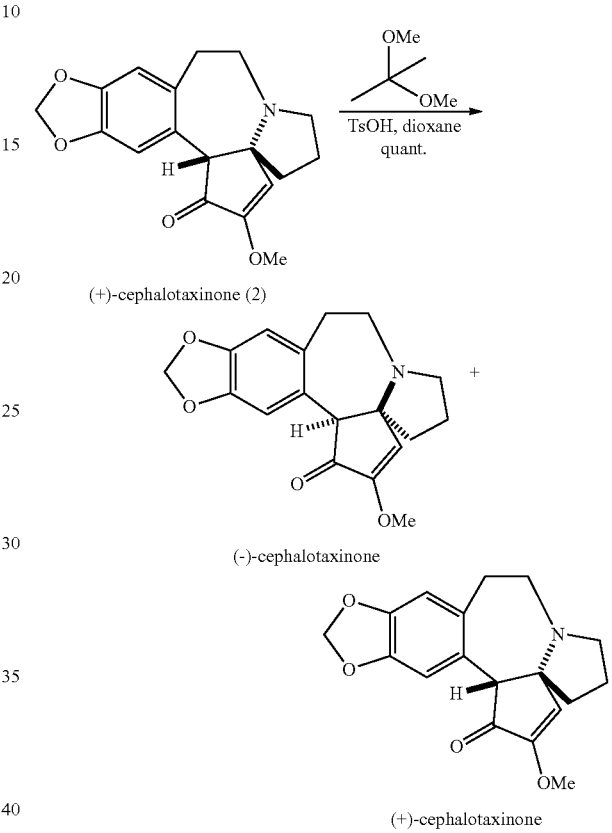

To a solution of (+)-2 (1.0 mg, 0.0032 mmol, ee.=99.0%, 1.0 eq) in dioxane (0.32 mL, 0.01 M) and 2,2-dimethoxypropane (0.32 mL, 0.01 M) in thick walled reaction tube was added TsOH.H$_2$O (2.4 mg, 0.013 mmol, 4.0 eq). The suspension was heated to reflux and kept stirring for 3 days. The reaction mixture was cooled to room temperature, quenched with saturated sodium bicarbonate solution (2 mL) and extracted with ethyl acetate (3 mL×3). The combined organic layers were washed with brine, dried over Na$_2$SO$_4$, filtered and concentrated. Purification by FCC (50:1 CH$_2$Cl$_2$:MeOH with 10% NH$_4$OH) afforded (±)-2 as a pale yellow film (1.0 mg, 100%, ee.=5.0%).

Example 13

The cell line panel may include the NCI 60 standard cancer cell lines, HL-60 (a human acute promyelocytic leukemia cell line), a human T cell leukemia cell line, a Mantle cell lymphoma cell line, a human B cell lymphoma, a human acute lymphoblastic T-cell line, a human neuroblastoma cell line, PC9, H1650, H1975, H2030, H3255 (all human non-small cell lung cancer cell lines), a sarcoma cell line, HTB-15 (a human glioblastoma cell line), A431 (a human epithelial carcinoma cell line), HeLa (a human cervical adenocarcinoma cell line) and various bacterial strains. Cell lines are typically grown at 37° C. in a 5% $CO_2$ incubator using standard culture medium, such as RPMI 1640 supplemented with 10% bovine calf serum, 2 mM glutamine, 100 IU/ml of penicillin, and 100 .mu.g/ml of streptomycin or as recommended by the ATCC.

The assay used for the cytotoxicity evaluation is based on the dye resazurin and commercially sold as Alamar Blue (Serotec Ltd, USA). Cells are seeded at densities ranging from 250 to 20,000 cells in 45 µL of medium to compound containing plates and incubated for 72 hours at 37° C. in a 5% $CO_2$ incubator; at which time 5 µL of the Alamar Blue reagent is added and the cells are further incubated for another 24 hours, before the fluorescence intensity is read. The assays are performed on a fully automated linear track robotic platform using several integrated peripherals for plate handling, liquid dispensing, and fluorescence detection. Screening data files from the imaging system are analyses and curve fitting is performed on all the compounds tested.

VI. Exemplary Embodiments

The following numbered paragraphs illustrate exemplary embodiments of the disclosed technology.

Paragraph 1. A compound having a formula selected from

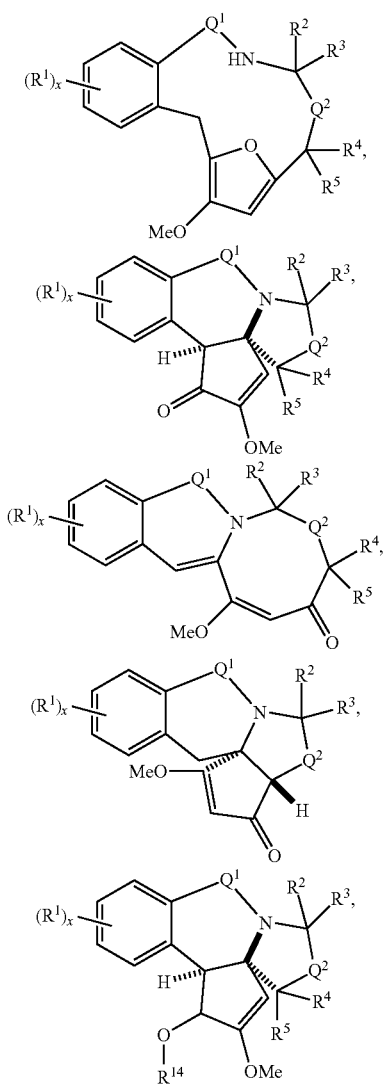

-continued

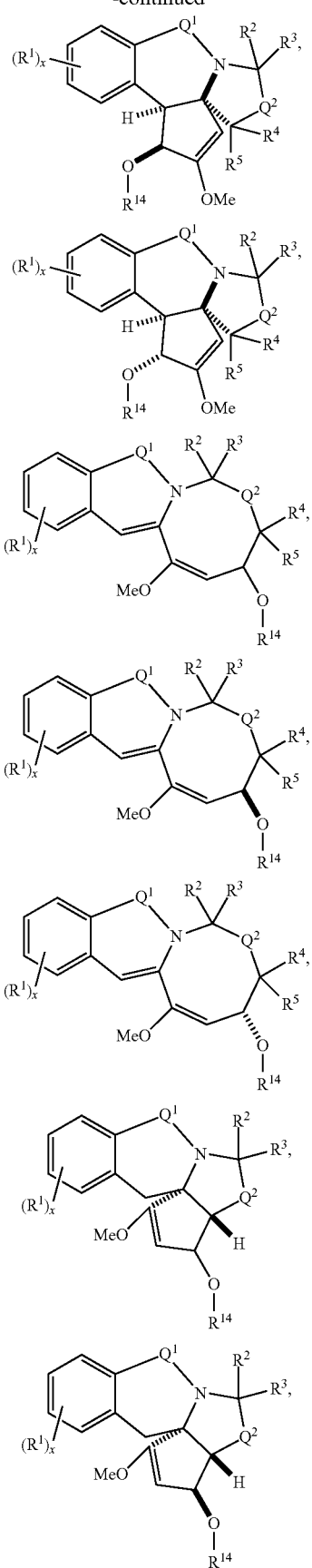

85

-continued

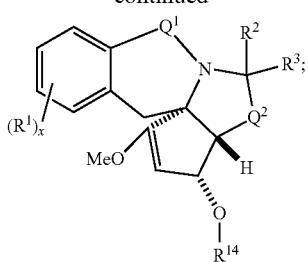

or a salt, solvate, N-oxide, prodrug, enantiomer, or diastereomer thereof, wherein:

x is from 0 to 4;

each R¹ independently is hydroxyl, halogen, aliphatic, alkoxy, haloalkyl, amino, protected amino, carboxylic ester, or two R¹s, together with the atoms to which they are attached, form an aryl or heterocyclyl;

if present, each of R², R³, R⁴ and R⁵ independently is H, halogen, aliphatic, hydroxyalkyl, protected hydroxyalkyl, aryl, heteroaryl, hydroxyl, protected hydroxyl, haloalkyl, amino, protected amino, carboxylic ester, or two of R², R³, R⁴ and R⁵ that are attached to the same carbon together form =O or =S;

if present, R¹⁴ is H, aliphatic, acyl, aryl, or heterocyclyl; and each of Q¹ and Q² independently is aliphatic;

and wherein the compound is not

86

-continued

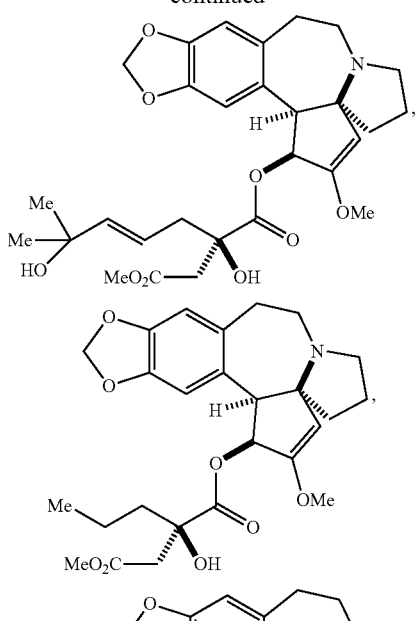

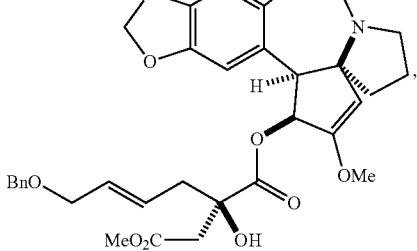

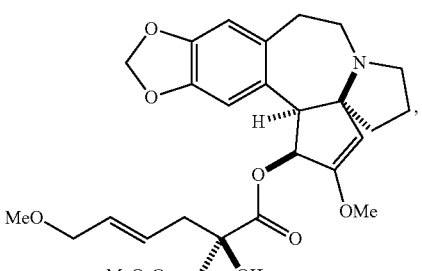

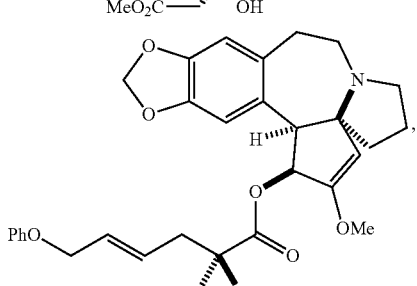

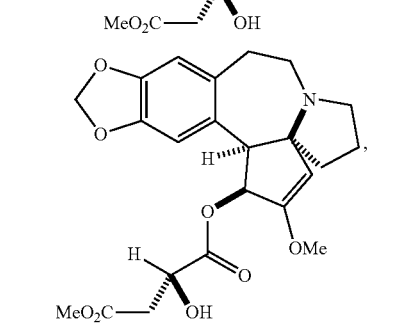

87

-continued

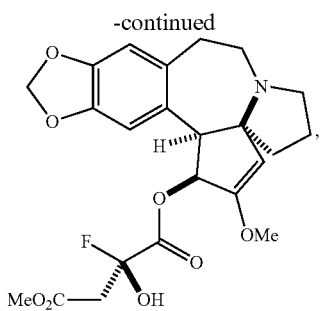

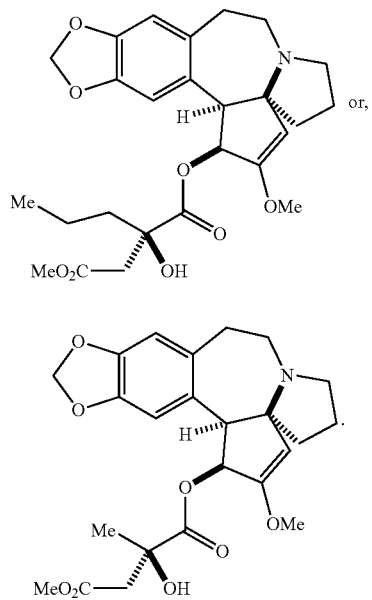

Paragraph 2. The compound of paragraph 1, wherein x is 2, 3, or 4.

Paragraph 3. The compound of paragraph 1 or paragraph 2, wherein each $R^1$ independently is hydroxyl, halogen, alkyl, alkoxy, haloalkyl, or two R's, together with the atoms to which they are attached, form an aryl or heterocyclyl;

Paragraph 4. The compound of any one of paragraphs 1-3, wherein two $R^1$s together with the atoms to which they are attached, form an aryl or heterocyclyl ring.

Paragraph 5. The compound of paragraph 4, wherein the heterocyclyl ring is a 5- or 6-membered heteroaryl.

Paragraph 6. The compound of paragraph 5, wherein the 5- or 6-membered heteroaryl is a pyridinyl, imidazolyl, pyrazolyl, pyrrolyl, oxazolyl, thiazolyl, furanyl, or thiophenyl.

Paragraph 7. The compound of paragraph 4, wherein the heterocyclyl is a 5- or 6-membered non-aromatic heterocyclyl.

Paragraph 8. The compound of paragraph 7, wherein the 5- or 6-membered non-aromatic heterocyclyl is 1,3-dioxole, 1,4-dioxine, 2,3-dihydro-1,4-dioxine, 1,4-oxazine, or 3,4-dihydro-1,4-oxazine.

Paragraph 9. The compound of any one of paragraphs 1-8, wherein the

88

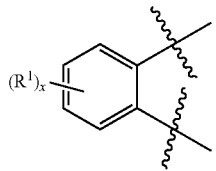

moiety is

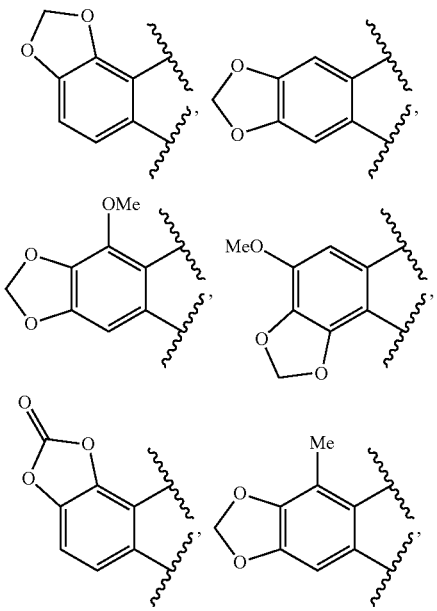

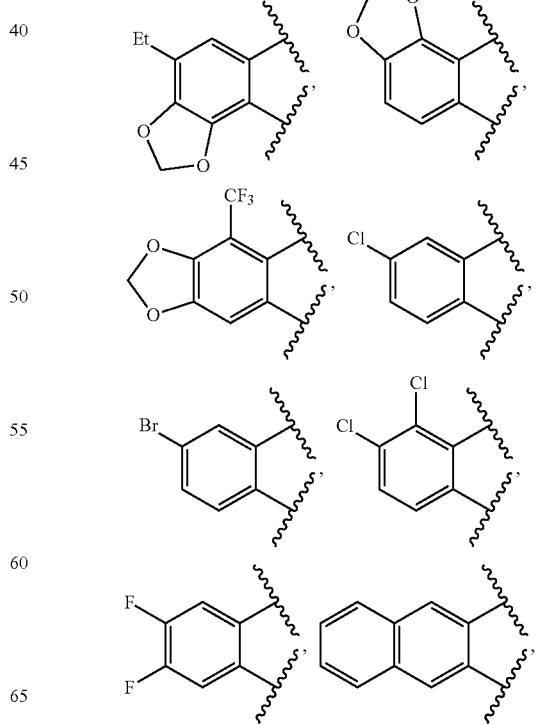

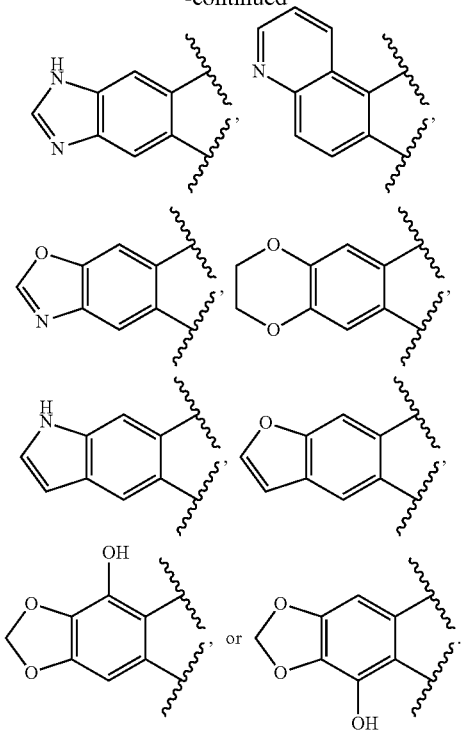

Paragraph 10. The compound of any one of paragraphs 1-9, wherein each of Q and $Q^2$ independently is alkyl.

Paragraph 11. The compound of any one of paragraphs 1-10, wherein $Q^1$ is $C_{1-2}$alkyl.

Paragraph 12. The compound of paragraph 11, wherein $Q^1$ is —$CH_2$— or —$CH_2CH_2$—.

Paragraph 13. The compound of paragraph 11, wherein $Q^1$ is substituted with 1, 2, 3, or 4 substituents from halogen, alkyl, hydroxyalkyl, protected hydroxyalkyl, =O, =S, aryl, hydroxyl, protected hydroxyl, haloalkyl, amino, protected amino, carboxylic ester, or a combination thereof.

Paragraph 14. The compound of paragraph 12, wherein $Q^1$ is substituted with 1, 2, 3, or 4 substituents from halogen, alkyl, hydroxyalkyl, protected hydroxyalkyl, =O, =S, aryl, hydroxyl, protected hydroxyl, or a combination thereof.

Paragraph 15. The compound of any one of paragraphs 10-14, wherein $Q^1$ is $C_1$alkyl.

Paragraph 16. The compound of paragraph 15, wherein $Q^1$ is substituted with methyl, ethyl, hydroxyl, phenyl, hydroxyethyl, hydroxypropyl, or a protected derivative thereof.

Paragraph 17. The compound of any one of paragraph 10-14, wherein $Q^1$ is $C_2$alkyl.

Paragraph 18. The compound of paragraph 17, wherein $Q^1$ is substituted with methyl, ethyl, =O, =S, hydroxyl, phenyl, hydroxyethyl, hydroxypropyl, or a protected derivative thereof.

Paragraph 19. The compound of any one of paragraphs 1-18, wherein the

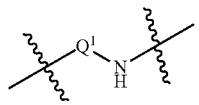

moiety is

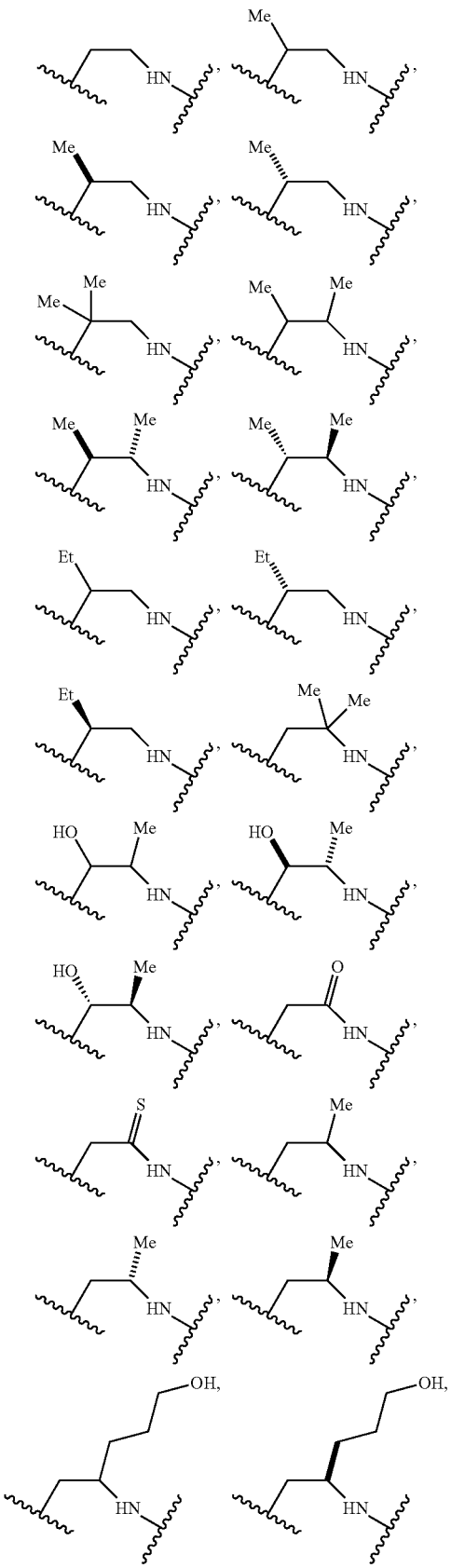

-continued

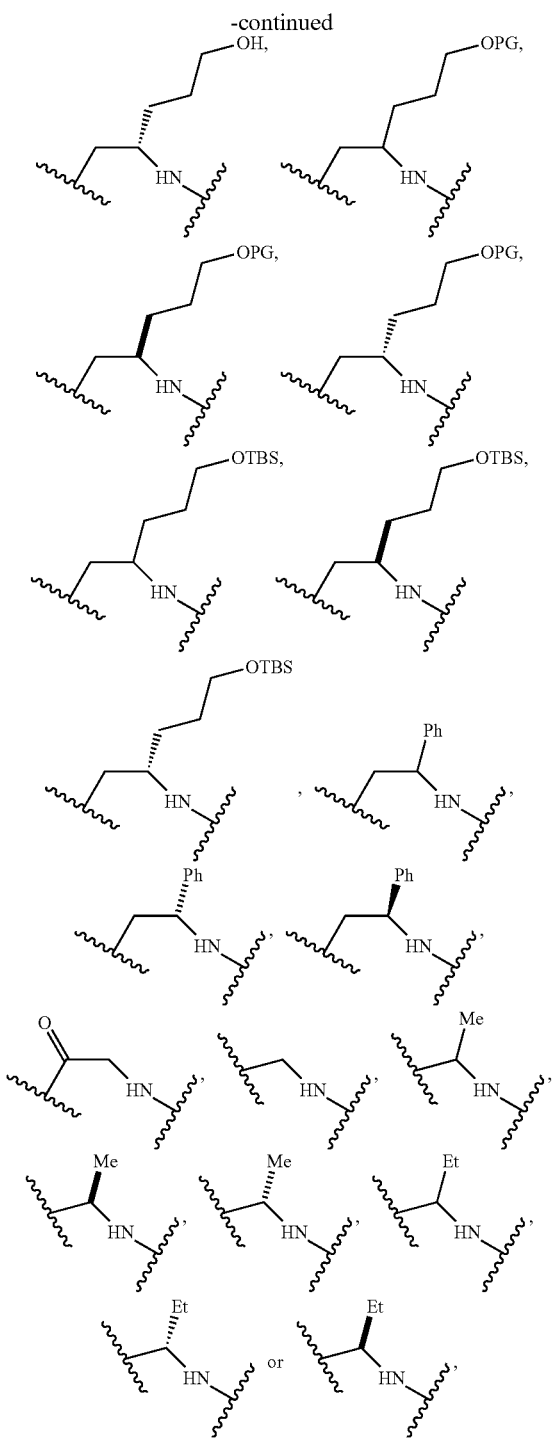

wherein PG is a hydroxyl protecting group.

Paragraph 20. The compound of paragraph 19, wherein PG is methoxymethyl (MOM), tert-butyl, iso-propyl, tert-butyldimethylsilyl (TBS or TBDMS), trimethylsilyl (TMS), triethylsilyl (TES), tert-butyldiphenylsilyl (TBDPS), or tri-isopropylsilyl (TIPS).

Paragraph 21. The compound of any one of paragraphs 1-20, wherein $Q^2$ is $C_{1-2}$alkyl.

Paragraph 22. The compound of paragraph 21, wherein $Q^2$ is —$CH_2$— or —$CH_2CH_2$—.

Paragraph 23. The compound of paragraph 21, wherein $Q^2$ is substituted with 1, 2, 3, or 4 substituents selected from halogen, alkyl, hydroxyalkyl, protected hydroxyalkyl, =O, =S, aryl, hydroxyl, protected hydroxyl, haloalkyl, amino, protected amino, carboxylic ester, or a combination thereof.

Paragraph 24. The compound of paragraph 23, wherein $Q^2$ is substituted with 1, 2, 3, or 4 substituents selected from halogen, alkyl, hydroxyalkyl, protected hydroxyalkyl, =O, =S, aryl, hydroxyl, protected hydroxyl, or a combination thereof.

Paragraph 25. The compound of any one of paragraphs 21-24, wherein $Q^2$ is $C_1$alkyl.

Paragraph 26. The compound of any one of paragraphs 21-24, wherein $Q^2$ is $C_2$alkyl.

Paragraph 27. The compound of paragraph 25 or paragraph 26, wherein $Q^2$ is substituted with Cl, methyl, ethyl, =O, =S, hydroxyl, protected hydroxyl, hydroxyethyl, hydroxypropyl, or a protected derivative thereof, or a combination thereof.

Paragraph 28. The compound of any one of paragraphs 1-27, wherein each of $R^2$, $R^3$, $R^4$ and $R^5$ independently is H, halogen, aliphatic, hydroxyalkyl, protected hydroxyalkyl, aryl, heteroaryl, hydroxyl, protected hydroxyl, or two of $R^2$, $R^3$, $R^4$ and $R^5$ that are attached to the same carbon together form =O or =S.

Paragraph 29. The compound of any one of paragraphs 1-28, wherein each of $R^2$, $R^3$, $R^4$ and $R^5$ independently is halogen, alkyl, hydroxyalkyl, protected hydroxyl alkyl, phenyl, heteroaryl, hydroxyl, protected hydroxyl, or two of $R^2$, $R^3$, $R^4$ and $R^5$ that are attached to the same carbon together form =O or =S.

Paragraph 30. The compound of any one of paragraphs 1-29, wherein the

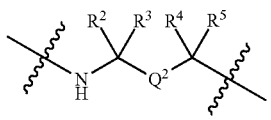

moiety is

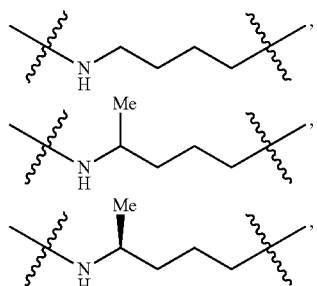

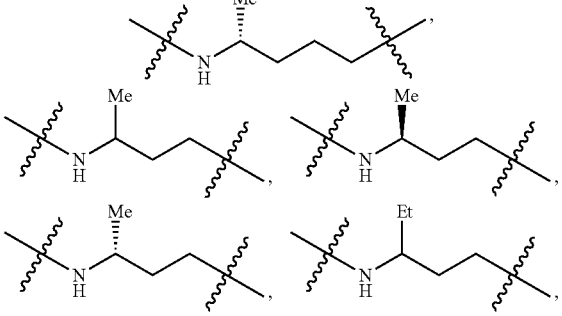

-continued

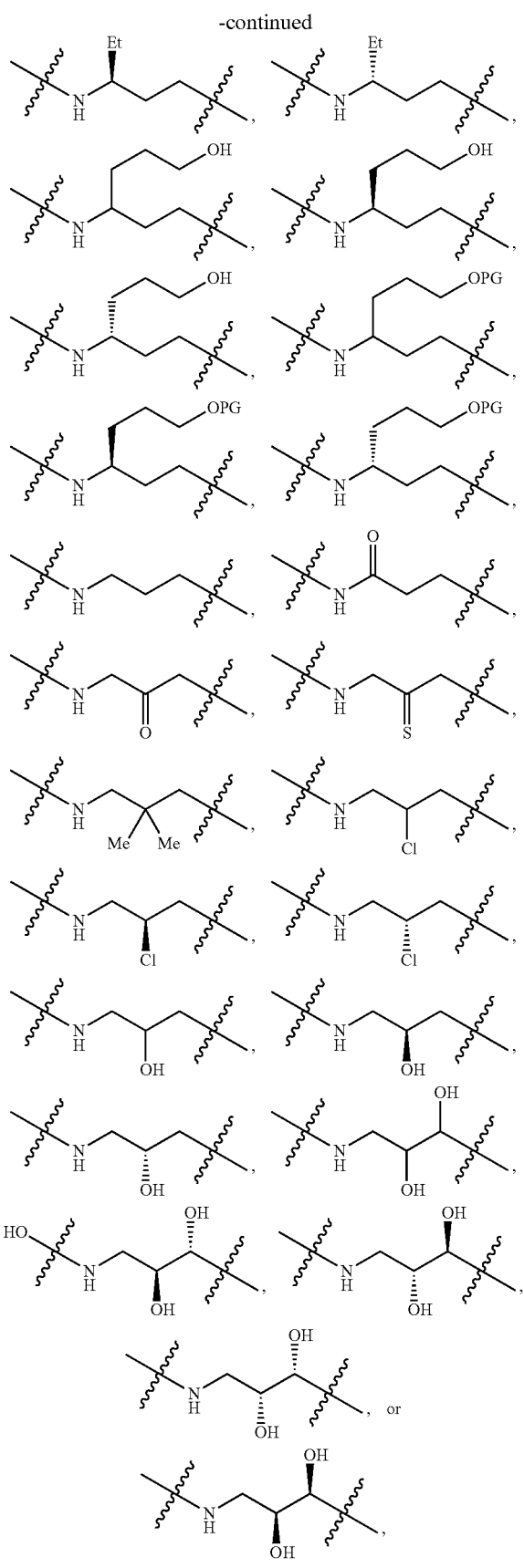

wherein PG is a hydroxyl protecting group.

Paragraph 31. The compound of paragraph 30, wherein PG is methoxymethyl (MOM), tert-butyl, iso-propyl, tert-butyldimethylsilyl (TBS or TBDMS), trimethylsilyl (TMS), triethylsilyl (TES), tert-butyldiphenylsilyl (TBDPS), or tri-isopropylsilyl (TIPS).

Paragraph 32. The compound of any one of paragraphs 1-31, wherein $R^{14}$ is acyl, alkyl, aralkyl, cycloalkylalkyl, hydroxyalkyl, carboxylic ester, carboxylic acid, or a combination thereof.

Paragraph 33. The compound of any one of paragraphs 1-32, wherein $R^{14}$ is acyl optionally substituted with one or more hydroxyl.

Paragraph 34. The compound of any one of paragraphs 1-33, wherein $R^{14}$ is

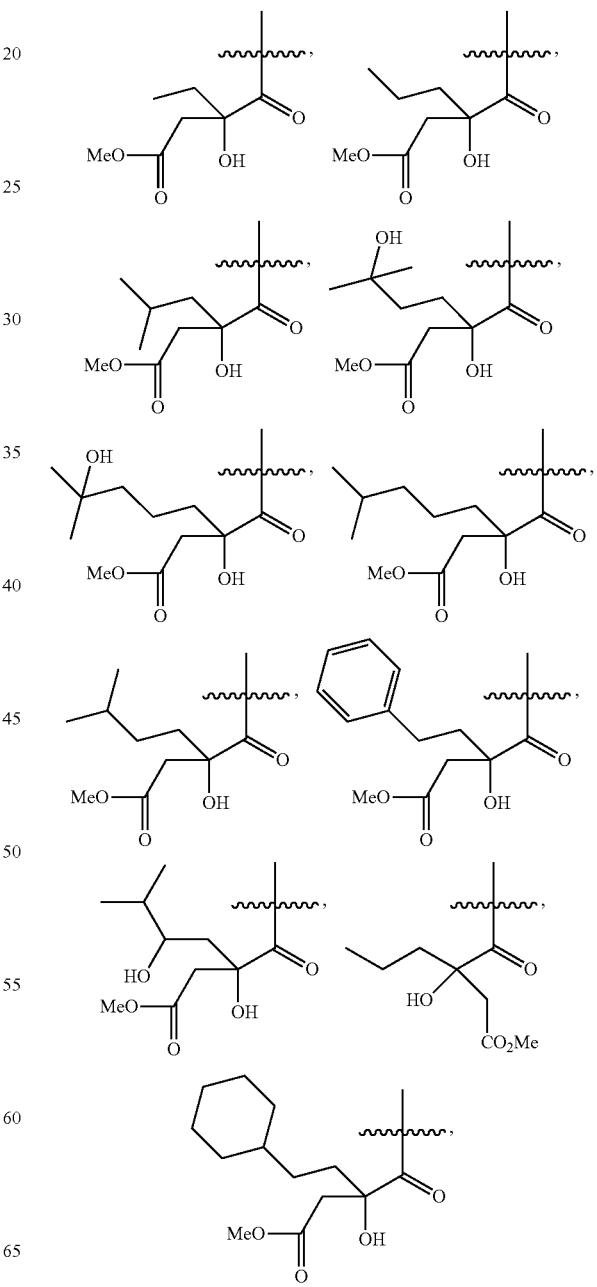

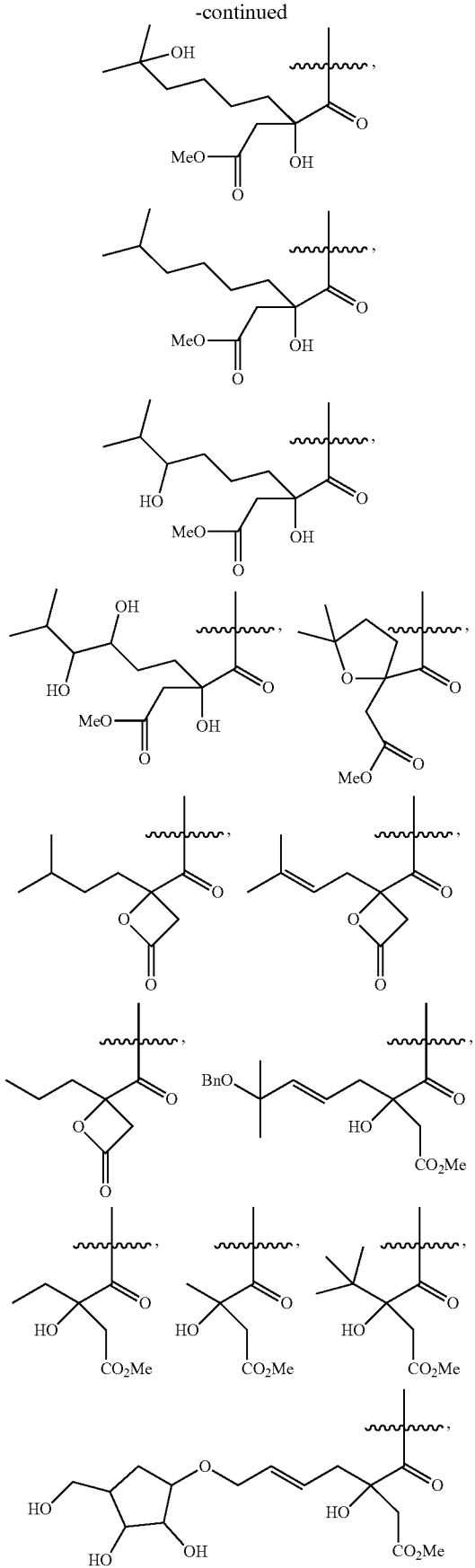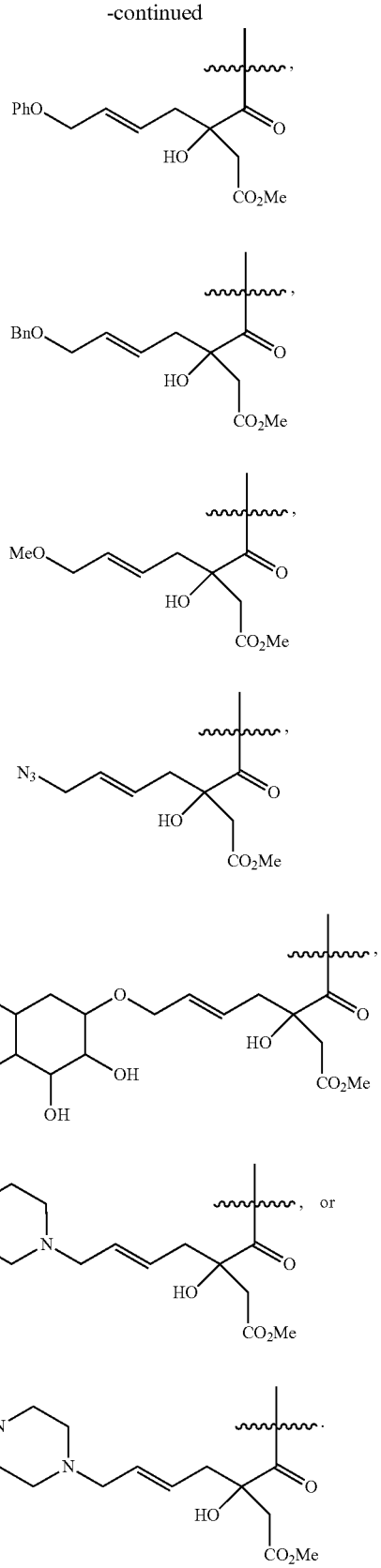
Paragraph 35. The compound of any one of paragraphs 1-34, wherein $R^{14}$ is

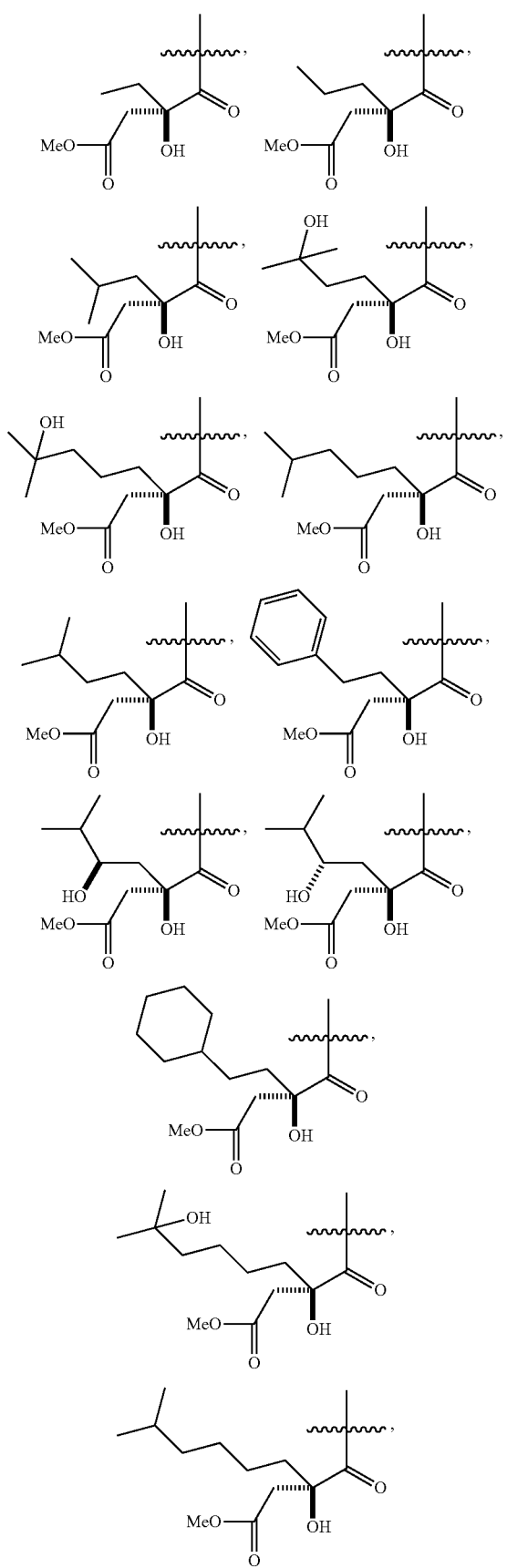
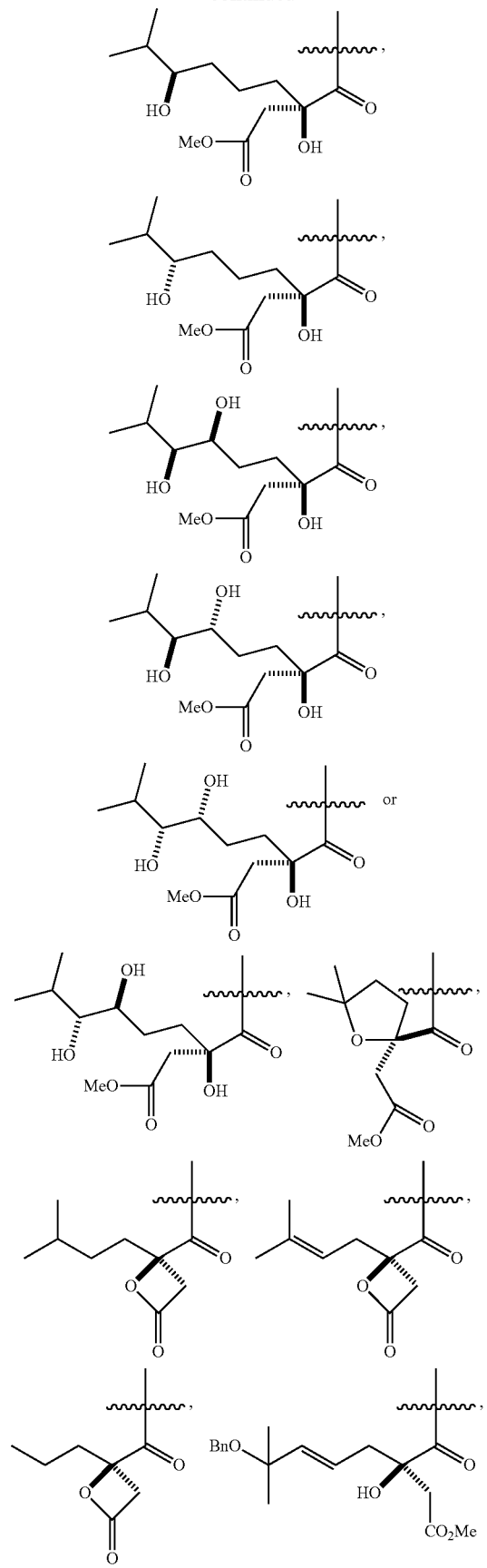

-continued

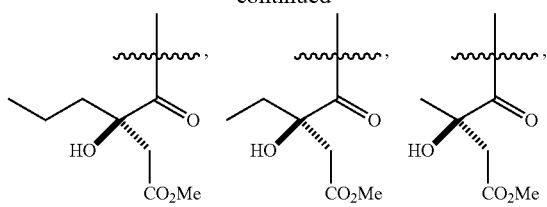

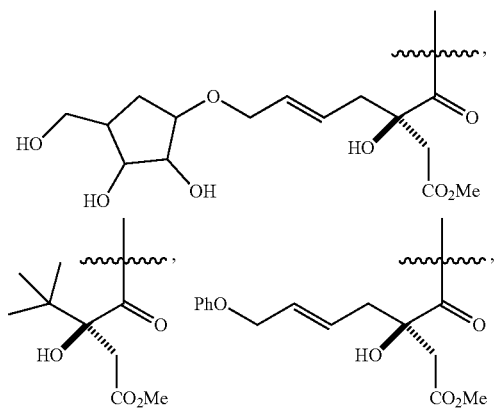

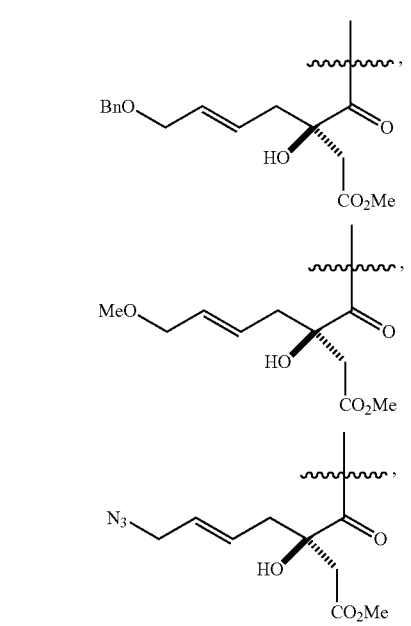

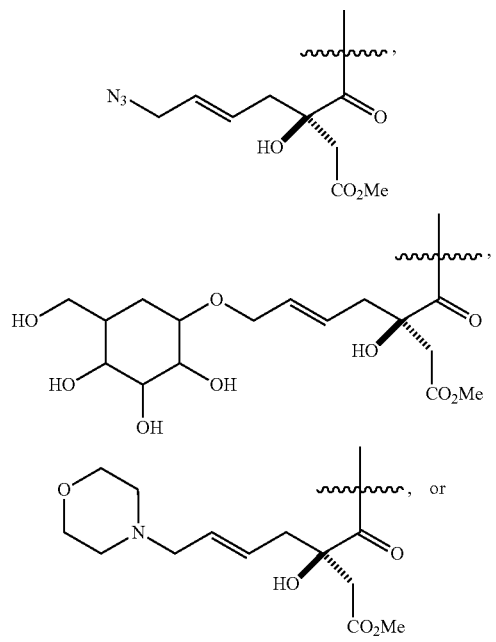

-continued

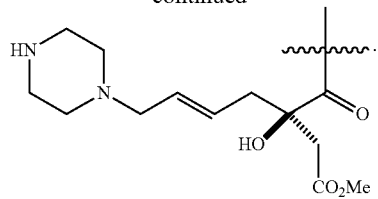

Paragraph 36. The compound of any one of paragraphs 1-35, wherein the compound has a formula:

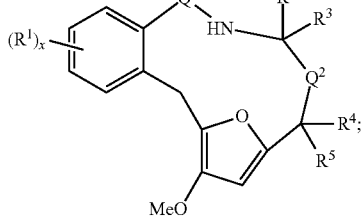

or a salt, solvate, N-oxide, prodrug, diastereomer or enantiomer thereof.

Paragraph 37. The compound of any one of paragraphs 1-35, wherein the compound has a formula:

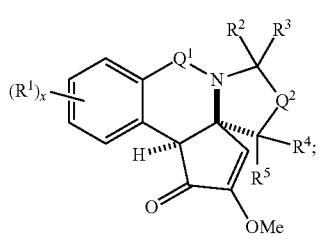

or a salt, solvate, N-oxide, prodrug, diastereomer or enantiomer thereof.

Paragraph 38. The compound of any one of paragraphs 1-35, wherein the compound has a formula:

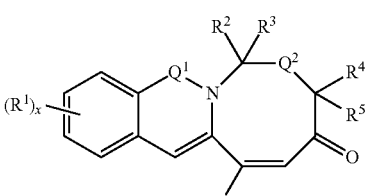

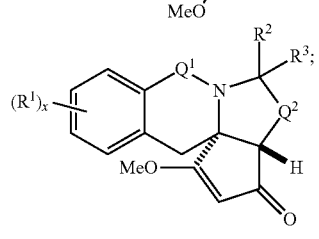

or a salt, solvate, N-oxide, prodrug, diastereomer or enantiomer thereof.

Paragraph 39. The compound of any one of paragraphs 1-35, wherein the compound has a formula selected from:

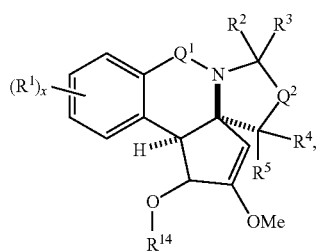
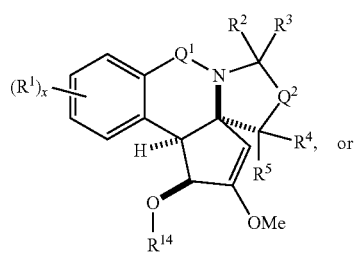
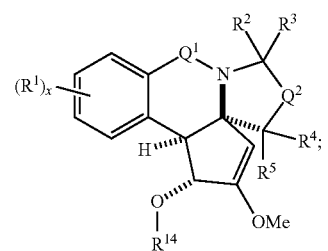
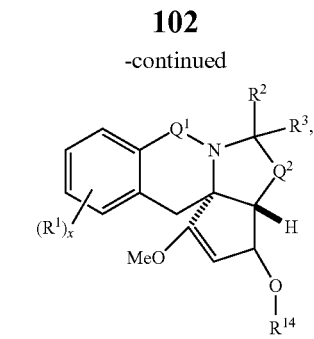
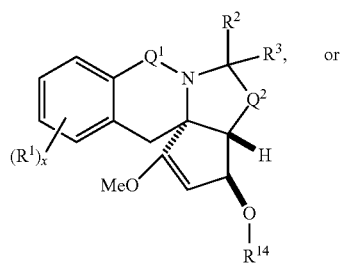
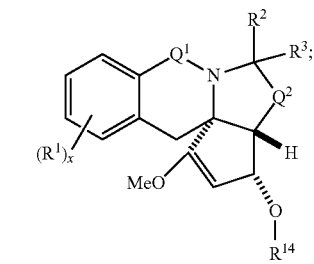
or a salt, solvate, N-oxide, prodrug, diastereomer or enantiomer thereof.
Paragraph 40. The compound of any one of paragraphs 1-35, wherein the compound has a formula selected from:
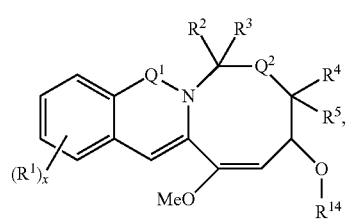
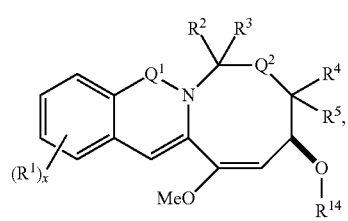
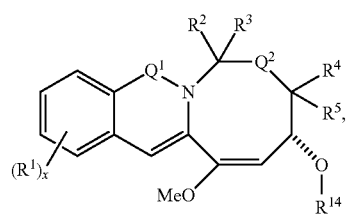
or a salt, solvate, N-oxide, prodrug, diastereomer or enantiomer thereof.
Paragraph 41. The compound of any one of paragraphs 1-35, wherein the compound has a formula selected from
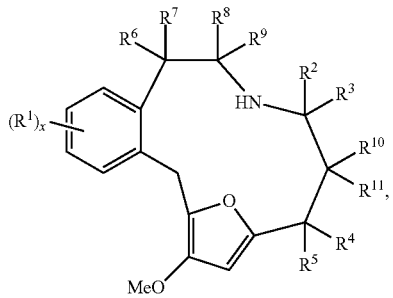
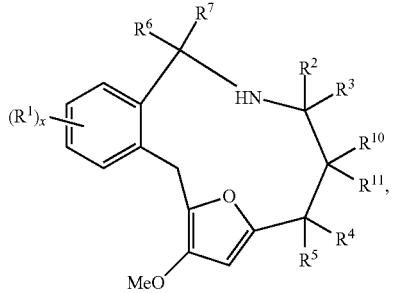

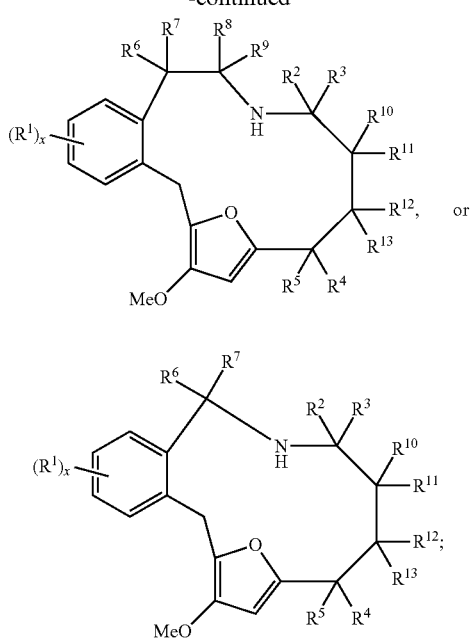

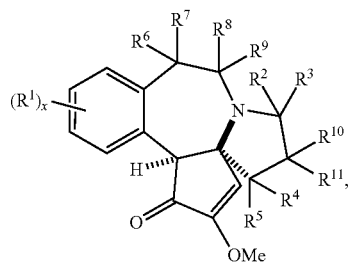

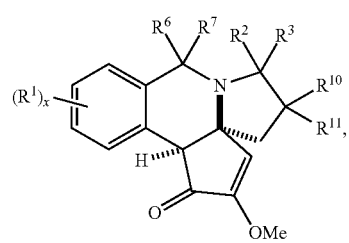

or a salt, solvate, N-oxide, prodrug, diastereomer or enantiomer thereof, wherein:

each of $R^6$, $R^7$, $R^8$, and $R^9$, independently is selected from H, halogen, aliphatic, hydroxyalkyl, protected hydroxyalkyl, aryl, hydroxyl, protected hydroxyl, haloalkyl, amino, protected amino, carboxylic ester, or two of $R^6$, $R^7$, $R^8$ and $R^9$ that are attached to the same carbon together form =O or =S, or a combination thereof, and each of $R^{10}$, $R^{11}$, $R^{12}$, and $R^{13}$ independently is selected from H, halogen, aliphatic, hydroxyalkyl, protected hydroxyalkyl, aryl, hydroxyl, protected hydroxyl, haloalkyl, amino, protected amino, carboxylic ester, or two of $R^{10}$, $R^{11}$, $R^{12}$ and $R^{13}$ that are attached to the same carbon together form =O or =S, or a combination thereof.

Paragraph 42. The compound of any one of paragraphs 1-35, wherein the compound has a formula selected from

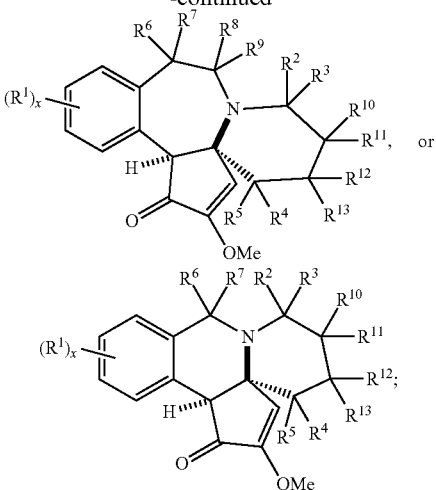

or a salt, solvate, N-oxide, prodrug, diastereomer or enantiomer thereof, wherein:

each of $R^6$, $R^7$, $R^8$, and $R^9$, independently is selected from H, halogen, aliphatic, hydroxyalkyl, protected hydroxyalkyl, aryl, hydroxyl, protected hydroxyl, haloalkyl, amino, protected amino, carboxylic ester, or two of $R^6$, $R^7$, $R^8$ and $R^9$ that are attached to the same carbon together form =O or =S, or a combination thereof, and each of $R^{10}$, $R^{11}$, $R^{12}$, and $R^{13}$ independently is selected from H, halogen, aliphatic, hydroxyalkyl, protected hydroxyalkyl, aryl, hydroxyl, protected hydroxyl, haloalkyl, amino, protected amino, carboxylic ester, or two of $R^{10}$, $R^{11}$, $R^{12}$ and $R^{13}$ that are attached to the same carbon together form =O or =S, or a combination thereof.

Paragraph 43. The compound of any one of paragraphs 1-35, wherein the compound has a formula selected from

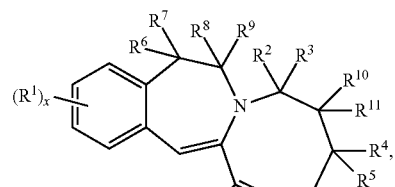

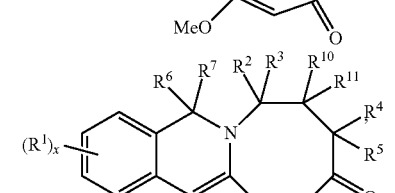

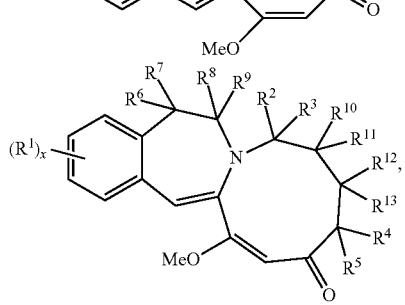

-continued

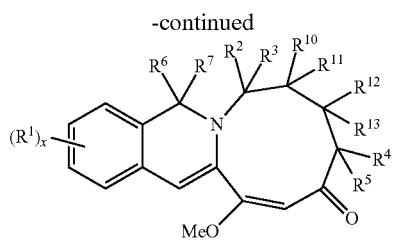

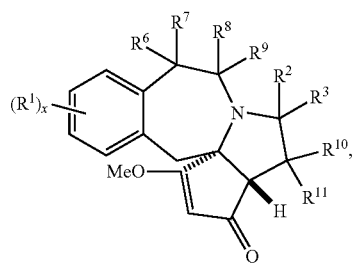

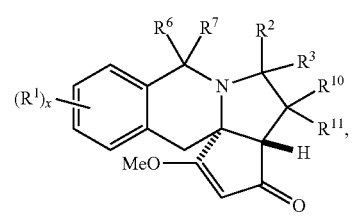

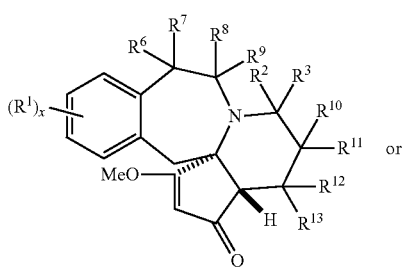

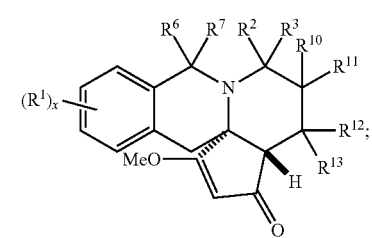

or a salt, solvate, N-oxide, prodrug, diastereomer or enantiomer wherein each of $R^6$, $R^7$, $R^8$, and $R^9$, independently is selected from H, halogen, aliphatic, hydroxyalkyl, protected hydroxyalkyl, aryl, hydroxyl, protected hydroxyl, haloalkyl, amino, protected amino, carboxylic ester, or two of $R^6$, $R^7$, $R^8$ and $R^9$ that are attached to the same carbon together form =O or =S, or a combination thereof, and each of $R^{10}$, $R^{11}$, $R^{12}$, and $R^{13}$ independently is selected from H, halogen, aliphatic, hydroxyalkyl, protected hydroxyalkyl, aryl, hydroxyl, protected hydroxyl, haloalkyl, amino, protected amino, carboxylic ester, or two of $R^{10}$, $R^{11}$, $R^{12}$ and $R^{13}$ that are attached to the same carbon together form =O or =S, or a combination thereof.

Paragraph 44. The compound of any one of paragraphs 1-35, wherein the compound has a formula

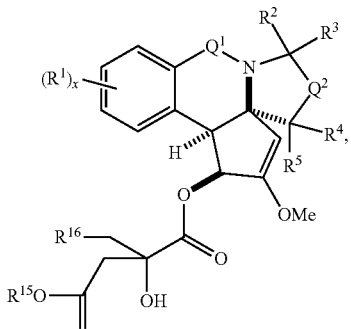

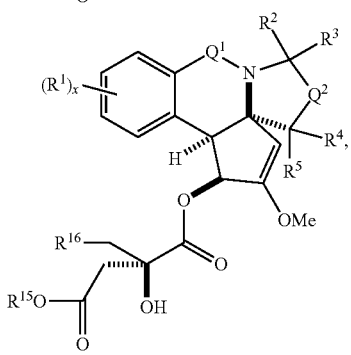

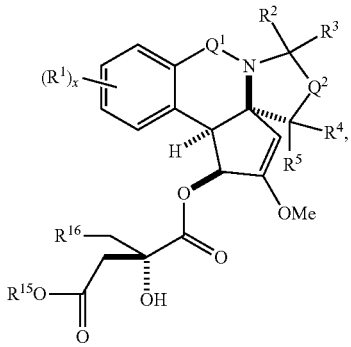

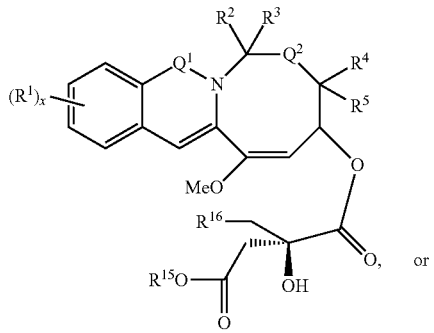

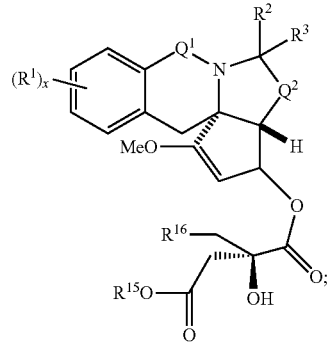

or a salt, solvate, N-oxide, prodrug, diastereomer or enantiomer wherein:

$R^{15}$ is H or alkyl, such as $C_{1-6}$alkyl, or $C_{1-4}$alkyl; and
$R^{16}$ is alkyl, aralkyl, hydroxyalkyl, or cycloalkylalkyl.

Paragraph 45. The compound of paragraph 44, wherein the compound has a formula selected from

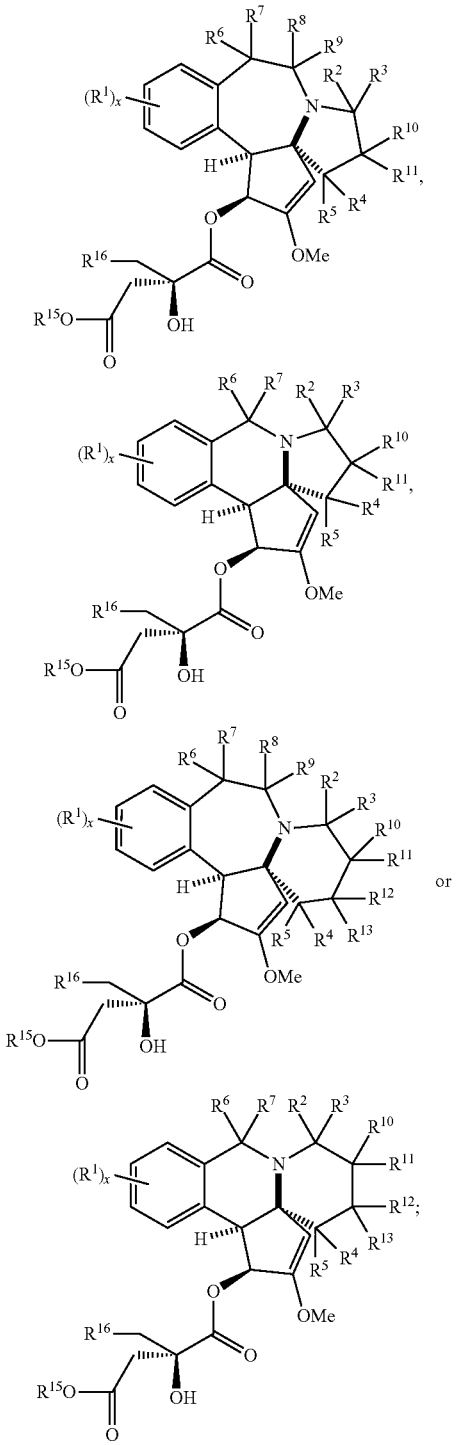

or a salt, solvate, N-oxide, prodrug, diastereomer or enantiomer wherein:

each of $R^6$, $R^7$, $R^8$, and $R^9$, independently is selected from H, halogen, aliphatic, hydroxyalkyl, protected hydroxyalkyl, aryl, hydroxyl, protected hydroxyl, haloalkyl, amino, protected amino, carboxylic ester, or two of $R^6$, $R^7$, $R^8$ and $R^9$ that are attached to the same carbon together form =O or =S, or a combination thereof, and each of $R^{10}$, $R^{11}$, $R^{12}$, and $R^{13}$ independently is selected from H, halogen, aliphatic, hydroxyalkyl, protected hydroxyalkyl, aryl, hydroxyl, protected hydroxyl, haloalkyl, amino, protected amino, carboxylic ester, or two of $R^{10}$, $R^{11}$, $R^{12}$ and $R^{13}$ that are attached to the same carbon together form =O or =S, or a combination thereof.

Paragraph 46. The compound of paragraph 44, wherein the compound has a formula selected from

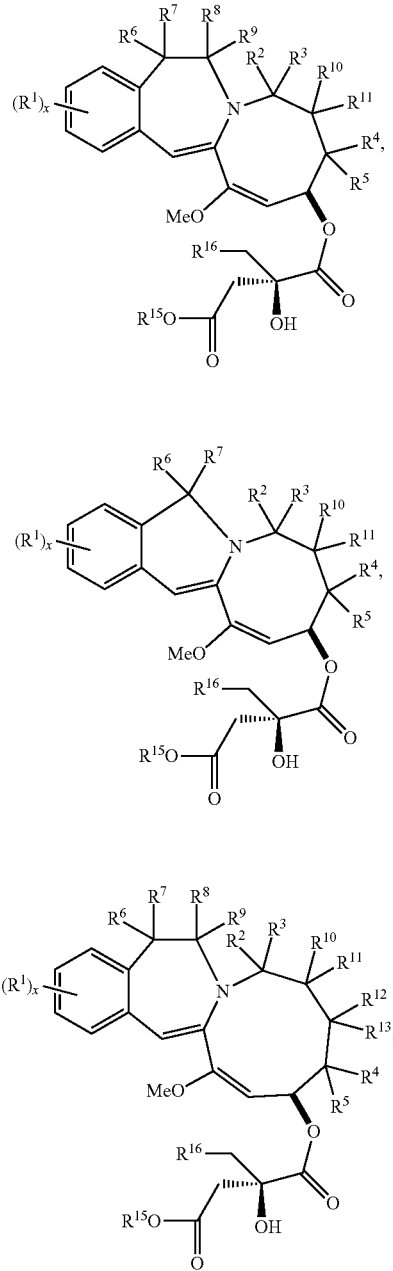

-continued
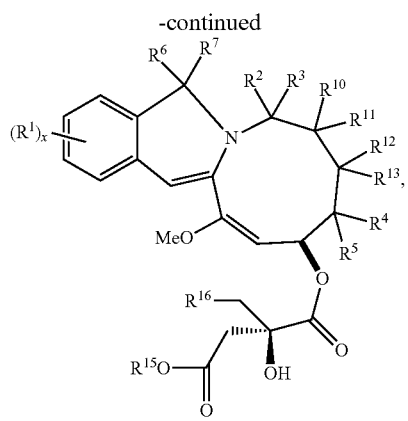
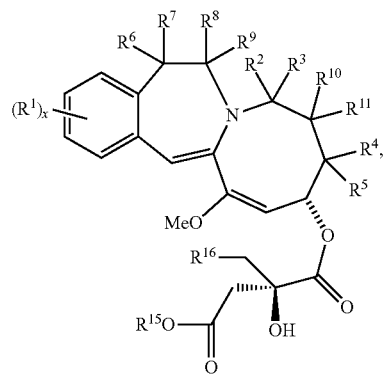
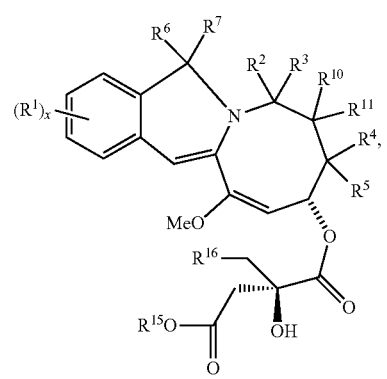
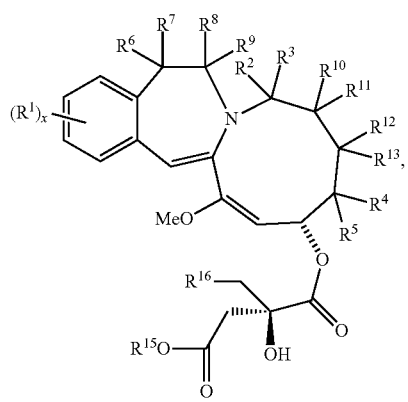
-continued
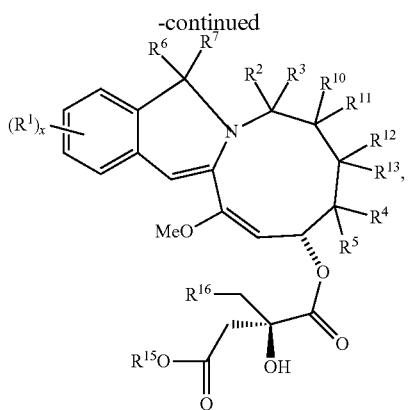
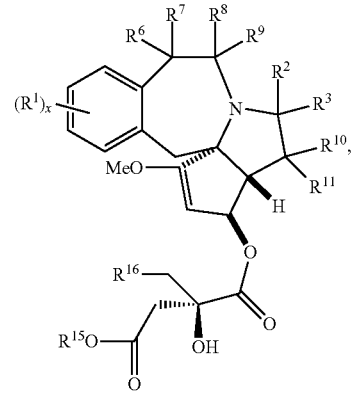
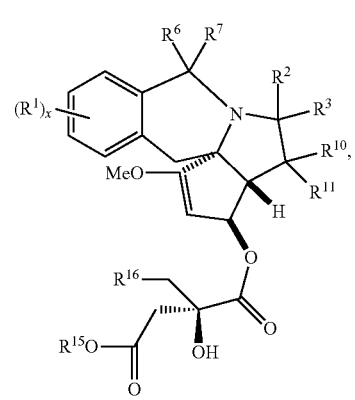
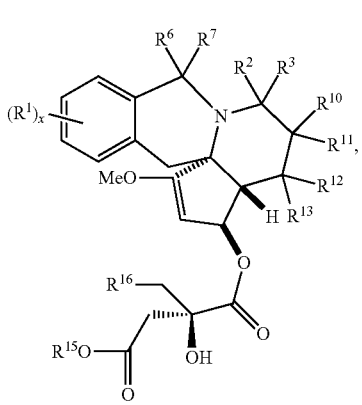

111

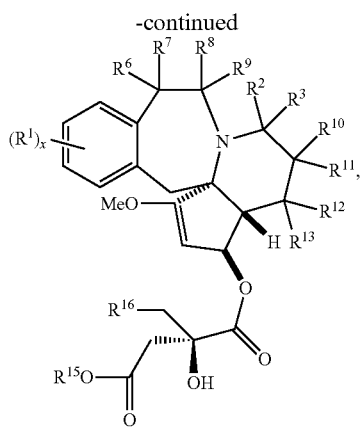

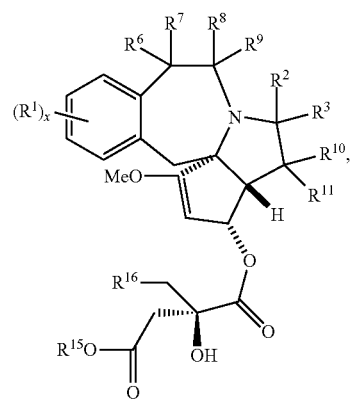

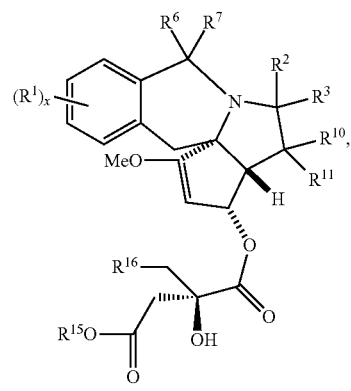

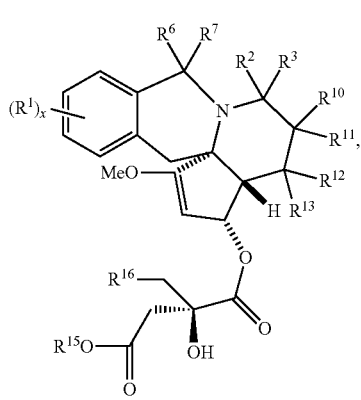

112

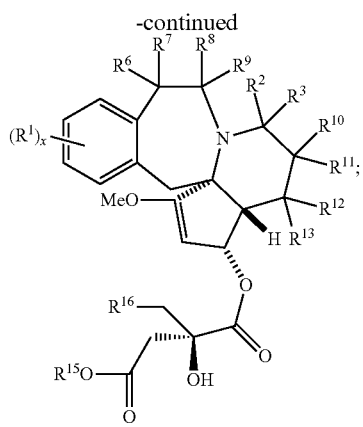

or a salt, solvate, N-oxide, prodrug, diastereomer or enantiomer wherein:
each of $R^6$, $R^7$, $R^8$, and $R^9$, independently is selected from H, halogen, aliphatic, hydroxyalkyl, protected hydroxyalkyl, aryl, hydroxyl, protected hydroxyl, haloalkyl, amino, protected amino, carboxylic ester, or two of $R^6$, $R^7$, $R^8$ and $R^9$ that are attached to the same carbon together form =O or =S, or a combination thereof, and
each of $R^{10}$, $R^{11}$, $R^{12}$, and $R^{13}$ independently is selected from H, halogen, aliphatic, hydroxyalkyl, protected hydroxyalkyl, aryl, hydroxyl, protected hydroxyl, haloalkyl, amino, protected amino, carboxylic ester, or two of $R^{10}$, $R^{11}$, $R^{12}$ and $R^{13}$ that are attached to the same carbon together form =O or =S, or a combination thereof.

Paragraph 47. The compound of any one of paragraphs 41-43 and 45-46, wherein:
each of $R^6$, $R^7$, $R^8$, and $R^9$, independently is selected from H, halogen, alkyl, hydroxyalkyl, protected hydroxyalkyl, aryl, hydroxyl, protected hydroxyl, or two of $R^6$, $R^7$, $R^8$ and $R^9$ that are attached to the same carbon together form =O or =S, or a combination thereof; and
each of $R^{10}$, $R^{11}$, $R^{12}$, and $R^{13}$ independently is selected from H, halogen, akyl, hydroxyalkyl, protected hydroxyalkyl, aryl, hydroxyl, protected hydroxyl, or two of $R^{10}$, $R^{11}$, $R^{12}$ and $R^{13}$ that are attached to the same carbon together form =O or =S, or a combination thereof.

Paragraph 48. The compound of any one of paragraphs 41-47, wherein $R^{15}$ is methyl.

Paragraph 49. The compound of any one of paragraphs 41-48, wherein $R^{16}$ is methyl, ethyl, isopropyl

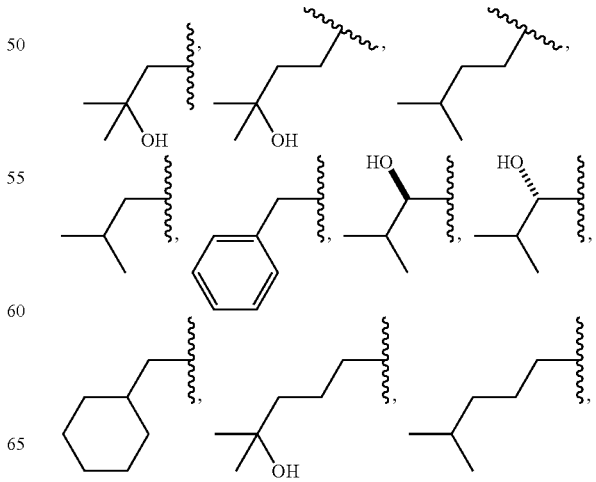

-continued

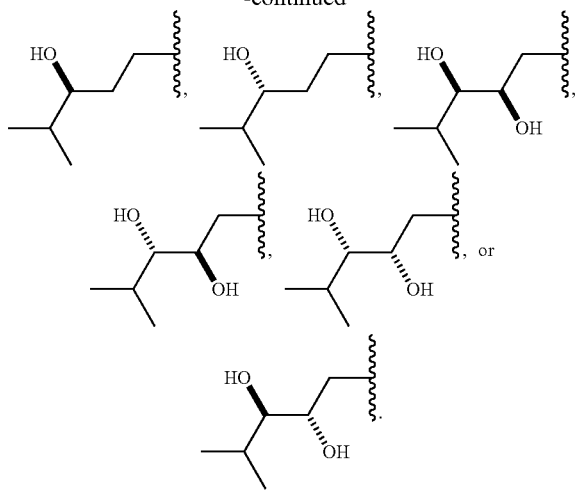

Paragraph 50. The compound of any one of paragraphs 1-49, wherein one or more of the following conditions apply:

the

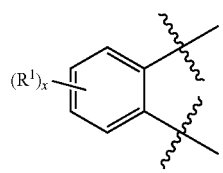

moiety is not

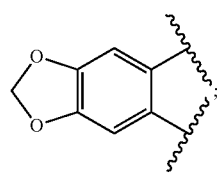 [SMILES: *c1cc2c(cc1*)OCO2]

if $R^2$, $R^3$, $R^4$ and $R^5$ are all hydrogen then $Q^2$ is not —$CH_2$—;
if $Q^2$ is —$CH_2$— then one or more of $R^2$, $R^3$, $R^4$ and $R^5$ is not hydrogen;
$Q^1$ is not —$CH_2CH_2$—;
at least one of $R^6$, $R^7$, $R^8$ and $R^9$ is not H; or
at least one of $R^2$, $R^3$, $R^4$, $R^5$, $R^{10}$ and $R^{11}$ is not hydrogen.

Paragraph 51. A composition, comprising the compound of any one of paragraphs 1-50, and a pharmaceutically acceptable excipient.

Paragraph 52. A method, comprising administering a compound according to any one of paragraphs 1-50, or a composition according to paragraph 51, to a subject.

Paragraph 53. The method of paragraph 52, wherein the subject is a human subject.

Paragraph 54. The method of paragraph 52 or paragraph 53, wherein the method comprises treating or preventing a proliferation disease.

Paragraph 55. The method of paragraph 54, wherein the proliferation disease is a non-solid tumor cancer.

Paragraph 56. The method of paragraph 54 or paragraph 55, wherein the proliferation disease is leukemia.

Paragraph 57. A method, comprising:
i) treating a protected hydroxyl ketone of formula A-1 with a haloactetate ester of formula A-2 to form a compound of formula A-3

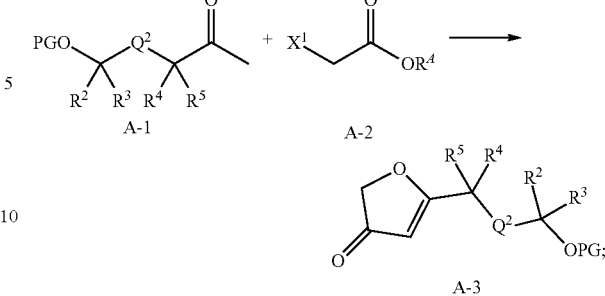

ii) treating the compound of formula A-3 with a protected amino compound of formula A-4 to form a compound of formula A-5

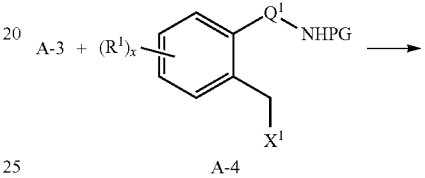

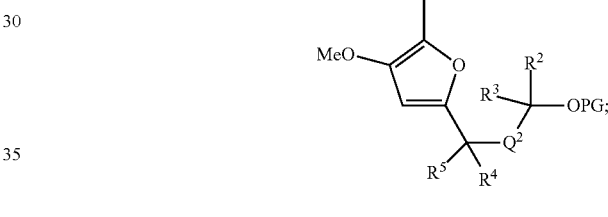

iii) converting the OPG moiety of A-5 to a leaving group in a compound of formula A-6

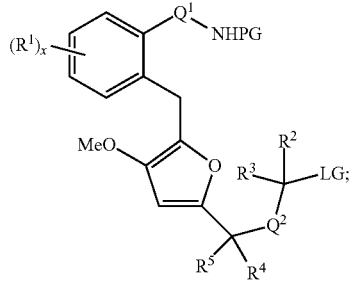

and
iv) cyclizing A-6 to form the compound of Formula I,

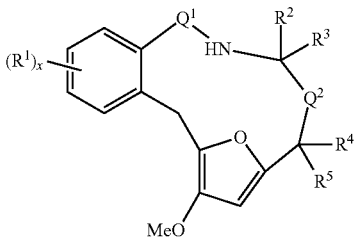

Formula I or a salt, solvate, N-oxide, prodrug, diastereomer or enantiomer thereof, wherein:

each PG independently is a protecting group;
LG is a leaving group;
each $X^1$ independently is a halogen;
x is from 0 to 4;
$R^a$ is alkyl;
each $R^1$ independently is hydroxyl, halogen, aliphatic, alkoxy, haloalkyl, amino, protected amino, carboxylic ester, or two $R^1$s, together with the atoms to which they are attached, form an aryl or heterocyclyl;
each of $R^2$, $R^3$, $R^4$ and $R^5$ independently is H, halogen, aliphatic, hydroxyalkyl, protected hydroxyalkyl, aryl, heteroaryl, hydroxyl, protected hydroxyl, haloalkyl, amino, protected amino, carboxylic ester, or two of $R^2$, $R^3$, $R^4$ and $R^5$ that are attached to the same carbon together form =O or =S; and
each of $Q^1$ and $Q^2$ independently is aliphatic.

Paragraph 58. The method of paragraph 57, wherein:
each PG independently is trifluoroacetate or a silyl protecting group;
LG is mesylate;
$X^1$ is Cl;
$R^4$ is $C_{1-2}$alkyl; or
a combination thereof.

Paragraph 59. The method of paragraph 57 of paragraph 58, further comprising:
v) treating the compound of Formula I with an oxidizing agent to form a racemic compound of Formula II

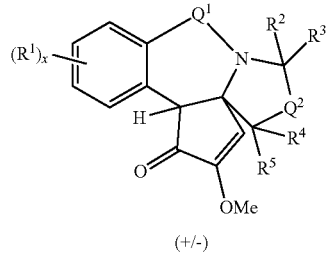

(+/-)

wherein x, $R^1$, $R^2$, $R^3$, $R^4$, $R^5$, $Q^1$ and $Q^2$ are as defined in paragraph 45.

Paragraph 60. The method of paragraph 59, wherein the oxidizing agent is DDQ.

Paragraph 61. The method of paragraph 59 or paragraph 60, further comprising:
vi) treating the racemic compound of Formula II with Ru(p-cymene)-(S,S)-TsDPEN, trimethylamine, and formic acid to form a compound of Formula A-7 and (+)-compound of Formula II

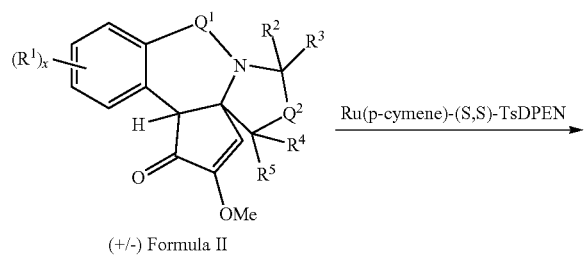

(+/-) Formula II

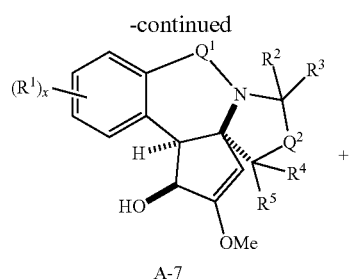

A-7

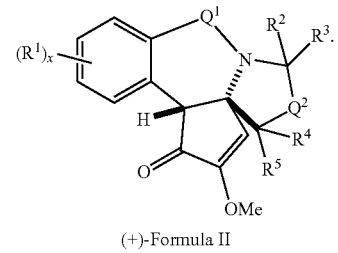

(+)-Formula II

Paragraph 62. The method of paragraph 61, further comprising treating the (+)-compound of Formula II with 2,2-dimethoxypropane and p-toluene sulfonic acid to form a racemic compound of Formula

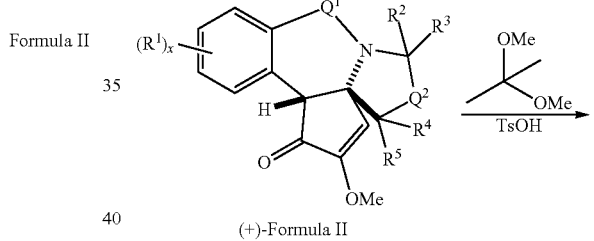

(+)-Formula II

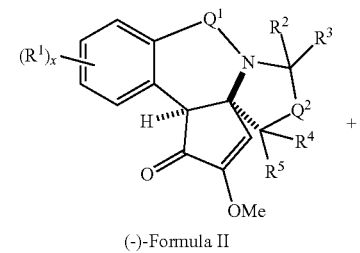

(-)-Formula II

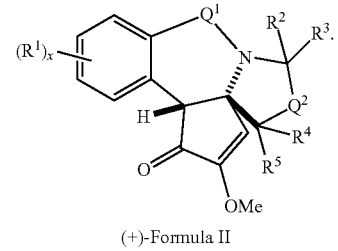

(+)-Formula II

Paragraph 63. A composition, comprising an oxidizing agent and a compound having a structure according to Formula I Formula I

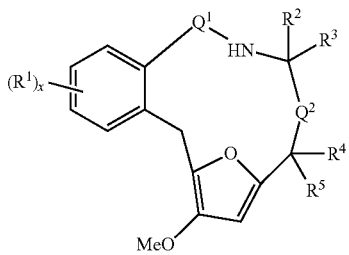

or a salt, solvate, N-oxide, prodrug, diastereomer or enantiomer thereof, wherein:

x is from 0 to 4;

each $R^1$ independently is hydroxyl, halogen, aliphatic, alkoxy, haloalkyl, amino, protected amino, carboxylic ester, or two $R^1$s, together with the atoms to which they are attached, form an aryl or heterocyclyl;

each of $R^2$, $R^3$, $R^4$ and $R^5$ independently is H, halogen, aliphatic, hydroxyalkyl, protected hydroxyalkyl, aryl, heteroaryl, hydroxyl, protected hydroxyl, haloalkyl, amino, protected amino, carboxylic ester, or two of $R^2$, $R^3$, $R^4$ and $R^5$ that are attached to the same carbon together form =O or =S; and each of $Q^1$ and $Q^2$ independently is aliphatic.

Paragraph 64. The composition of paragraph 63, wherein the oxidizing agent is DDQ.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound having a formula

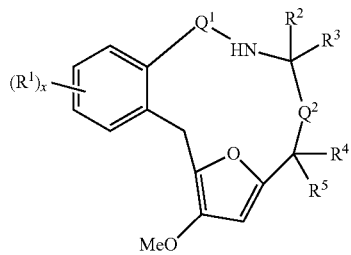

or a salt, solvate, N-oxide, diastereomer or enantiomer thereof, wherein:

x is from 0 to 4;

each $R^1$ independently is hydroxyl, halogen, aliphatic, alkoxy, haloalkyl, amino, protected amino, carboxylic ester, or two $R^1$s, together with the atoms to which they are attached, form an aryl or heterocyclyl;

each of $R^2$, $R^3$, $R^4$ and $R^5$ independently is H, halogen, aliphatic, hydroxyalkyl, protected hydroxyalkyl, aryl, heteroaryl, hydroxyl, protected hydroxyl, haloalkyl, amino, protected amino, carboxylic ester, or two of $R^2$, $R^3$, $R^4$ and $R^5$ that are attached to the same carbon together form =O or =S; and each of $Q^1$ and $Q^2$ independently is aliphatic.

2. The compound of claim 1, wherein x is 2, 3, or 4.

3. The compound of claim 1, wherein two $R^1$s together with the atoms to which they are attached, form an aryl or 5- or 6-membered heterocyclyl ring.

4. The compound of claim 3, wherein the 5- or 6-membered heterocyclyl is a pyridinyl, imidazolyl, pyrazolyl, pyrrolyl, oxazolyl, thiazolyl, furanyl, thiophenyl, 1,3-dioxole, 1,4-dioxine, 2,3-dihydro-1,4-dioxine, 1,4-oxazine, or 3,4-dihydro-1,4-oxazine.

5. The compound of claim 1, wherein the

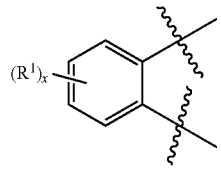

moiety is

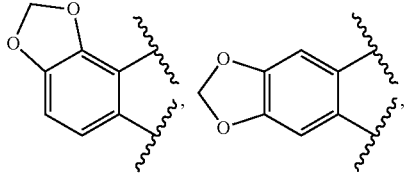

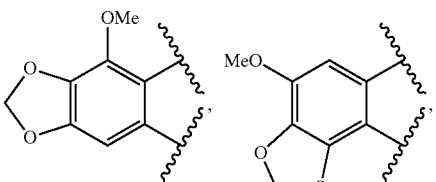

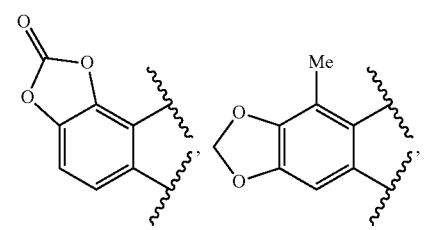

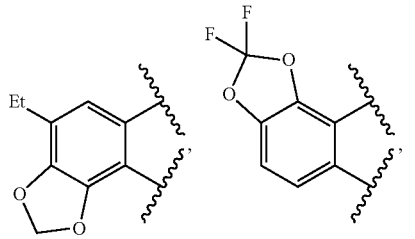

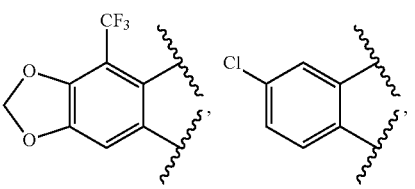

-continued

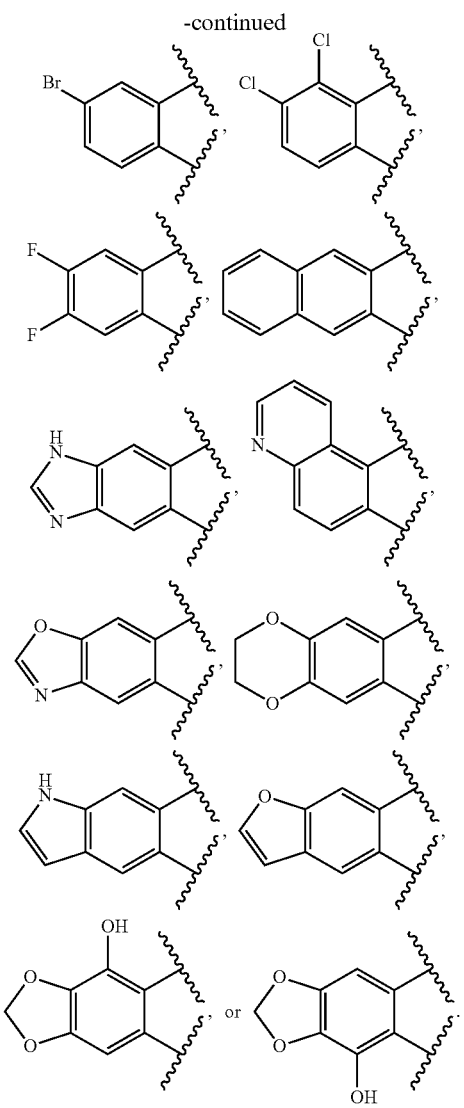

6. The compound of claim 1, wherein the

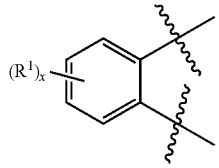

moiety is

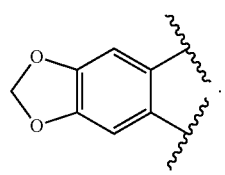 [SMILES: *c1cc2c(cc1*)OCO2]

7. The compound of claim 1, wherein each of $Q^1$ and $Q^2$ independently is alkyl optionally substituted with 1, 2, 3, or 4 substituents from halogen, alkyl, hydroxyalkyl, protected hydroxyalkyl, =O, =S, aryl, hydroxyl, protected hydroxyl, haloalkyl, amino, protected amino, or carboxylic ester.

8. The compound of claim 7, wherein each of $Q^1$ and $Q^2$ independently is $C_{1-2}$ alkyl optionally substituted with 1, 2, 3, or 4 substituents from halogen, alkyl, hydroxyalkyl, protected hydroxyalkyl, =O, =S, aryl, hydroxyl, protected hydroxyl, haloalkyl, amino, protected amino, or carboxylic ester.

9. The compound of claim 8,
wherein one or more of the following applies:
 i) $Q^1$ is —CH$_2$— or —CH$_2$CH$_2$—;
 ii) $Q^2$ is —CH$_2$— or —CH$_2$CH$_2$; or
 iii) $Q^1$ is —CH$_2$— or —CH$_2$CH$_2$— and $Q^2$ is —CH$_2$— or —CH$_2$CH$_2$.

10. The compound of claim 8, wherein one or both of the following applies:
 $Q^1$ is substituted with 1, 2, 3, or 4 substituents from methyl, ethyl, =O, =S, hydroxyl, phenyl, hydroxyethyl, hydroxypropyl, protected hydroxyalkyl, protected hydroxyl, or protected amino;
 $Q^2$ is substituted with 1, 2, 3, or 4 substituents from Cl, methyl, ethyl, =O, =S, hydroxyl, protected hydroxyl, hydroxyethyl, hydroxypropyl, protected hydroxyalkyl, protected hydroxyl, or protected amino.

11. The compound of claim 1, wherein each of $R^2$, $R^3$, $R^4$ and $R^5$ independently is H, halogen, aliphatic, hydroxyalkyl, protected hydroxyalkyl, aryl, heteroaryl, hydroxyl, protected hydroxyl, or two of $R^2$, $R^3$, $R^4$ and $R^5$ that are attached to the same carbon together form =O or =S.

12. The compound of claim 1, wherein each of $R^2$, $R^3$, $R^4$ and $R^5$ is H.

13. The compound of claim 1, wherein the

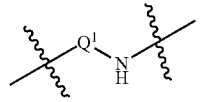

moiety is

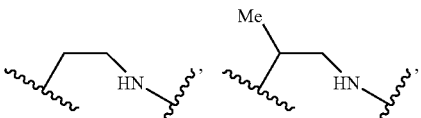

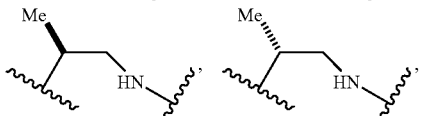

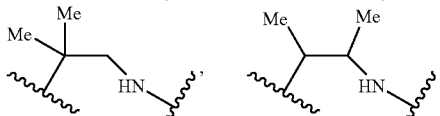

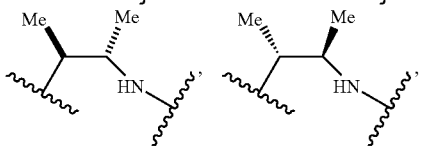

-continued
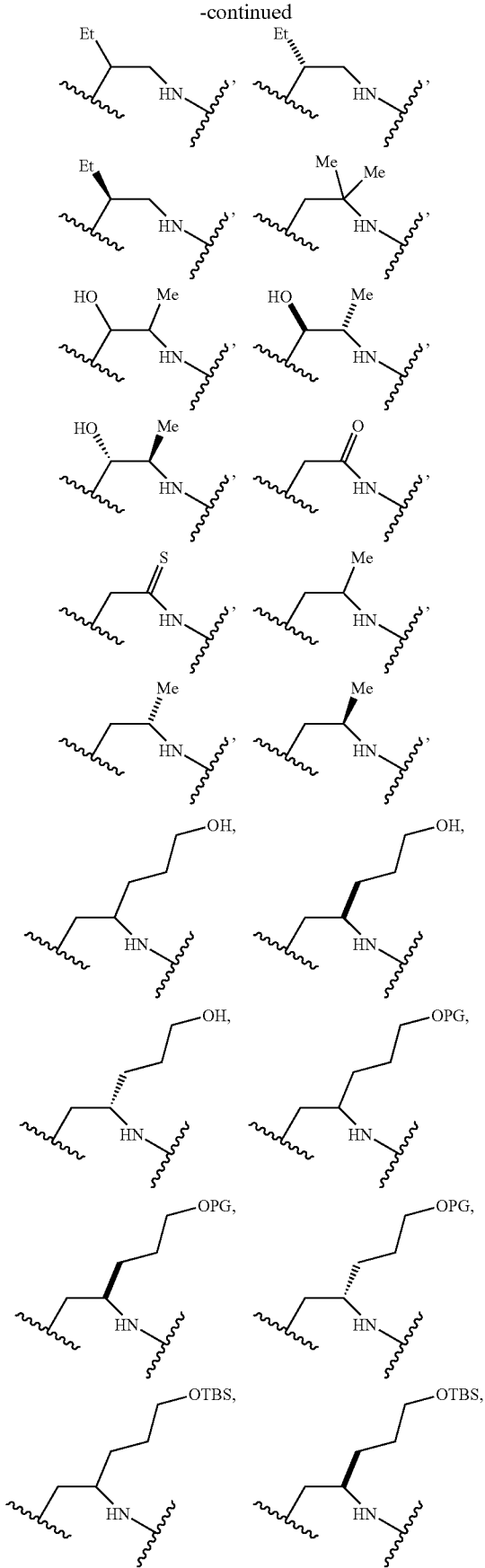
-continued
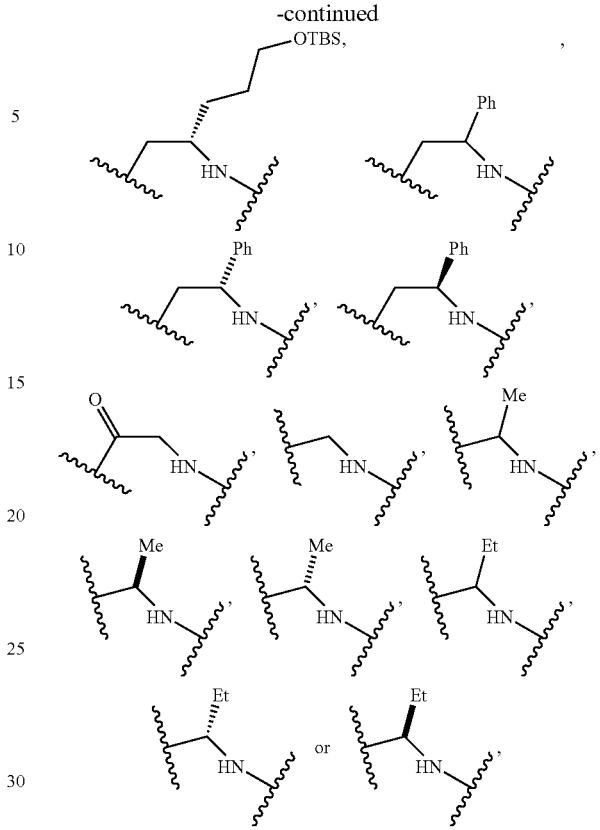
wherein PG is a hydroxyl protecting group.
14. The compound of claim 13, wherein PG is methoxymethyl (MOM), tert-butyl, iso-propyl, tert-butyldimethylsilyl (TBS or TBDMS), trimethylsilyl (TMS), triethylsilyl (TES), tert-butyldiphenylsilyl (TBDPS), or triisopropylsilyl (TIPS).
15. The compound of claim 1, wherein the
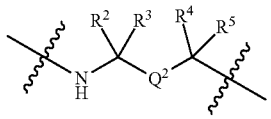
moiety is
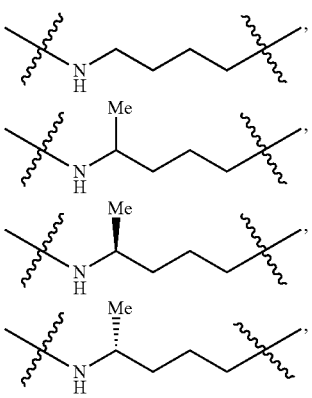

-continued

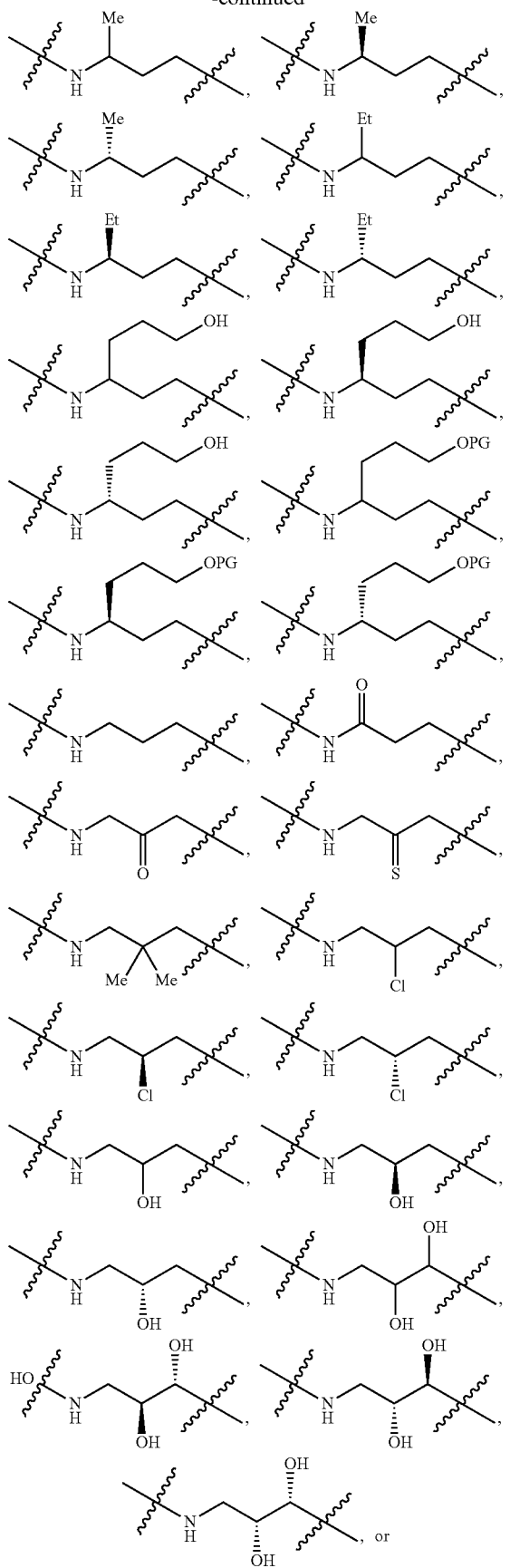

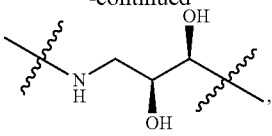

wherein PG is a hydroxyl protecting group.

16. The compound of claim 15, wherein PG is methoxymethyl (MOM), tert-butyl, iso-propyl, tert-butyldimethylsilyl (TBS or TBDMS), trimethylsilyl (TMS), triethylsilyl (TES), tert-butyldiphenylsilyl (TBDPS), or triisopropylsilyl (TIPS).

17. The compound of claim 1, wherein the compound is

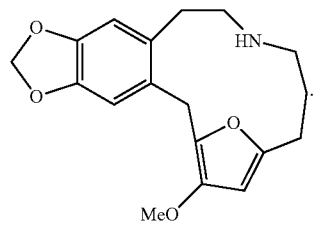 [SMILES: COC1=C2Cc3cc4c(cc3CCNCCCC(=C1)O2)OCO4]

18. A method for making a compound of Formula I, comprising:
i) treating a protected hydroxyl ketone of formula A-1 with a haloacetate ester of formula A-2 to form a compound of formula A-3

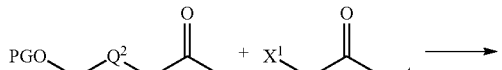

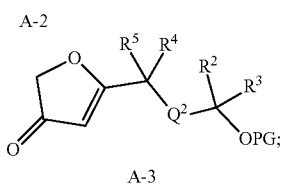

ii) treating the compound of formula A-3 with a protected amino compound of formula A-4 to form a compound of formula A-5

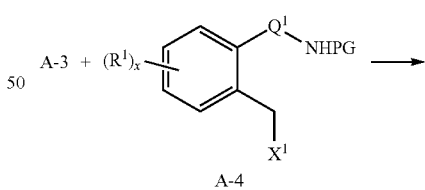

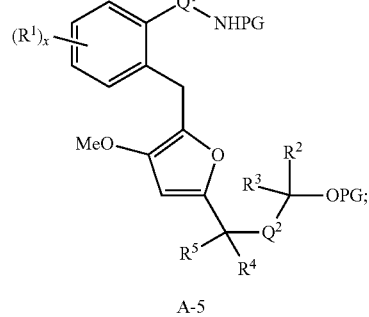

iii) converting the OPG moiety of A-5 to a leaving group in a compound of formula A-6

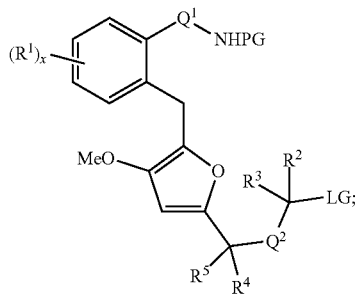

and iv) cyclizing A-6 to form the compound of Formula I,

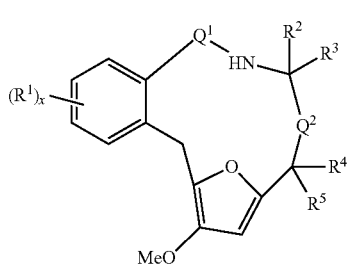

or a salt, solvate, N-oxide, diastereomer or enantiomer thereof, wherein:

each PG independently is a protecting group;

LG is a leaving group;

each $X^1$ independently is a halogen;

x is from 0 to 4;

$R^4$ is alkyl;

if present, each $R^1$ independently is hydroxyl, halogen, aliphatic, alkoxy, haloalkyl, amino, protected amino, carboxylic ester, or two $R^1$s, together with the atoms to which they are attached, form an aryl or heterocyclyl;

each of $R^2$, $R^3$, $R^4$ and $R^5$ independently is H, halogen, aliphatic, hydroxyalkyl, protected hydroxyalkyl, aryl, heteroaryl, hydroxyl, protected hydroxyl, haloalkyl, amino, protected amino, carboxylic ester, or two of $R^2$, $R^3$, $R^4$ and $R^5$ that are attached to the same carbon together form =O or =S; and each of $Q^1$ and $Q^2$ independently is aliphatic.

19. The method of claim 18, wherein one or more of the following applies:

i) each PG independently is trifluoroacetate or a silyl protecting group;

ii) LG is mesylate;

iii) $X^1$ is Cl;

iv) $R^4$ is $C_{1-2}$ alkyl.

20. A method for making a compound of Formula (II), comprising:

treating a compound of Formula I

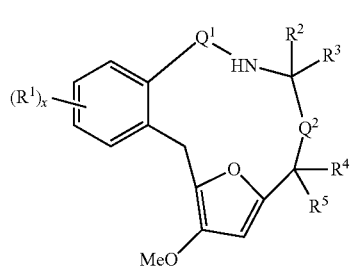

or a salt, solvate, N-oxide, diastereomer or enantiomer thereof, with an oxidizing agent to form a racemic compound of Formula II

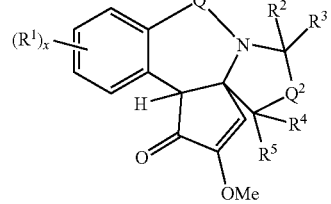

or a salt, solvate, or N-oxide thereof, wherein:

x is from 0 to 4;

if present, each $R^1$ independently is hydroxyl, halogen, aliphatic, alkoxy, haloalkyl, amino, protected amino, carboxylic ester, or two $R^1$s, together with the atoms to which they are attached, form an aryl or heterocyclyl;

each of $R^2$, $R^3$, $R^4$ and $R^5$ independently is H, halogen, aliphatic, hydroxyalkyl, protected hydroxyalkyl, aryl, heteroaryl, hydroxyl, protected hydroxyl, haloalkyl, amino, protected amino, carboxylic ester, or two of $R^2$, $R^3$, $R^4$ and $R^5$ that are attached to the same carbon together form =O or =S; and each of $Q^1$ and $Q^2$ independently is aliphatic.

21. The method of claim 20, wherein the oxidizing agent is DDQ.

22. The method of claim 20, further comprising:

treating the racemic compound of Formula II with Ru(p-cymene)-(S,S)-TsDPEN, trimethylamine, and formic acid to form a compound of Formula A-7 and a (+)-compound of Formula II

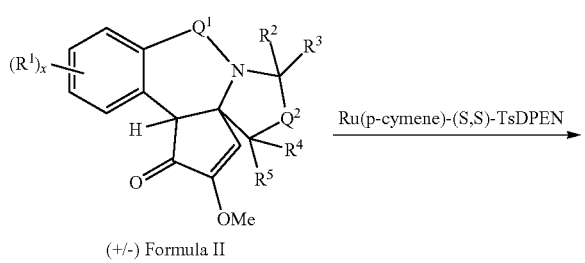

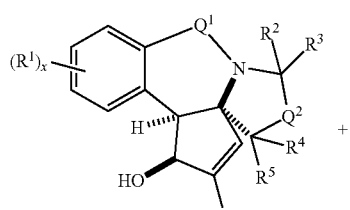

A-7

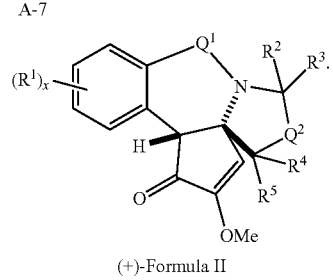

(+)-Formula II

23. The method of claim 22, further comprising treating the (+)-compound of Formula II with 2,2-dimethoxypropane and p-toluene sulfonic acid to form a second portion of racemic compound according to Formula II

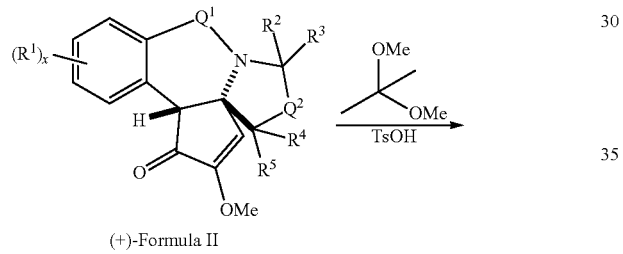

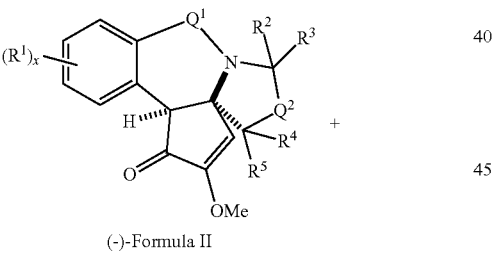

(+)-Formula II

24. The method of claim 22, wherein the compound of formula I is

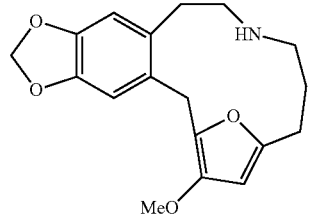 [SMILES: COC1=C2Cc3cc4c(cc3CCNCCCC(=C1)O2)OCO4]

and the compound of formula A-7 is

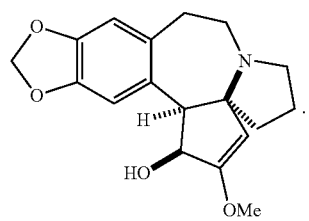 [SMILES: COC1=C[C@]23CCCN2CCc2cc4c(cc2[C@@H]3[C@@H]1O)OCO4]

25. The method of claim 18, wherein $R^2$, $R^3$, $R^4$, and $R^5$ are all H.

26. The method of claim 18, wherein:
$R^2$, $R^3$, $R^4$, and $R^5$ are all H;
$Q^1$ is —$CH_2CH_2$—;
$Q^2$ is —CH—;
the

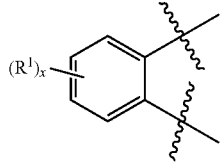

moiety is

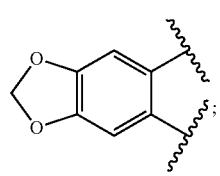 [SMILES: *c1cc2c(cc1*)OCO2]

and
the compound of Formula I is

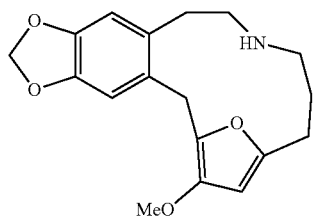

* * * * *